(12) United States Patent
Maute et al.

(10) Patent No.: US 10,316,094 B2
(45) Date of Patent: *Jun. 11, 2019

(54) COMPOSITIONS AND METHODS FOR INDUCING PHAGOCYTOSIS OF MHC CLASS I POSITIVE CELLS AND COUNTERING ANTI-CD47/SIRPA RESISTANCE

(71) Applicant: The Board of Trustees of the Leland Stanford Junior University, Stanford, CA (US)

(72) Inventors: Roy Louis Maute, San Francisco, CA (US); Kipp Andrew Weiskopf, Sudbury, MA (US); Aaron Michael Ring, New Haven, CT (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/518,976

(22) PCT Filed: Oct. 23, 2015

(86) PCT No.: PCT/US2015/057233
§ 371 (c)(1),
(2) Date: Apr. 13, 2017

(87) PCT Pub. No.: WO2016/065329
PCT Pub. Date: Apr. 28, 2016

(65) Prior Publication Data
US 2018/0251558 A1 Sep. 6, 2018

Related U.S. Application Data

(60) Provisional application No. 62/068,531, filed on Oct. 24, 2014.

(51) Int. Cl.
| C07K 16/28 | (2006.01) |
| A61K 38/17 | (2006.01) |
| A61K 45/06 | (2006.01) |
| A61K 39/00 | (2006.01) |

(52) U.S. Cl.
CPC ...... *C07K 16/2833* (2013.01); *A61K 38/1774* (2013.01); *A61K 45/06* (2013.01); *C07K 16/2803* (2013.01); *C07K 16/2863* (2013.01); *A61K 2039/505* (2013.01); *A61K 2039/507* (2013.01); *C07K 2317/24* (2013.01); *C07K 2317/55* (2013.01); *C07K 2317/565* (2013.01); *C07K 2317/73* (2013.01); *C07K 2317/76* (2013.01)

(58) Field of Classification Search
CPC ............ C07K 2317/76; C07K 16/30; C07K 16/2833; C07K 16/3061; C07K 16/2896; C07K 2317/75; C07K 14/7051; C07K 2317/73; C07K 2317/732; A61K 2039/505; A61K 47/6851; A61K 47/6849; A61K 47/6863; A61K 35/17; G01N 33/5011; G01N 33/57426; G01N 2500/04; G01N 33/56977; G01N 2333/70589; G01N 2333/70596; G01N 2333/715; Y02A 90/26

See application file for complete search history.

(56) References Cited

U.S. PATENT DOCUMENTS

| 7,494,647 B2 | 2/2009 | Sato et al. |
| 2003/0060614 A1 | 3/2003 | Cosman et al. |
| 2004/0044187 A1 | 3/2004 | Sato et al. |
| 2005/0037002 A1 | 2/2005 | Velardi et al. |
| 2008/0038257 A1 | 2/2008 | Han et al. |
| 2011/0008335 A1 | 1/2011 | Velardi et al. |
| 2012/0315269 A1 | 12/2012 | Klechevsky et al. |
| 2013/0095097 A1 | 4/2013 | Blankenship et al. |
| 2013/0142813 A1 | 6/2013 | Hirabayashi et al. |
| 2013/0273078 A1 | 10/2013 | Rolland et al. |
| 2013/0280265 A1 | 10/2013 | Rolland et al. |

FOREIGN PATENT DOCUMENTS

| WO | 2005/009465 A1 | 2/2005 |
| WO | 2009/091601 A1 | 7/2009 |

(Continued)

OTHER PUBLICATIONS

Monsivais-Urenda et al., "Analysis of expression and function of the inhibitory receptor ILT2 (CD85j/LILRB1/LIR-1) in peripheral blood mononuclear cells from patients with systemic lupus erythematosus (SLE)", Journal of Autoimmunity, Sep.-Nov. 2007, pp. 97-105, vol. 29, Issues 2-3, Elsevier, New York City, NY.

(Continued)

*Primary Examiner* — Bao Q Li
(74) *Attorney, Agent, or Firm* — Pamela J. Sherwood; Bozicevic, Field & Francis LLP

(57) ABSTRACT

Methods and compositions are provided for inducing phagocytosis of a target cell, treating an individual having cancer, treating an individual having an intracellular pathogen infection (e.g., a chronic infection), and/or reducing the number of inflicted cells (e.g., cancer cells, cells infected with an intracellular pathogen, etc.) in an individual. Methods and compositions are also provided for predicting whether an individual is resistant (or susceptible) to treatment with an anti-CD47/SIRPA agent. In some cases, the subject methods and compositions include an anti-MHC Class I/LILRB1 agent. In some cases, the subject methods and compositions include an anti-MHC Class I/LILRB1 agent and an anti-CD47/SIRPA agent (e.g., co-administration of an anti-MHC Class I/LILRB1 agent and an anti-CD47/SIRPA agent). Kits are also provided for practicing the methods of the disclosure.

17 Claims, 22 Drawing Sheets

Specification includes a Sequence Listing.

(56) References Cited

FOREIGN PATENT DOCUMENTS

WO  2013/181438 A2  12/2013
WO  2014/164640 A1  10/2014

OTHER PUBLICATIONS

Saverino et al., "The CD85/LIR-1/ILT2 Inhibitory Receptor Is Expressed by All Human T Lymphocytes and Down-Regulates Their Functions", The Journal of Immunology, Oct. 1, 2000, pp. 3742-3755, vol. 165, No. 7, The American Association of Immunologists, Rockville, MD.

Moysey et al., "High affinity soluble ILT2 receptor: a potent inhibitor of CD8+ T cell activation", Protein & Cell, Dec. 2010, pp. 1118-1127, vol. 1, No. 12, Springer, Berlin, Germany.

Steevels et al., "Immune inhibitory receptors: Essential regulators of phagocyte function", European Journal of Immunology, Mar. 1, 2011, pp. 575-587, vol. 41, Issue 3, Wiley, Hoboken, NJ.

Tseng et al., "Anti-CD47 antibody-mediated phagocytosis of cancer by macrophages primes an effective antitumor T-cell response", Proceedings National Academy of Sciences PNAS, Jul. 2, 2013, pp. 11103-11108, vol. 110, No. 27, National Academy of Sciences, Washington, D.C.

Barkal et al., "Engagement of MHC class I by the inhibitory receptor LILRB1 suppresses macrophages and is a target of cancer immunotherapy", Nature Immunology, Nov. 27, 2017, pp. 76-84, vol. 19, No. 1, Macmillan Publishers Limited, Basingstoke, United Kingdom.

Unanue, "Perspectives on anti-CD47 antibody treatment for experimental cancer", Proc Nail Acad Sci USA, Jul. 2, 2013, pp. 10886-10887, vol. 110, No. 27, PNAS, Washington, DC.

UniProtKB entry D5GFB2, Jun. 15, 2010, retrieved on Feb. 22, 2016 from http://www.uniprot.org/uniprot/D5GFB2.

Rouas-Freiss et al., "The Dual Role of HLA-G in Cancer", J Immunol Res. Mar. 31, 2014, pp. 1-10, vol. 2014, Hindawi Limited, London, United Kingdom.

Berg et. al., "The major SHP-1-binding, tyrosine-phosphorylated protein in macrophages is a member of the KIR/LIR family and an SHP-1 substrate", Oncogene, 1998, pp. 2535-2541, 17, Nature Publishing Group, New York, NY.

Munitz et al., "Paired immunoglobulin-like Receptor B (PIR-B) Negatively Regulates Macrophage Activation in Experimental Colitis", Gastroenterology, Aug. 2010, pp. 530-541, 139(2), Elsevier Inc., Amsterdam, Netherlands.

Nakayama et al., "Inhibitory Receptor Paired Ig-like Receptor B Is Exploited by *Staphylococcus aureus* for Virulence", J Immunol., Dec. 15, 2012, pp. 5903-5911,189(12), The American Association of Immunologists, Inc.,Rockville, MD.

Takai, "Paired immunoglobulin-like receptors and their MHC class I recognition", Immunology, Apr. 27, 2005, pp. 433-440, 115(4), Wiley, Hoboken, NJ.

Petroff et al., "Decidual macrophages are potentially susceptible to inhibition by class Ia and class Ib HLA molecules" J Reprod Immunol, Jul.-Aug. 2002, pp. 3-17, vol. 56, Issues 1-2, Elsevier, Amsterdam, Netherlands.

Takai, "A Novel Recognition System for MHC Class I Molecules Constituted by PIR", Adv Immunol, 2005, p. 161-192, vol. 88, Elsevier, Amsterdam, Netherlands.

Davidson et al., "The AP-1 transcription factor JunD activates the leukocyte immunoglobulin-like receptor 1 distal promoter", International Immunology, Sep. 13, 2013, pp. 21-33, vol. 26. No. 1, The Japanese Society for Immunology, Tokyo, Japan.

Liu et al., "Specific growth inhibition of ErbB2-expressing human breast cancer cells by genetically modified NK-92 cells", Oncology Reports, Oct. 14, 2014, pp. 95-102, Spandidos Publications, Athens, Greece.

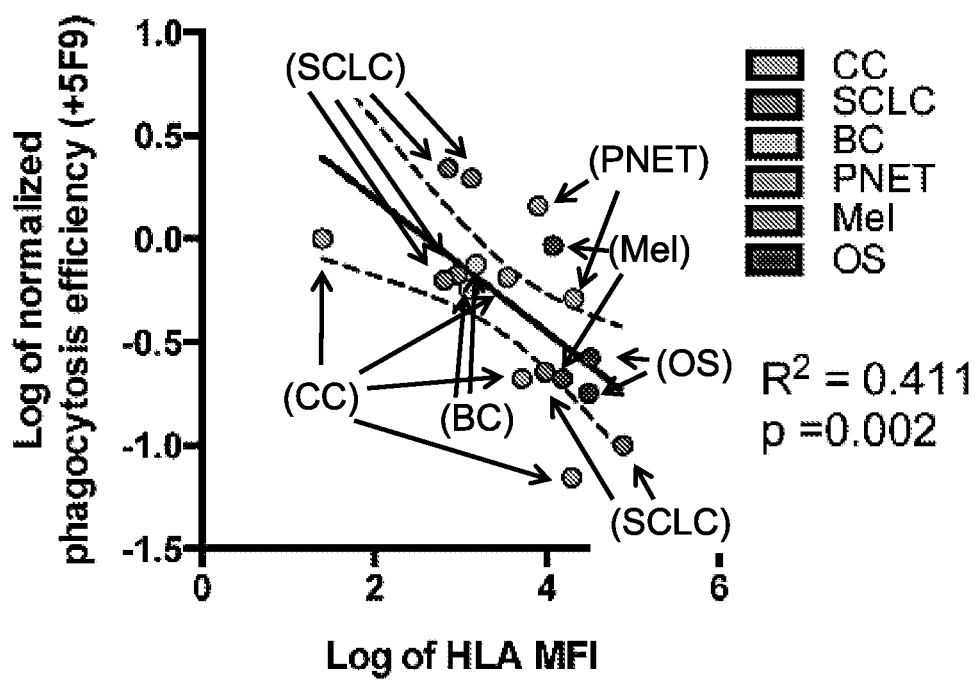

Fig. 16

| | Mean Diff. | 95% CI of diff. | Significant? | Summary | Individual P Value |
|---|---|---|---|---|---|
| Day 0 | | | | | |
| KWNO1/delB2M+PBS vs. KWNO1/hmcB2M+PBS | 0 | -41.32 to 41.32 | No | ns | > 0.9999 |
| KWNO1/delB2M+PBS vs. KWNO1/delB2M+5F9 | 0 | -41.32 to 41.32 | No | ns | > 0.9999 |
| KWNO1/delB2M+PBS vs. KWNO1/hmcB2M+5F9 | 0 | -41.32 to 41.32 | No | ns | > 0.9999 |
| KWNO1/hmcB2M+PBS vs. KWNO1/delB2M+5F9 | 0 | -41.32 to 41.32 | No | ns | > 0.9999 |
| KWNO1/hmcB2M+PBS vs. KWNO1/hmcB2M+5F9 | 0 | -41.32 to 41.32 | No | ns | > 0.9999 |
| KWNO1/delB2M+5F9 vs. KWNO1/hmcB2M+5F9 | 0 | -41.32 to 41.32 | No | ns | > 0.9999 |
| Day 7 | | | | | |
| KWNO1/delB2M+PBS vs. KWNO1/hmcB2M+PBS | 0 | -41.32 to 41.32 | No | ns | > 0.9999 |
| KWNO1/delB2M+PBS vs. KWNO1/delB2M+5F9 | 0 | -41.32 to 41.32 | No | ns | > 0.9999 |
| KWNO1/delB2M+PBS vs. KWNO1/hmcB2M+5F9 | 0 | -41.32 to 41.32 | No | ns | > 0.9999 |
| KWNO1/hmcB2M+PBS vs. KWNO1/delB2M+5F9 | 0 | -41.32 to 41.32 | No | ns | > 0.9999 |
| KWNO1/hmcB2M+PBS vs. KWNO1/hmcB2M+5F9 | 0 | -41.32 to 41.32 | No | ns | > 0.9999 |
| KWNO1/delB2M+5F9 vs. KWNO1/hmcB2M+5F9 | 0 | -41.32 to 41.32 | No | ns | > 0.9999 |
| Day 14 | | | | | |
| KWNO1/delB2M+PBS vs. KWNO1/hmcB2M+PBS | -6.363 | -47.68 to 34.96 | No | ns | 0.7622 |
| KWNO1/delB2M+PBS vs. KWNO1/delB2M+5F9 | -1.348 | -42.67 to 39.97 | No | ns | 0.9489 |
| KWNO1/delB2M+PBS vs. KWNO1/hmcB2M+5F9 | -4.423 | -45.74 to 36.90 | No | ns | 0.8334 |
| KWNO1/hmcB2M+PBS vs. KWNO1/delB2M+5F9 | 5.015 | -36.31 to 46.33 | No | ns | 0.8115 |
| KWNO1/hmcB2M+PBS vs. KWNO1/hmcB2M+5F9 | 1.94 | -39.38 to 43.26 | No | ns | 0.9265 |
| KWNO1/delB2M+5F9 vs. KWNO1/hmcB2M+5F9 | -3.075 | -44.39 to 38.25 | No | ns | 0.8838 |
| Day 21 | | | | | |
| KWNO1/delB2M+PBS vs. KWNO1/hmcB2M+PBS | -5.453 | -46.77 to 35.87 | No | ns | 0.7954 |
| KWNO1/delB2M+PBS vs. KWNO1/delB2M+5F9 | 6.563 | -34.76 to 47.88 | No | ns | 0.755 |
| KWNO1/delB2M+PBS vs. KWNO1/hmcB2M+5F9 | -0.42 | -41.74 to 40.90 | No | ns | 0.9841 |
| KWNO1/hmcB2M+PBS vs. KWNO1/delB2M+5F9 | 12.02 | -29.30 to 53.34 | No | ns | 0.5678 |
| KWNO1/hmcB2M+PBS vs. KWNO1/hmcB2M+5F9 | 5.033 | -36.29 to 46.35 | No | ns | 0.8109 |
| KWNO1/delB2M+5F9 vs. KWNO1/hmcB2M+5F9 | -6.983 | -48.30 to 34.34 | No | ns | 0.7399 |
| Day 28 | | | | | |
| KWNO1/delB2M+PBS vs. KWNO1/hmcB2M+PBS | -14.77 | -56.09 to 26.55 | No | ns | 0.4825 |

Fig. 16 (Cont.)

| | | | | | |
|---|---|---|---|---|---|
| KWNO1/delB2M+PBS vs. KWNO1/delB2M+5F9 | 12.38 | -28.94 to 53.70 | No | ns | 0.5562 |
| KWNO1/delB2M+PBS vs. KWNO1/hmcB2M+5F9 | 5.105 | -36.21 to 46.43 | No | ns | 0.8082 |
| KWNO1/hmcB2M+PBS vs. KWNO1/delB2M+5F9 | 27.15 | -14.17 to 68.47 | No | ns | 0.1972 |
| KWNO1/hmcB2M+PBS vs. KWNO1/hmcB2M+5F9 | 19.88 | -21.44 to 61.20 | No | ns | 0.3448 |
| KWNO1/delB2M+5F9 vs. KWNO1/hmcB2M+5F9 | 7.273 | -48.59 to 34.05 | No | ns | 0.7295 |
| Day 35 | | | | | |
| KWNO1/delB2M+PBS vs. KWNO1/hmcB2M+PBS | 4.379 | -45.70 to 36.94 | No | ns | 0.8351 |
| KWNO1/delB2M+PBS vs. KWNO1/delB2M+5F9 | 56.06 | 14.74 to 97.38 | Yes | ** | 0.008 |
| KWNO1/delB2M+PBS vs. KWNO1/hmcB2M+5F9 | 9.509 | -31.81 to 50.83 | No | ns | 0.6512 |
| KWNO1/hmcB2M+PBS vs. KWNO1/delB2M+5F9 | 60.44 | 19.12 to 101.8 | Yes | ** | 0.0042 |
| KWNO1/hmcB2M+PBS vs. KWNO1/hmcB2M+5F9 | 13.89 | -27.43 to 55.21 | No | ns | 0.5091 |
| KWNO1/delB2M+5F9 vs. KWNO1/hmcB2M+5F9 | 46.55 | -87.87 to -5.233 | Yes | * | 0.0273 |
| Day 42 | | | | | |
| KWNO1/delB2M+PBS vs. KWNO1/hmcB2M+PBS | 18.77 | -22.55 to 60.09 | No | ns | 0.3723 |
| KWNO1/delB2M+PBS vs. KWNO1/delB2M+5F9 | 114.1 | 72.76 to 155.4 | Yes | **** | < 0.0001 |
| KWNO1/delB2M+PBS vs. KWNO1/hmcB2M+5F9 | 67.87 | 26.55 to 109.2 | Yes | ** | 0.0013 |
| KWNO1/hmcB2M+PBS vs. KWNO1/delB2M+5F9 | 95.31 | 53.99 to 136.6 | Yes | **** | < 0.0001 |
| KWNO1/hmcB2M+PBS vs. KWNO1/hmcB2M+5F9 | 49.1 | 7.778 to 90.42 | Yes | * | 0.02 |
| KWNO1/delB2M+5F9 vs. KWNO1/hmcB2M+5F9 | 46.21 | -87.53 to -4.889 | Yes | * | 0.0285 |

COMPOSITIONS AND METHODS FOR INDUCING PHAGOCYTOSIS OF MHC CLASS I POSITIVE CELLS AND COUNTERING ANTI-CD47/SIRPA RESISTANCE

CROSS-REFERENCE

This application claims the benefit of U.S. Provisional Patent Application No. 62/068,531 filed Oct. 24, 2014, which application is incorporated herein by reference in its entirety.

GOVERNMENT SUPPORT

This invention was made with Government support under contracts CA086017 and CA139490 awarded by the National Institutes of Health. The Government has certain rights in the invention.

INTRODUCTION

Programmed cell death (PCD) and phagocytic cell removal are common ways that an organism responds in order to remove damaged, precancerous, or infected cells. Cells that survive this organismal response (e.g., cancerous cells, chronically infected cells, etc.) have devised ways to evade PCD and phagocytic cell removal. For example, growing tumors, and cells harboring an infection, are under constant pressure from the host immune system, and evasion of immunosurveillance is critical for the progression of cancer and chronic infection in patients. Therapeutic agents that disrupt this escape, either by directly stimulating the immune system to attack tumor cells and/or infected cells, or by blocking immunosuppressive signals expressed by tumor cells and/or infected cells, comprise a promising new category of drugs.

If property engaged, effector cells of both the innate and adaptive immune systems possess the ability to attack cancer cells and/or infected cells. For example, tumor-binding monoclonal antibodies can induce this attack, and efficacy is in part dependent on the antibody's ability to stimulate antibody-dependent cellular phagocytosis (ADCP) by macrophages. However, CD47, a "don't eat me" signal, is constitutively upregulated on a wide variety of diseased cells, cancer cells, and infected cells, allowing these cells to evade phagocytosis. Although binding of an anti-tumor antibody to tumor cells is sufficient to engage macrophage Fc receptors and thereby stimulate some degree of tumor cell phagocytosis, the potency of this response is strongly limited by the tumor's expression of CD47.

Anti-CD47/SIRPA agents that block the interaction between CD47 on one cell (e.g., a cancer cell, an infected cell, etc.) and SIRPA on another cell (e.g., a phagocytic cell) counteract the increase of CD47 expression and facilitate the phagocytosis of the cancer cell and/or the infected cell. For example, CD47 blocking antibodies simultaneously disrupt the CD47/SIRPA interaction and opsonize tumor cells to which they bind, powerfully promoting macrophage phagocytosis (FIG. 1A). Anti-CD47/SIRPA agents can be used to treat and/or protect against a wide variety of conditions/disorders.

However, some cancer cells and/or infected cells are resistant to treatment with anti-CD47/SIRPA agents. The present disclosure provides compositions and methods for predicting whether a cancer (e.g., predicting whether an individual having cancer) will be responsive to anti-CD47 treatment. This disclosure further provides compositions and methods for treating a cancer and/or an infection that is resistant to treatment with anti-CD47/SIRPA agents. For example, this disclosure provides compositions and methods for reducing the resistance to treatment (with an anti-CD47/SIRPA agent) of a cancer cell and/or an infected cell.

Publications

Borges et al., 1997, *Journal of Immunology* 159, 5192-5196; Fanger et al., 1998, *European Journal of Immunology* 28, 3423-3434; Willcox et al., 2003, *Nature immunology* 4, 913-919; Cheng, H. et al., 2011, *The Journal of biological chemistry* 286, 18013-18025, doi:10.1074/jbc.M111.221028.

SUMMARY

Methods and compositions are provided for inducing phagocytosis of a target cell, treating an individual having cancer, treating an individual having an intracellular pathogen infection (e.g., a chronic infection), and/or reducing the number of inflicted cells (e.g., cancer cells, cells infected with an intracellular pathogen, etc.) in an individual. Methods and compositions are also provided for predicting whether an individual is resistant (or susceptible) to treatment with an anti-CD47/SIRPA agent. In some cases, the subject methods and compositions include an anti-MHC Class I/LILRB1 agent. In some cases, the subject methods and compositions include an anti-MHC Class I/LILRB1 agent and an anti-CD47/SIRPA agent (e.g., co-administration of an anti-MHC Class I/LILRB1 agent and an anti-CD47/SIRPA agent). Kits are also provided for practicing the methods of the disclosure.

In some embodiments, a subject composition (e.g., for increasing phagocytosis of a target cell) includes: (a) an anti-MHC ClassI/LILRB1 agent (e.g., an MHC Class I binding agent such as an anti-MHC Class I antibody or an LILRB1 peptide; an LILRB1 binding agent such as an anti-LILRB1 antibody or a soluble MHC class I complex that binds to LILRB1; and the like); and (b) at least one of: (i) an agent that opsonizes the target cell, and (ii) an anti-CD47/SIRPA agent. In some cases, the anti-MHC ClassI/LILRB1 agent specifically binds major histocompatibility complex (MHC) Class I. In some cases, the anti-MHC ClassI/LILRB1 agent is an antibody that specifically binds classical MHC Class I, where the classical MHC Class I lacks HLA-G and comprises at least one of HLA-A, HLA-B, and HLA-C. In some cases, the anti-MHC ClassI/LILRB1 agent is a soluble leukocyte immunoglobulin-like receptor subfamily B member 1 (LILRB1) peptide. In some cases, the anti-MHC ClassI/LILRB1 agent specifically binds leukocyte immunoglobulin-like receptor subfamily B member 1 (LILRB1) and does not activate signaling through LILRB1 upon binding. In some cases, the anti-MHC ClassI/LILRB1 agent is an anti-LILRB1 antibody. In some cases, the composition also includes an anti-CD47/SIRPA agent. In some cases, the agent that opsonizes the target cell is an antibody other than an anti-CD47 antibody. In some cases, the composition includes an anti-CD47/SIRPA agent and an agent that opsonizes the target cell.

In some embodiments, a subject kit (e.g., for increasing phagocytosis of a target cell) includes: (a) an anti-MHC ClassI/LILRB1 agent (e.g., an MHC Class I binding agent such as an anti-MHC Class I antibody or an LILRB1 peptide; an LILRB1 binding agent such as an anti-LILRB1 antibody or a soluble MHC class I complex that binds to LILRB1; and the like); and (b) an anti-CD47/SIRPA agent and/or an agent that opsonizes the target cell (e.g., where (a) and (b) are in separate containers). In some cases, at least one of (a) and (b) is present as a therapeutic formulation.

In some embodiments, a subject method is a method of inducing phagocytosis of a target cell, and the method includes: contacting a target cell with a macrophage in the presence of an anti-MHC ClassI/LILRB1 agent (e.g., an MHC Class I binding agent such as an anti-MHC Class I antibody or an LILRB1 peptide; an LILRB1 binding agent such as an anti-LILRB1 antibody or a soluble MHC class I complex that binds to LILRB1; and the like) and at least one of: an anti-CD47/SIRPA agent and an agent that opsonizes the target cell, for a period of time sufficient to induce phagocytosis of the target cell by the macrophage. In some cases, the target cell is a cancer cell. In some cases, the target cell is a cell infected with an intracellular pathogen. In some cases, the target cell is a cancer cell of an individual having cancer. In some cases, the contacting is in vitro or ex vivo. In some cases, the contacting is in vivo. In some cases, the anti-MHC ClassI/LILRB1 agent specifically binds major histocompatibility complex (MHC) Class I. In some cases, the anti-MHC ClassI/LILRB1 agent specifically binds classical MHC Class I, wherein said classical MHC Class I lacks HLA-G and comprises at least one of HLA-A, HLA-B, and HLA-C. In some cases, the anti-MHC ClassI/LILRB1 agent is an antibody or a binding fragment thereof. In some cases, the anti-MHC ClassI/LILRB1 agent is a soluble leukocyte immunoglobulin-like receptor subfamily B member 1 (LILRB1) polypeptide. In some cases, the anti-MHC ClassI/LILRB1 agent specifically binds leukocyte immunoglobulin-like receptor subfamily B member 1 (LILRB1) and does not activate signaling through LILRB1 upon binding. In some cases, the anti-MHC ClassI/LILRB1 agent is an anti-LILRB1 antibody or a binding fragment thereof. In some cases, the contacting is in the presence of an anti-MHC ClassI/LILRB1 agent and an anti-CD47/SIRPA agent.

In some embodiments, a subject method is a method of treating an individual having cancer (and/or having an intracellular pathogen infection) where the method includes administering to the individual: (a) an anti-MHC ClassI/LILRB1 agent (e.g., an MHC Class I binding agent such as an anti-MHC Class I antibody or an LILRB1 peptide; an LILRB1 binding agent such as an anti-LILRB1 antibody or a soluble MHC class I complex that binds to LILRB1; and the like); and (b) at least one of: (i) an anti-CD47/SIRPA agent, and (ii) an agent that opsonizes a target cell of the individual, where the target cell is a cancer cell (and/or a cell harboring an intracellular pathogen), in amounts effective for reducing the number of cancer cells (and/or cells harboring the intracellular pathogen) in the individual. In some cases, (a) and (b) are administered simultaneously. In some cases, (a) and (b) are not administered simultaneously. In some cases, the method includes, prior to the administering step: measuring the expression level of Major Histocompatibility Complex (MHC) Class I in a biological sample of the individual, where the biological sample includes a cancer cell (and/or a cell harboring an intracellular pathogen); and providing a prediction, based on the result of the measuring step, that the individual is resistant to treatment with an anti-CD47/SIRPA agent.

In some embodiments, a subject method is a method of predicting whether an individual is resistant or susceptible to treatment with an anti-CD47/SIRPA agent, where the method includes: (a) measuring the expression level of Major Histocompatibility Complex (MHC) Class I in a biological sample of the individual, where the biological sample includes a cancer cell (and/or a cell harboring an intracellular pathogen), to produce a measured test value; (b) comparing the measured test value to a control value; and (c) providing a prediction, based on the comparing step, as to whether the individual is resistant or susceptible to treatment with an anti-CD47/SIRPA agent. In some cases, the measuring step includes an antibody-based method. In some cases, the antibody-based method includes flow cytometry. In some cases, the MHC Class I is classical MHC Class I that lacks HLA-G and comprises HLA-A, HLA-B, and/or HLAC. In some cases, the control value is the expression level of MHC Class I from a cell or population of cells known to exhibit a phenotype of resistance to treatment with an anti-CD47/SIRPA agent. In some cases, the control value is the background value of the measuring step. In some cases, the method includes a step of determining that the cancer cell (and/or the cell harboring an intracellular pathogen) is positive for MHC Class I, and providing a prediction that the individual is resistant treatment with an anti-CD47/SIRPA agent. In some cases, the method includes: (a) providing a prediction that the individual is resistant to treatment with an anti-CD47/SIRPA agent, and (b) administering to the individual an anti-MHC ClassI/LILRB1 agent and an anti-CD47/SIRPA agent (e.g., an MHC Class I binding agent such as an anti-MHC Class I antibody or an LILRB1 peptide; an LILRB1 binding agent such as an anti-LILRB1 antibody or a soluble MHC class I complex that binds to LILRB1; and the like). In some cases, the providing a prediction step includes generating a report that includes at least one of: (i) the measured expression level of MHC Class I, (ii) the normalized measured expression level of MHC Class I, (iii) a prediction of resistance or susceptibility to an anti-CD47/SIRPA agent, and (iv) a recommended therapy based on the measured test value. In some cases, the report is displayed to an output device at a location remote to the computer. In some cases, a subject method includes a identifying/selecting a patient need of co-administration of an anti-MHC ClassI/LILRB1 agent and an anti-CD47/SIRPA agent.

Aspects of the disclosure include anti-MHC ClassI/LILRB1 agents. In some cases a subject anti-MHC ClassI/LILRB1 agent is an anti-LLRB1 antibody (e.g., humanized, e.g., IgG4 isotype humanized antibody). In some cases a subject anti-MHC ClassI/LILRB1 agent is an anti-MHC ClassI antibody (e.g., humanized, e.g., IgG4 isotype humanized antibody). In some cases a subject anti-MHC ClassI/LILRB1 agent is a polypeptide the includes the light chain CDR amino acid sequences set forth in SEQ ID NOs: 8-10 and the heavy chain CDR amino acid sequences set forth in SEQ ID NOs: 12-14. In some cases, the agent includes the light chain amino acid sequence set forth in SEQ ID NO: 7 and the heavy chain amino acid sequence set forth in SEQ ID NO: 11. In some cases, the agent is a humanized antibody or a Fab fragment. In some cases, the agent is present in a pharmaceutical composition. Aspects of the disclosure also includes preparation of a medicament (e.g., a medicament that includes a subject anti-MHC ClassI/LILRB1 agent, a medicament that includes a subject anti-MHC ClassI/LILRB1 agent and an anti-CD47/SIRPA agent, a medicament that includes a subject anti-MHC ClassI/LILRB1 agent and an antibody against a cancer antigen, a medicament that includes a subject anti-MHC ClassI/LILRB1 agent and an anti-CD47/SIRPA agent and an antibody against a cancer antigen, and the like). In some cases, an anti-MHC ClassI/LILRB1 agent (e.g., in any of the methods or compositions of the disclosure) is an antibody (e.g., anti-LLRB1 antibody, anti-MHC Class I antibody) and can be a humanized antibody, e.g., can be an IgG4 isotype humanized antibody.

BRIEF DESCRIPTION OF THE DRAWINGS

FIG. 1A-1C. Resistance to macrophage phagocytosis correlates with MHC Class I expression. (FIG. 1A) Cartoon schematic of signaling between macrophages and target cancer cells under untreated conditions (left) and treatment with anti-CD47 therapy (right). (FIG. 1B) FACS-based measurement of phagocytosis by donor-derived human macrophages against a panel of 18 cancer cell lines, including Colon Carcinoma (CC), Small Cell Lung Cancer (SCLC), Breast Carcinoma (BC), Pancreatic Neuroendocrine Tumor (PNET), Melanoma (Mel), and Osteosarcoma (OS) upon treatment with PBS or a humanized anti-CD47 antibody, Hu5F9-G4. All values were normalized to DLD1 as an index control. Error bars represent the standard deviation of assays with four independent donors for all lines, with the exception of H128, H1688, and SkBr3, for which they represent three independent donors. 12 of 18 lines show a significant increase ($p<0.05$; Student's two-sided t-test without multiple comparisons correction) in phagocytosis upon treatment with Hu5F9-G4. (FIG. 1C) Log-transformed scatterplot of normalized phagocytic efficiency upon treatment with the anti-CD47 antibody Hu5F9-G4 (Y axis) plotted against surface expression of HLA-A, B, C as measured by FACS analysis with the pan-HLA binding antibody W6/32 (X axis). Y values are log-transformed averages of values represented in FIG. 1A. There is a significant, inverse relationship between HLA-A, B, C expression and sensitivity to phagocytosis upon treatment with Hu5F9-G4 ($R^2=0.411$, $p=0.002$).

(FIG. 2A) Expression summary table (left) and FACS scatterplot (right) of CD47 and HLA-A, B, C expression levels (Y and X axes, respectively) for four genetically engineered sub-lines of KWNO1. (FIG. 2B) Expression summary table (left) and FACS scatterplot (right) of CD47 and HLA-A, B, C expression levels (Y and X axes, respectively) for four genetically engineered sub-lines of DLD1. (FIG. 2C) FACS-based measurement of phagocytosis by human macrophages co-cultured with parental KWNO1 (red) and a B2M-deleted sub-line, KWNO1-ΔB2M (black), upon treatment with PBS or the anti-CD47 antibody Hu5F9-G4. Values are normalized to the maximum level of phagocytosis in each independent replicate experiment. Error bars represent the standard deviation of experiments with eight independent macrophage donors.  $p<0.01$, * $p<0.001$, 2-way ANOVA with multiple comparisons correction. (FIG. 2D) FACS-based measurement of phagocytosis by human macrophages co-cultured with parental DLD1 (black) and an MHC-reconstituted transgenic sub-line, DLD1-Tg(B2M) (red), upon treatment with PBS or the anti-CD47 antibody Hu5F9-G4. Values are normalized to the maximum level of phagocytosis in each independent replicate experiment. Error bars represent the standard deviation of experiments with eight independent macrophage donors. n.s., not significant. *** $p<0.001$, 2-way ANOVA with multiple comparisons correction. (FIG. 2E) FACS-based measurement of phagocytosis by human macrophages co-cultured with KWNO1 genetic variants. Values are normalized to the maximum level of phagocytosis in each independent replicate experiment. Anti-EpCam antibody is clone 1B7. Error bars represent the standard deviation of experiments from eight independent macrophage donors. n.s., not significant. * $p<0.05$,  $p<0.01$, * $p<0.001$, 2-way ANOVA with multiple comparisons correction. (FIG. 2F) FACS-based measurement of phagocytosis by human macrophages co-cultured with DLD1 genetic variants. Values are normalized to the maximum level of phagocytosis in each independent replicate experiment. Anti-EGFR is the clinical antibody cetuximab. Error bars represent the standard deviation of experiments from eight independent macrophage donors. n.s., not significant. * $p<0.05$,  $p<0.01$, * $p<0.001$, 2-way ANOVA with multiple comparisons correction. (FIG. 2G) FACS-based measurement of phagocytosis by donor-derived macrophages of the MHC− line DLD1 (left panel, black), and the MHC+ lines U2OS, SAOS2, SKMel3, NCI-H196, HCT116, and KWNO1 (right panel, gray) upon treatment with PBS; a fragment of antigen binding (Fab) generated via proteolytic cleavage of the pan-HLA antibody W6/32; the anti-CD47 antibody Hu5F9-G4; or a combination of the W6/32 Fab and Hu5F9-G4. Values are normalized to the maximum level of phagocytosis in each independent replicate experiment. Error bars represent the standard deviation of experiments with four independent macrophage donors. n.s., not significant. * $p<0.05$, Student's t-test without multiple comparisons correction.

(FIG. 3A) Representative histogram plots from FACS analysis of LILRB1 and LILRB2 expression in primary human CD14+ peripheral blood monocytes (left), and day 7 ex vivo cultured macrophages derived from the same donor (right). IgG control is indicated in red. Specific staining is indicated in blue. (FIG. 3B) LILRB1 and LILRB2 expression levels, as measured by mean fluorescence intensity (MFI, left panel) or percent positive cells (right panel), in 4 pairs of primary monocytes (blue circle) and ex vivo cultured macrophages from the same donors (red triangle). n.s., not significant.  $p<0.001$, 2-way ANOVA with multiple comparisons correction. (FIG. 3C) FACS-based measurement of phagocytosis by donor-derived macrophages of parental KWNO1 (red) and the MHC-negative sub-line KWNO1-ΔB2M (black) upon treatment with PBS, the anti-CD47 antibody Hu5F9-G4, a fragment of antigen binding (Fab) generated by proteolytic cleavage of the pan-HLA antibody W6/32, the anti-LILRB1 blocking antibody GHI/75, or the anti-LILRB2 blocking antibody 27D6. Values are normalized to the highest level of phagocytosis observed in a given experimental replicate. Error bars represent the standard deviation of assays performed with eight independent macrophage donors. n.s., not significant. * $p<0.001$, 2-way ANOVA with multiple comparisons correction.

(FIG. 4A) The crystal structure of the LILRB1:B2M:HLA-A2 complex, illustrating differences between human and mouse sequences. LILRB1 (magenta) makes extensive contact with residues of B2M (blue) but only limited contact with HLA-A2 (gray). Inset: residues that differ between human and mouse B2M, and that are located within 5 angstroms of LILRB1 are highlighted in orange. These residues were mutated, as indicated, to form a human-mouse chimeric B2M (hmcB2M). Images were generated using MacPyMol from published structure data IP7Q (Fanger et al, European Journal of Immunology 28, 3423-3434 (1998)). (FIG. 4B) FACS-based measurement of surface MHC class I expression, as measured by staining with the pan-HLA-A, B, C binding antibody W6/32. Parental DLD1 cells (left panel, black) are negative for surface MHC class I, but transgenic reconstitution with human B2M (DLD1-Tg(B2M), red), or a human-mouse-chimeric B2M (DLD1-Tg(hmcB2M), purple), both induce efficient surface MHC class I expression. Parental KWNO1 (right panel, red) are positive for MHC class I expression, which can be eliminated by CRISPR-mediated deletion of B2M (KWNO1-ΔB2M, black); transgenic expression of hmcB2M restores surface expression of MHC (KWNO1-Tg(hmcB2M)-ΔB2M, purple). (FIG. 4C) FACS-based measurement of phagocytosis by primary human donor-derived macrophages (Y axis) or NSG mouse-derived macrophages (X axis) co-cultured with parental DLD1 (black); B2M-deleted KWNO1 (KWNO1-ΔB2M, black); a DLD1 sub-line with transgenic expression of fully human B2M (red); parental KWNO1 (red); a DLD1 sub-line with transgenic expression of a human-mouse chimeric B2M (purple); or a KWNO1 sub-line with deleted B2M and transgenic expression of hmcB2M (KWNO1-Tg(hmcB2M)-ΔB2M, purple). Vertical error bars represent the standard deviation of experiments with eight independent biological donors, while horizontal error bars represent the standard deviation of eight experimental replicates across two experiments with independently derived NSG (NOD-SCID Il2rγ$^{-/-}$) mouse macrophages.

(FIG. 5A) Schematic of in vivo human macrophage xenograft system. Tumor cells and human macrophages were mixed on ice in a 1:2 ratio, and antibodies were added as indicated before subcutaneous injection into the flank of NSG mice. Tumor bioluminescence images from NSG (NOD-SCID Il2rγ$^{-/-}$) mice post-. (FIG. 5B) Tumor bioluminescence images from NSG (NOD-SCID Il2rγ$^{-/-}$) mice post-engraftment with primary ex vivo differentiated human macrophages and MHC+ tumor cells (KWNO1, left panel) or MHC− tumor cells (KWNO1-ΔB2M, right panel), treated with PBS, the anti-CD47 antibody Hu5F9-G4, the recombinant anti-LILRB1 antibody GHI75-G4, or a combination of the two antibodies. Five animals were evaluated per treatment group. Bioluminescence images are from day 7 (left panel) or day 14 (right panel). (FIG. 5C) Fluorescence microscopy of sections taken from mixed MHC+ and MHC− KWNO1 tumors injected subcutaneously into the flanks of NSG mice. Chimeric MHC+ cells are marked by GFP expression, while MHC− cells are marked by RFP expression. Mouse macrophages are visualized by F4/80 staining. A high degree of macrophage infiltration into the tumor is evident, and macrophages can be observed in the act of phagocytosis (white arrowhead). Scale bar represents 200 μM. (FIG. 5D) Schematic of in vivo experiment to assess sensitivity of MHC− and chimeric MHC+ cells to anti-CD47 agents. Equivalent numbers of cells were injected into the flanks of NSG mice, and allowed 14 days to engraft. Starting 14 days post-injection, the mice received once-weekly injections of either PBS or anti-CD47 antibody. (FIG. 5E) Tumor bioluminescence (total flux, photons/second) of MHC−(KWNO1-ΔB2M) and chimeric MHC+(KWNO1-Tg(hmcB2M)-ΔB2M) cells engrafted subcutaneously in the flanks of NSG mice, and starting at day 14 post-engraftment, treated once per week with either PBS or 10 mg/kg of the anti-CD47 antibody Hu5F9-G4. Lines represent the fold change in bioluminescent flux, normalized to the initial value as measured at day 7. Error bars represent standard error of the mean of 15 mice per group. Gray is MHC−(KWNO1-ΔB2M) treated with PBS; pink is chimeric MHC+(KWNO1-Tg(hmcB2M)-ΔB2M) treated with PBS; black is MHC−(KWNO1-ΔB2M) treated with Hu5F9-G4; purple is chimeric MHC+ (KWNO1-Tg(hmcB2M)-ΔB2M) treated with Hu5F9-G4.

* indicates p<0.05 versus vehicle treatment groups, ** indicates p<1e-4 versus vehicle treatment groups, 2-way ANOVA with Tukey's multiple comparisons correction; see Supplementary Table 1 for comprehensive statistical comparisons. Luminescence measurements were discontinued when mice had to be euthanized due to tumor growth.

Figure 6:
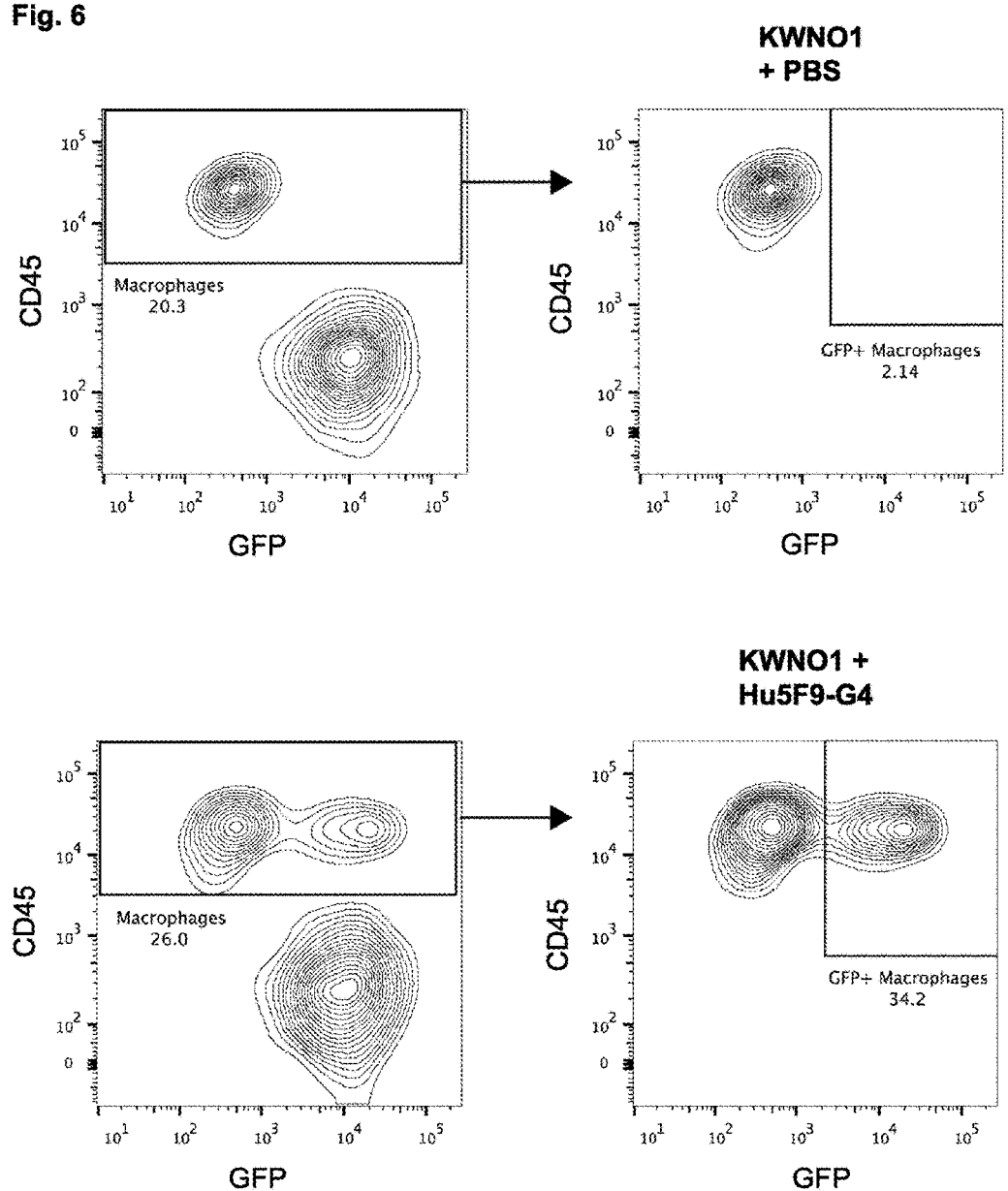

FIG. 6. Gating strategy of FACS-based in vitro phagocytosis assay. Our in vitro phagocytosis assay relies on differential labeling of target cancer cells (GFP+ CD45−) and human macrophages (GFP− CD45+) in order to identify macrophages that have successfully phagocytosed labeled target cells. Co-incubation with labeled target cells under PBS treatment conditions (top panels) leads to only minimal emergence of a GFP+ CD45+ population, which is measured as a percentage of the total macrophages. In contrast, treatment with a tumor-opsonizing antibody, especially under conditions of CD47 blockade, results in a clear emergence of a distinct GFP+ CD45+ population. We previously validated this assay by post-assay sorting and microscopy of the populations, which confirmed the gating strategy as successfully identifying macrophages that had phagocytosed one or more cancer cells (Weiskopf et al, *Science* 341, 88-91 (2013)).

Figure 7:
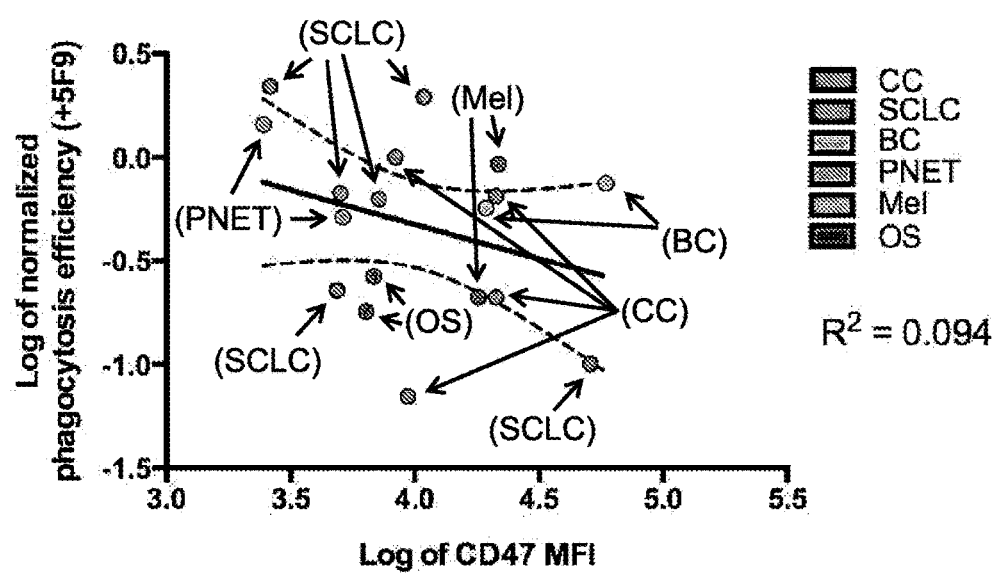

FIG. 7. CD47 expression does not correlate with sensitivity to Hu5F9-G4-induced phagocytosis. Log-transformed scatterplot of normalized phagocytic efficiency upon treatment with the anti-CD47 antibody Hu5F9-G4 (Y axis) plotted against surface expression of CD47, as measured by FACS analysis with the anti-human mouse monoclonal antibody B6H12 (X axis). There is no significant relationship between these two parameters, $R^2$=0.094, p=0.217.

Figure 8:
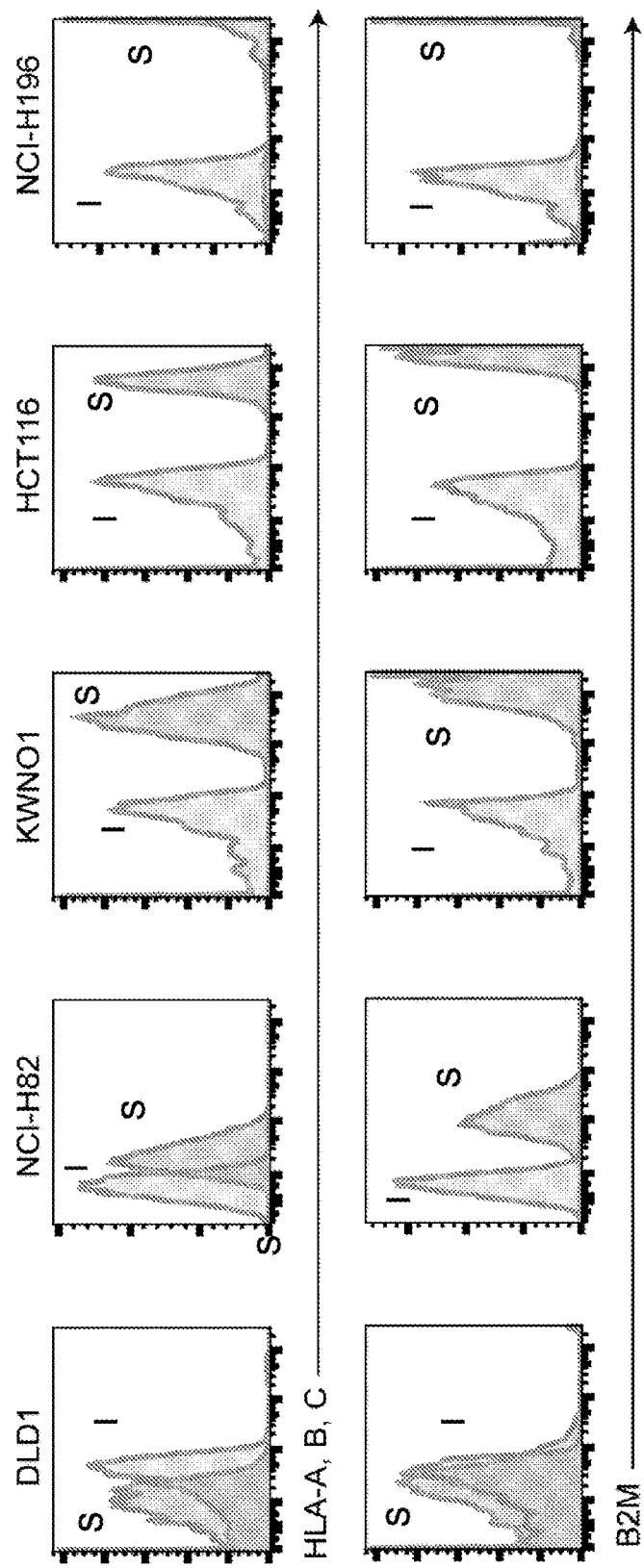

FIG. 8. MHC protein expression is high in phagocytosis-resistant cell lines. Histogram plots of HLA-A, B, C (top) and B2M expression (bottom) for two colon cancer cell lines: DLD1 (red) and HCT116 (magenta); two small cell lung cancer lines, NCI-H82 (blue), and NCI-H196 (purple); and a pancreatic neuroendocrine tumor KWNO1 (green), as measured by the BioLegend LegendScreen FACS-based antibody array system. Isotype control stain is indicated in blue, while specific stain is indicated in red.

Figure 9:
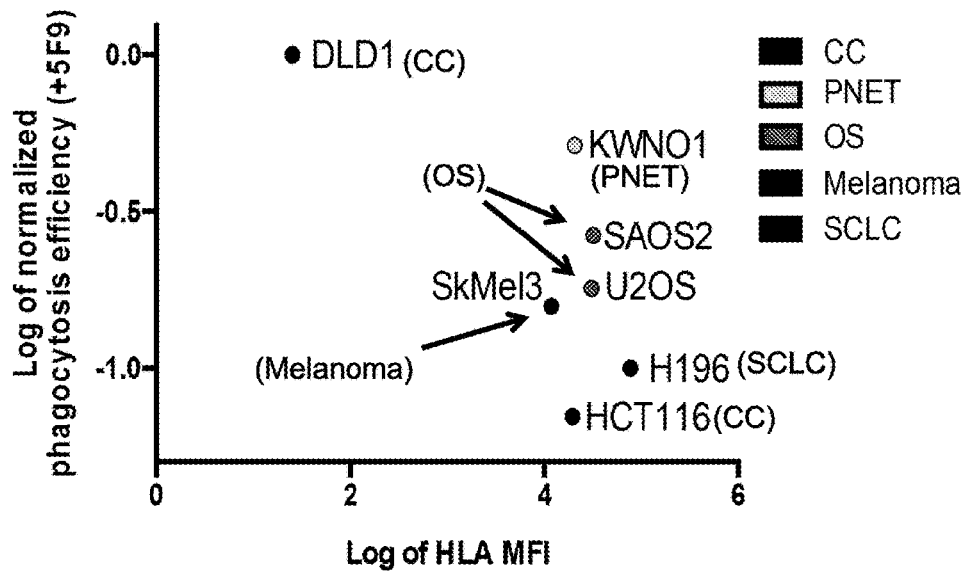

FIG. 9. HLA-A, B, C expression of phagocytosis-resistant cell lines. Log-scale scatterplot of phagocytic efficiency in a panel of cell lines upon treatment with the anti-CD47 antibody Hu5F9-G4 (Y axis), plotted against surface expression of HLA-A, B, C as measured by FACS analysis with a pan-HLA-A, B, C binding antibody (X axis). The data is a subset of that shown in FIG. 1B, in order to highlight the cell lines used for the experiment shown in FIG. 2G.

Figure 10:
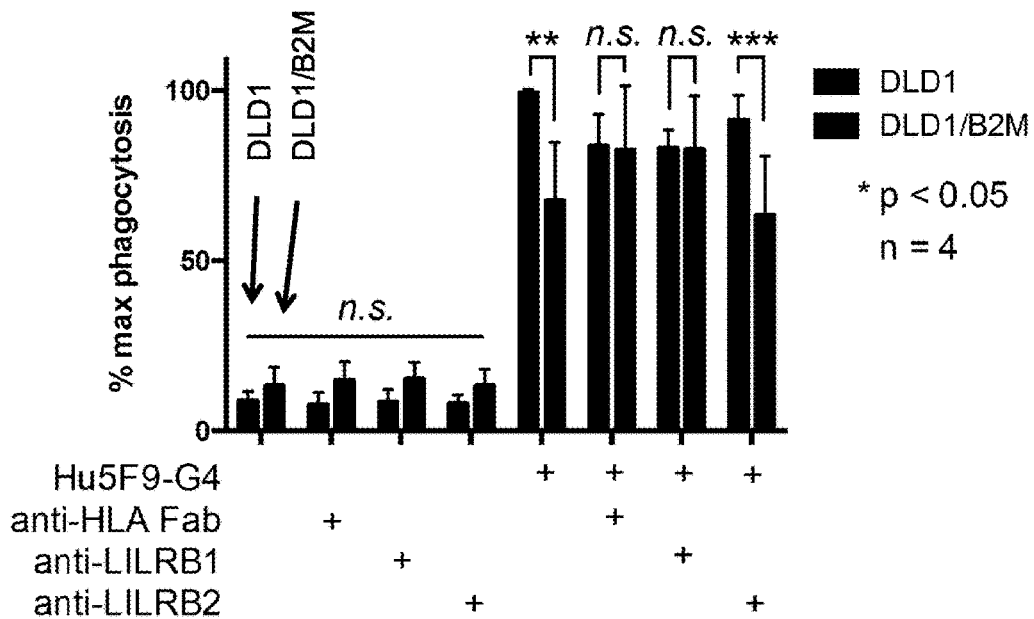

FIG. 10. LILRB1 antibody sensitizes MHC+ DLD1 cells to phagocytosis. FACS-based measurement of phagocytosis by donor-derived macrophages of parental DLD1 (black) and the human MHC-reconstituted transgenic sub-line DLD1-Tg(B2M) (red) upon treatment with PBS; the anti-CD47 antibody Hu5F9-G4; a fragment of antigen binding (Fab) generated by proteolytic cleavage of the pan-HLA antibody W6/32; the anti-LILRB1 antibody GHI/75; or the anti-LILRB2 antibody 27D6. Values are normalized to the highest level of phagocytosis observed in a given experimental replicate. Error bars represent the standard deviation of assays performed with eight independent macrophage donors. While DLD1-Tg(B2M) is significantly more resistant to Hu5F9-G4-induced phagocytosis than parental DLD1 (p<0.01, 2-way ANOVA with multiple comparisons correction), this significant difference is completely erased upon disruption of the MHC/LILRB1 signaling axis by either W6/32 fab or GHI/75. n.s., not significant.  p<0.01, * p<0.001, 2-way ANOVA with multiple comparisons correction.

Figure 11:
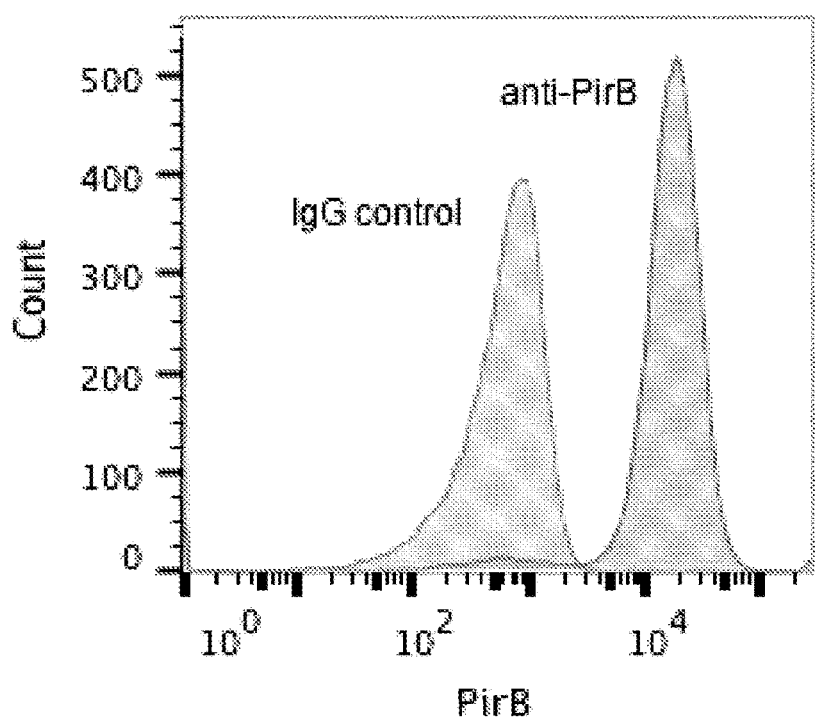

FIG. 11. Mouse macrophages express the LILRB family homolog PirB. FACS histogram of ex vivo-differentiated NSG macrophages stained with PE-labeled IgG control (red) or anti-PirA/B antibody 6C1.

Figure 12:
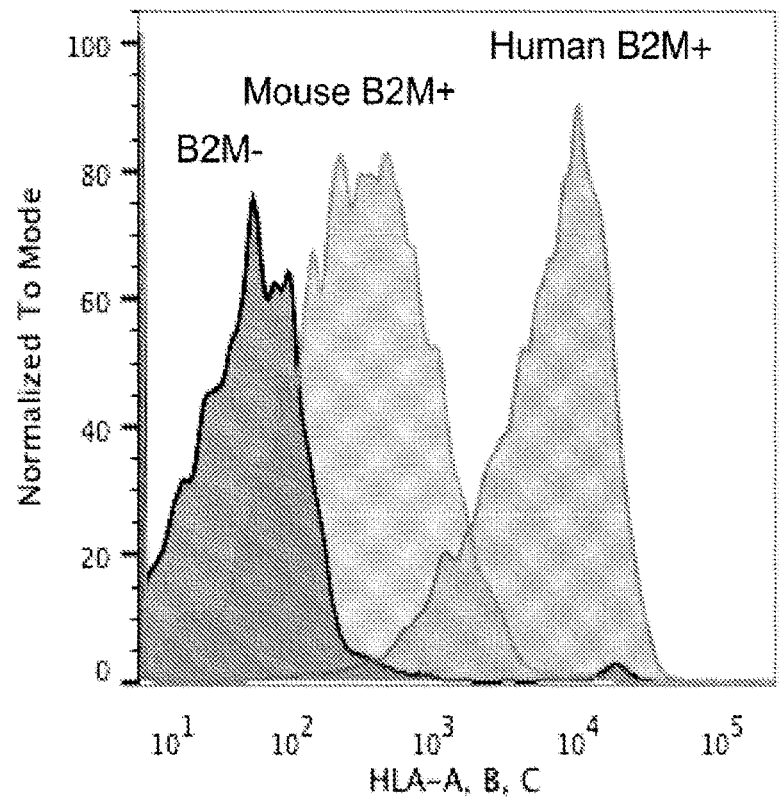

FIG. 12. Mouse B2m does not efficiently form stable MHC complexes with human HLA alpha chains. FACS histogram of parental DLD1 cells (black), DLD1 cells reconstituted with a human B2M transgene (red), or with a mouse B2m transgene (blue). While fully human B2M expression facilitates robust surface MHC expression, as detected by the pan-HLA antibody W6/32, expression of mouse B2m facilitates only low levels of surface MHC.

Figure 13:
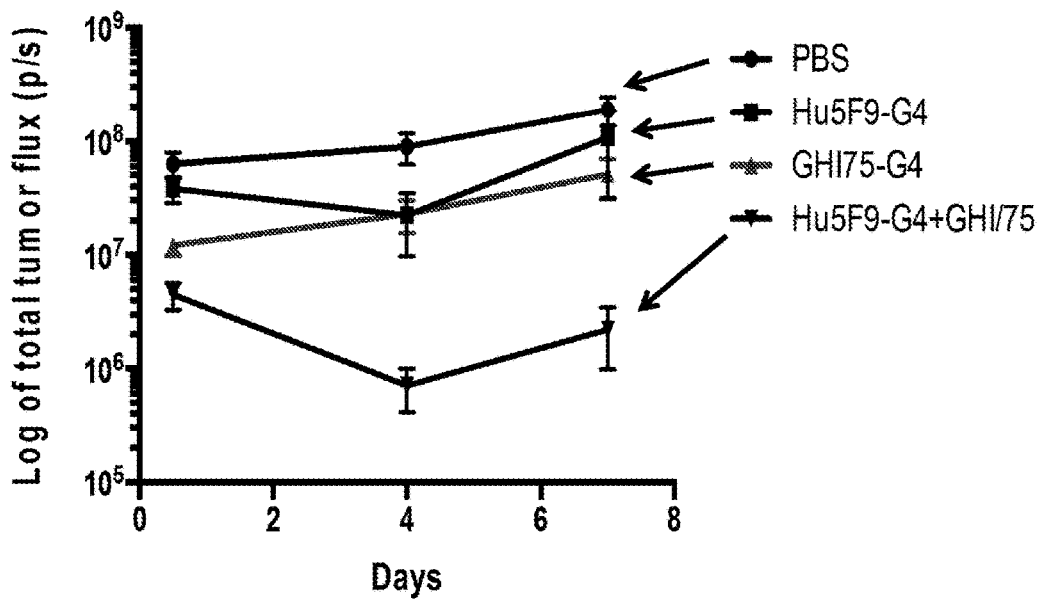

FIG. 13 Human macrophages continue to phagocytose cancer cells days after engraftment into NSG mice. KWNO1 cells were mixed with human macrophages and either PBS, the anti-CD47 antibody Hu5F9-G4, the recombinant anti-LILRB1 antibody GHI75-G4, or a combination of the two antibodies. These mixtures were then co-engrafted subcutaneously into NSG mice, and tumor luminescence was assessed at 12 hours, 4 days, and 7 days post-engraftment. By 12 hours post-engraftment, tumors treated with a combination of Hu5F9-G4 and GHI75-G4 exhibited a rapid decrease in luminescence as compared to other groups. The luminescence of these tumors continued to decline between 12 hours and 4 days post-engraftment, suggesting a continuation of macrophage phagocytosis of cancer cells. Error bars represent the standard deviation of five mice per group.

Figure 14:
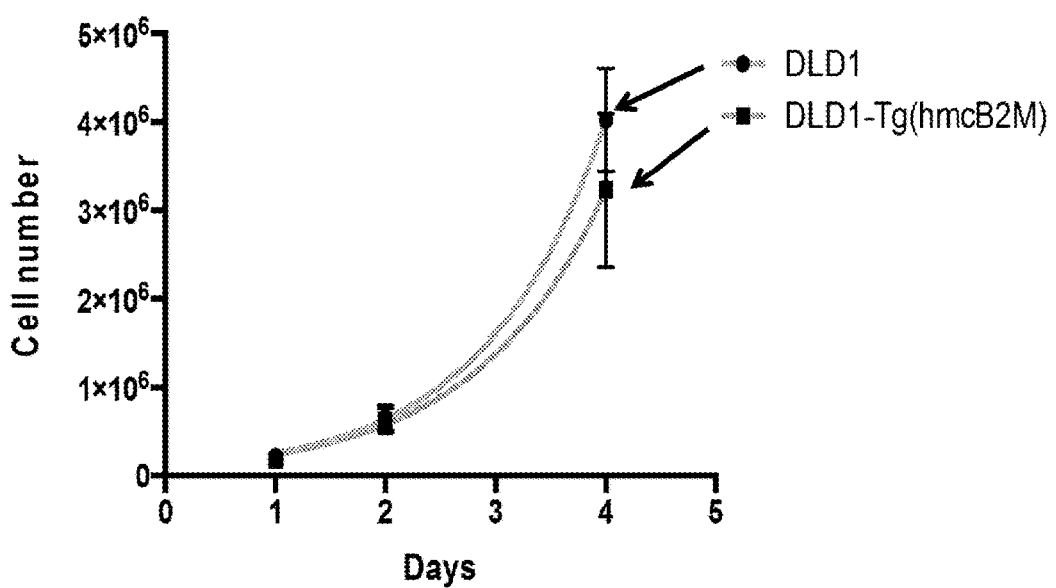

FIG. 14. MHC expression does not impact the in vitro growth kinetics of the DLD1 cell line. Growth curve of parental DLD1 (pink) and a DLD1 sub-line expressing the human-mouse chimeric B2M (DLD1-Tg(hmcB2M), blue), as measured by cell counting at 1, 2, and 4 days. Error bars represent the standard deviation of three independent replicates. There are no significant differences between these lines at any time-point.

Figure 15:
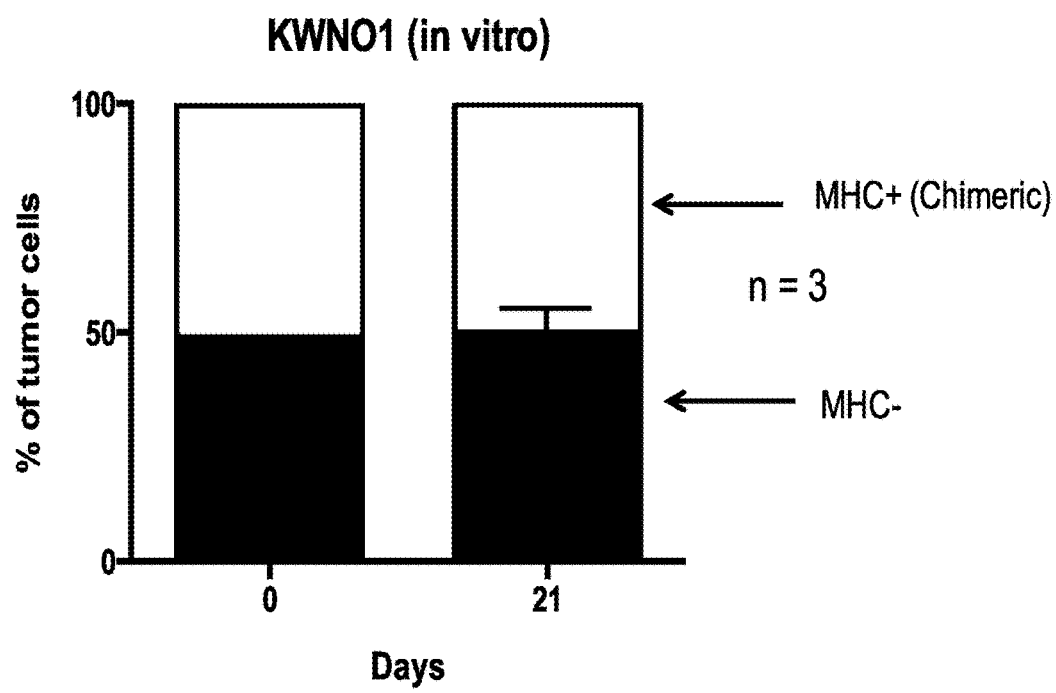

FIG. 15. MHC expression does not influence the in vitro growth kinetics of the KWNO1 cell line in a mixed co-culture. FACS analysis of MHC expression in a 50-50 in vitro co-culture of chimeric MHC+ and MHC− KWNO1 cells, as measured by pan-HLA binding antibody. After 21 days, there was no significant change in the proportion of MHC+ and MHC− cells from day 0. Error bars represent the standard deviation of three independent co-cultures FIG. 16. A Table that provides a statistical comparison between time points and groups.

Figure 17:
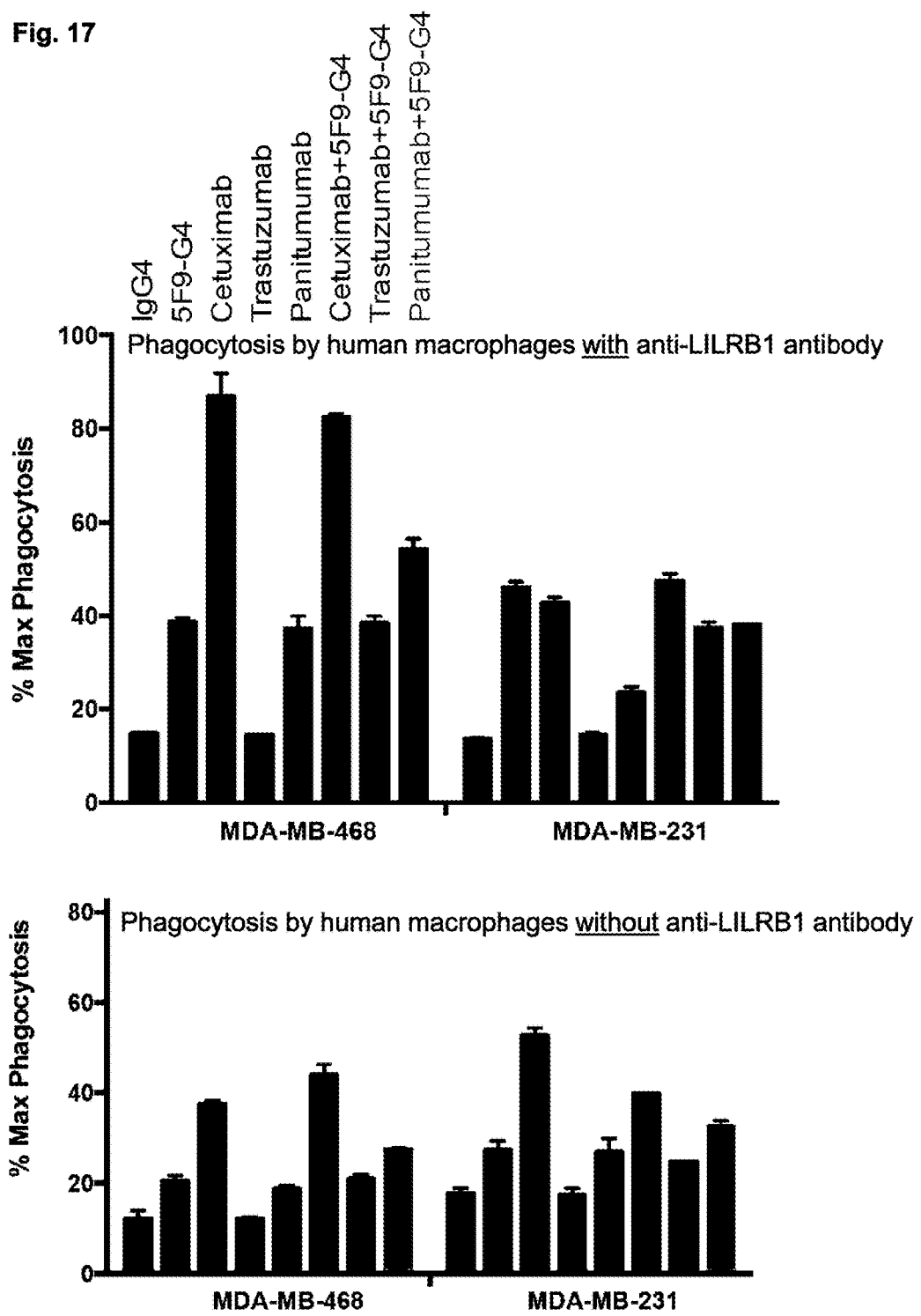

FIG. 17. Results from experiments that measure phagocytosis of two different human breast cancer cell lines (MDA-MB-468 and MDA-MB-231) by human macrophages with and without anti-LILRB1 antibody (and in the presence or absence of other antibodies, e.g., Hu5F9-G4 which is an anti-CD47 antibody). Bars from left to right are: IgG4, Hu5F9-G4, Cetuximab, Trastuzumab, Panitumumab, Cetuximab+Hu5F9-G4, Trastuzumab+Hu5F9-G4, and Panitumumab+Hu5F9-G4.

Figure 18:
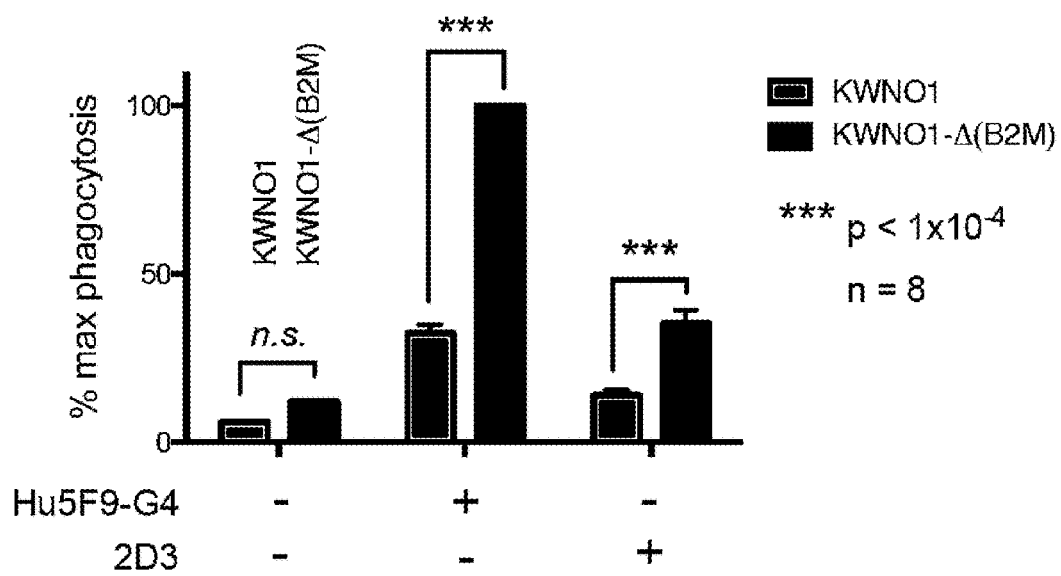

FIG. 18. Data showing that CD47 and MHC class I signaling axes are independent anti-phagocytic signals.

DETAILED DESCRIPTION

Methods and compositions are provided for inducing phagocytosis of a target cell, treating an individual having cancer, treating an individual having an intracellular pathogen infection (e.g., a chronic infection), and/or reducing the number of inflicted cells (e.g., cancer cells, cells infected with an intracellular pathogen, etc.) in an individual. Methods and compositions are also provided for predicting whether an individual is resistant (or susceptible) to treatment with an anti-CD47/SIRPA agent. In some cases, the subject methods and compositions include an anti-MHC Class I/LILRB1 agent. In some cases, the subject methods and compositions include an anti-MHC Class I/LILRB1 agent and an agent that opsonizes a target cell (e.g., co-administration of an anti-MHC Class I/LILRB1 agent and an agent that opsonizes a target cell). In some cases, the subject methods and compositions include an anti-MHC Class I/LILRB1 agent and an anti-CD47/SIRPA agent (e.g., co-administration of an anti-MHC Class I/LILRB1 agent and an anti-CD47/SIRPA agent). Kits are also provided for practicing the methods of the disclosure.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context dearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, aspirate, and the like. A "biological sample" includes a sample comprising target cells and/or normal control cells, or is suspected of comprising such cells. The definition includes biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell (e.g., cancer cell, an infected cell, etc.) from a patient can also include non-inflicted cells.

The term "diagnosis" is used herein to refer to the identification of a molecular or pathological state, disease or condition, such as the identification of a molecular subtype of cancer, the determination that an individual is resistant or susceptible to treatment with an anti-CD47 reagent, and the like.

The term "prognosis" is used herein to refer to the prediction of the likelihood of disease progression (e.g., cancer-attributable death or progression, progression of an infection, etc.), including recurrence, metastatic spread of cancer, and drug resistance (e.g., resistance to treatment with an anti-CD47/SIRPA agent).

The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence. As another example, one may predict the likelihood that an individual is resistant (or susceptible) to treatment with an anti-CD47/SIRPA agent (e.g. determine whether an individual is likely to be resistant to treatment with an anti-CD47/SIRPA agent, or instead is likely to respond to treatment with an anti-CD47/SIRPA agent, i.e., likely to be susceptible to treatment with an anti-CD47/SIRPA agent). As yet another example, one may predict the likelihood that an individual is susceptible to treatment with an anti-CD47/SIRPA agent (e.g. determine whether an individual is likely to be susceptible to treatment with an anti-CD47/SIRPA agent).

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides/epitopes). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Examples of specific binding members include, but are not limited to: agents that specifically bind MHC Class I (e.g., classical MHC Class I), LILRB1, CD47, and/or SIRPA (i.e., anti-MHC Class I/LILRB1 agents, anti-CD47/SIRPA agents), or that otherwise block the interaction between MHC Class I and LILRB1; and/or the interaction between CD47 and SIRPA.

The term "antibody" is used in the broadest sense and specifically covers monoclonal antibodies (including full length monoclonal antibodies), polyclonal antibodies, multispecific antibodies (e.g., bispecific antibodies), and antibody fragments (e.g., Fab fragments) so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Digestion of antibodies (e.g., with enzymes such as papain, Ficin, and the like) produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), where the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "label" when used herein refers to a detectable compound or composition which is conjugated directly or indirectly, e.g., to a subject anti-MHC ClassI/LILRB1 agent and/or anti-CD47/SIRPA agent. The label may itself be detectable by itself (directly detectable label) (e.g., radioisotope labels or fluorescent labels) or, or the label can be indirectly detectable, e.g., in the case of an enzymatic label, the enzyme may catalyze a chemical alteration of a substrate compound or composition and the product of the reaction is detectable.

The terms "phagocytic cells" and "phagocytes" are used interchangeably herein to refer to a cell that is capable of phagocytosis. There are four main categories of phagocytes: macrophages, mononuclear cells (histiocytes and monocytes); polymorphonuclear leukocytes (neutrophils) and dendritic cells.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

Compositions

The present disclosure provides compositions for inducing phagocytosis of a target cell, treating an individual having cancer, treating an individual having an intracellular pathogen infection (e.g., a chronic infection), reducing the number of inflicted cells (e.g., cancer cells, cells infected with an intracellular pathogen, etc.) in an individual, and/or predicting whether an individual is resistant (or susceptible) to treatment with an anti-CD47/SIRPA agent. In some cases, the subject compositions include an anti-MHC Class I/LILRB1 agent. In some cases, the subject compositions include an anti-MHC Class I/LILRB1 agent and an anti-CD47/SIRPA agent.

Anti-MHC Class I/LILRB1 Agent.

A major histocompatibility complex (MHC) Class I complex is made of human leukocyte antigen (HLA) alpha chains and a beta-2-macroglobulin protein (B2M) that assemble to form a complex. HLA alpha chains in humans include the alpha chains HLA-A, HLA-B, HLA-C, HLA-E, HLA-F, HLA-G, HLA-K, and HLA-L. The HLA-A, HLA-B, and HLA-C alpha chains are referred to herein as classical HLA alpha chains. Non-classical MHC Class I HLA alpha chains include HLA-E, HLA-F, HLA-G, HLA-K, and HLA-L. Thus, the term "classical MHC Class I" refers to MHC Class I complexes that include HLA-A, HLA-B, and/or HLA-C (and do not include HLA-E, HLA-F, HLA-G, HLA-K, or HLA-L; and the term "MHC Class I" refers to any MHC Class I complex.

An MHC Class I complex on a first cell (e.g., a cancer cell, an infected cell) can bind to (and activate) LILRB1 on a second cell (e.g., a phagocytic cell, e.g., a macrophage) and thereby inhibit phagocytosis of the first cell by the second cell. "Leukocyte immunoglobulin-like receptor, subfamily B (with TM and ITIM domains), member 1" (LILRB1) is a member of the subfamily B class of leukocyte immunoglobulin-like receptor (LIR) receptors, and contains an ectodomain (having extracellular immunoglobulin domains), a transmembrane domain, and a cytoplasmic domain (having immunoreceptor tyrosine-based inhibitory motifs (ITIMs)). LILRB1 is expressed on immune cells where it binds to MHC class I molecules. When "activated," the receptor transduces a negative signal that inhibits stimulation of an immune response in the cells on which it is expressed.

LILRB1 is also known as ILT2, ILT-2, CD85, CD85J, LIR1, LIR-1, and MIR7. The human LILRB1 protein exists as at least 6 different isoforms (set forth as SEQ ID NOs: 1-6):

LILRB1 (isoform 1)
(SEQ ID NO: 1)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSGPSGGPSSPTTG

PTSTSGPEDQPLTPTGSDPQSGLGRHLGVVIGILVAVILLLLLLLLLF

LILRHRRQGKHWTSTQRKADFQHPAGAVGPEPTDRGLQWRSSPAADAQ

EENLYAAVKHTQPEDGVEMDTRSPHDEDPQAVTYAEVKHSRPRREMAS

PPSPLSGEFLDTKDRQAEEDRQMDTEAAASEAPQDVTYAQLHSLTLRR

EATEPPPSQEGPSPAVPSIYATLAIH

LILRB1 (isoform 2)
(SEQ ID NO: 2)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

-continued
CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSGPSGGPSSPTTG

PTSTSAGPEDQPLTPTGSDPQSGLGRHLGVVIGILVAVILLLLLLLLL

FLILRHRRQGKHWTSTQRKADFQHPAGAVGPEPTDRGLQWRSSPAADA

QEENLYAAVKHTQPEDGVEMDTRQSPHDEDPQAVTYAEVKHSRPRREM

ASPPSPLSGEFLDTKDRQAEEDRQMDTEAAASEAPQDVTYAQLHSLTL

RREATEPPPSQEGPSPAVPSIYATLAIH

LILRB1 (isoform 3)
(SEQ ID NO: 3)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSGPSGGPSSPTTG

PTSTSAGPEDQPLTPTGSDPQSGLGRHLGVVIGILVAVILLLLLLLLL

FLILRHRRQGKHWTSTQRKADFQHPAGAVGPEPTDRGLQWRSSPAADA

QEENLYAAVKHTQPEDGVEMDTRSPHDEDPQAVTYAEVKHSRPRREMA

SPPSPLSGEFLDTKDRQAEEDRQMDTEAAASEAPQDVTYAQLHSLTLR

REATEPPPSQEGPSPAVPSIYATLAIH

LILRB1 (isoform 4)
(SEQ ID NO: 4)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSGPSGGPSSPTTG

PTSTSGPEDQPLTPTGSDPQSGLGVVIGILVAVILLLLLLLLLF

LILRHRRQGKHWTSTQRKADFQHPAGAVGPEPTDRGLQWRSSPAADAQ

EENLYAAVKHTQPEDGVEMDTRQSPHDEDPQAVTYAEVKHSRPRREMA

SPPSPLSGEFLDTKDRQAEEDRQMDTEAAASEAPQDVTYAQLHSLTLR

REATEPPPSQEGPSPAVPSIYATLAIH

LILRB1 (isoform 5)
(SEQ ID NO: 5)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSAGPEDQPLTPTG

SDPQSGLGRHLGVVIGILVAVILLLLLLLLFLILRHRRQGKHWTSTQ

RKADFQHPAGAVGPEPTDRGLQWRSSPAADAQEENLYAAVKHTQPEDG

VEMDTRSPHDEDPQAVTYAEVKHSRPRREMASPPSPLSGEFLDTKDRQ

AEEDRQMDTEAAASEAPQDVTYAQLHSLTLRREATEPPPSQEGPSPAV

PSIYATLAIH

LILRB1 (isoform 6)
(SEQ ID NO: 6)
MTPILTVLICLGLSLGPRTHVQAGHLPKPTLWAEPGSVITQGSPVTLR

CQGGQETQEYRLYREKKTAPWITRIPQELVKKGQFPIPSITWEHTGRY

RCYYGSDTAGRSESSDPLELVVTGAYIKPTLSAQPSPVVNSGGNVTLQ

CDSQVAFDGFILCKEGEDEHPQCLNSQPHARGSSRAIFSVGPVSPSRR

WWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVS

RSYGGQYRCYGAHNLSSEWSAPSDPLDILIAGQFYDRVSLSVQPGPTV

ASGENVTLLCQSQGWMQTFLLTKEGAADDPWRLRSTYQSQKYQAEFPM

GPVTSAHAGTYRCYGSQSSKPYLLTHPSDPLELVVSGPSGGPSSPTTG

PTSTSAGPEDQPLTPTGSDPQSGE

As used herein, the term "anti-MHC Class I/LILRB1 agent" refers to any agent that reduces the binding of MHC Class I (e.g., on a target cell) to LILRB1 (e.g., on a phagocytic cell). In some cases, an anti-MHC Class I/LILRB1 agent binds to (specifically binds) MHC Class I (e.g., classical MHC Class I) (e.g., binds to the fully assembled complex). In some cases, an anti-MHC Class I/LILRB1 agent binds to (specifically binds) one or more components of MHC Class I (e.g., one or more MHC Class I alpha chains, one or more classical MHC Class I alpha chains, and/or B2M), thereby reducing the formation of MHC Class I, which results in reduced binding of MHC Class I to LILRB1. In some cases, an anti-MHC Class I/LILRB1 agent (e.g. an anti-LILRB1 antibody, a soluble MHC class I complex) binds to (specifically binds) LILRB1.

Thus, in some embodiments, a suitable anti-MHC Class I/LILRB1 agent (e.g. an anti-MHC Class I antibody, a LILRB1 peptide, etc.) specifically binds MHC Class I and reduces the binding of MHC Class I to LILRB1. In some embodiments, a suitable anti-MHC Class I/LILRB1 agent (e.g. an anti-MHC Class I antibody, a LILRB1 peptide, etc.) specifically binds classical MHC Class I (MHC Class I complexes that do not include a non-classical HLA alpha chain) and reduces the binding of classical MHC Class I to LILRB1. In some embodiments, a suitable anti-MHC Class I/LILRB1 agent (e.g. an anti-LILRB1 antibody, a soluble MHC class I complex) specifically binds LILRB1.

In some cases, an anti-MHC ClassI/LILRB1 agent (e.g., in any of the methods or compositions of the disclosure) is an antibody (e.g., anti-LLRB1 antibody, anti-MHC Class I antibody) and in some cases it is a humanized antibody (e.g., can be an IgG4 isotype humanized antibody, e.g., an IgG4 isotype antibody having a mutation in the hinge region such as the S241P mutation that reduces heterogeneity sometimes found in chimeric mouse/human IgG4 antibodies)(e.g., see Angal et al., Mol Immunol. 1993 January; 30(1):105-8).

Examples of suitable anti-MHC Class I/LILRB1 agents (MHC Class I binding agents, e.g., classical MHC Class I binding agents, as well as LILRB1 binding agents) include, but are not limited to: (i) anti-MHC Class I antibodies (e.g., antibodies that bind to MHC Class I, antibodies that bind to classical MHC Class I, which include an HLA-A, HLA-B, and/or HLA-C alpha chain); and (ii) LILRB1 peptides, including without limitation soluble LILRB1 polypeptides that bind to MHC Class I, e.g., a polypeptide comprising an extracellular portion (ectodomain) of LILRB1, a high affinity LILRB1 polypeptide, etc.; (iii) anti-LILRB1 antibodies; and (iv) soluble MHC class I complexes that bind to LILRB1. Small molecule compounds that inhibit the binding of MHC Class I (e.g., classical MHC Class I) with LILRB1 are also considered to be anti-MHC Class I/LILRB1 agents.

(i) and (ii) above are examples of MHC Class I binding agents (e.g., classical MHC Class I binding agents); while (iii) and (iv) above are examples of LILRB1 binding agents.

Anti-MHC Class I/LILRB1 agents (e.g., LILRB1 binding agents) do not activate/stimulate LILRB1 (e.g., in the LILRB1-expressing phagocytic cell). In some cases, anti-MHC Class I/LILRB1 agents (e.g., LILRB1 binding agents) do not activate/stimulate LILRB1 to an amount where signaling via LILRB1 is stimulated on phagocytic cells, thereby inhibiting phagocytosis by the phagocytic cells. In other words, in some cases, a suitable anti-MHC Class I/LILRB1 agent that binds LILRB1 can stimulate some level of signaling via LILRB1 on phagocytic cells (i.e., some level of signaling may be tolerated), as long as the level of signaling is not enough to inhibit phagocytosis.

(i) Anti-MHC Class I Antibodies.

In some embodiments, a subject anti-MHC Class I/LILRB1 agent is an antibody (an anti-MHC Class I antibody) that specifically binds MHC class I (e.g., MCH Class I alpha chains HLA-A, HLA-B, and/or HLA-C) and reduces the interaction between MHC Class I on one cell (e.g., an infected cell) and LILRB1 on another cell (e.g., a phagocytic cell). The term "anti-MHC Class I antibody" as used herein encompasses molecules that include the binding region of an anti-MHC Class I antibody, e.g., a molecule that includes the CDRs of an anti-MHC Class I antibody such as a Fab fragment (see definition of the term "antibody" above). Suitable anti-MHC Class I antibodies include fully human, humanized or chimeric versions of such antibodies. For example, humanized antibodies are useful for in vivo applications in humans due to their low antigenicity. Similarly caninized, felinized, etc. antibodies are useful for applications in dogs, cats, and other species respectively. Antibodies of interest include humanized antibodies, or caninized, felinized, equinized, bovinized, porcinized, etc., antibodies, and variants thereof. In some cases, an anti-MHC Class I antibody can be an anti-MHC Class I antibody that does not activate MHC Class I upon binding. Also envisioned are single chain antibodies derived from camelids, single chain antibodies derived from shark, engineered fibronectin domain-containing proteins, knottin peptides, and DARPins; and fluorophore-conjugated versions of each of these reagents.

Examples of monoclonal anti-MHC Class I antibodies can include, but are not limited to clones: W6/32, EP1395Y, OX18, ERMP42, MEM-E/02, 2G5, F21-2, 41.17, OX-27, and 3D12HLA-E. In some embodiments, therefore, the disclosure provides humanized versions of the above described monoclonal antibodies (e.g., those antibodies that recognize human MHC Class I, e.g., human classical MHC Class I). For any of the described anti-MHC Class I antibodies, the antibody can be a humanized antibody, a binding fragment thereof (e.g., a Fab fragment), or any permutation having the antigen binding domain (or, e.g., the CDRs of the antigen binding domain). (See definition of "antibody" above).

In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated herein are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332.

(ii) Soluble LILRB1 Peptide.

A soluble LILRB1 peptide comprises the portion of LILRB1 that is sufficient to bind MHC Class I at a recognizable affinity (e.g., on a target cell such as a cancer cell), which normally lies between the signal sequence and the transmembrane domain, or a fragment thereof that retains the binding activity. A subject soluble LILRB1 peptide does not include the transmembrane domain of LILRB1. A soluble LILRB1 peptide can comprise one or more of the extracellular immunoglobulin domains of LILRB1 (e.g., a soluble LILRB1 peptide can include all or a portion of the soluble portion of the LILRB1 ectodomain). A soluble LILRB1 peptide reduces (e.g., blocks, prevents, etc.) the interaction between LILRB1 and MHC Class I.

Suitable soluble LILRB1 peptides include any peptide comprising variant or naturally existing LILRB1 sequences (e.g., extracellular domain sequences or extracellular domain variants) that can specifically bind LILRB1 and inhibit the interaction between MHC Class I (e.g., classical MHC Class I) and LILRB1 without stimulating enough LILRB1 activity to inhibit phagocytosis. In some embodiments, a subject soluble LILRB1 peptide comprises the extracellular domain of LILRB1, including a signal peptide (e.g., the signal peptide of LILRB1). In some embodiments, the signal peptide amino acid sequence may be substituted with a signal peptide amino acid sequence that is derived from another polypeptide (e.g., for example, an immunoglobulin or CTLA4). For example, unlike full-length LILRB1, which is a cell surface polypeptide that traverses the outer cell membrane, soluble LILRB1 peptides are secreted; accordingly, a soluble LILRB1 peptide may include a heterologous signal peptide that is normally associated with a polypeptide that is secreted from a cell. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). Without wishing to be bound by theory, the signal peptide sequence of LILRB1 is believed to be cleaved from the precursor LILRB1 polypeptide in vivo. In some embodiments, a subject LILRB1 peptide comprises all or a portion of the extracellular domain of LILRB1, but does not include a signal peptide.

Suitable soluble LILRB1 peptides include LILRB1 peptides having extracellular domain mutations (variants) relative to a wild type LILRB1 sequence. In some cases, a subject soluble LILRB1 peptide includes an amino acid sequence having 65% or more (e.g., 70% or more, 75% or more, 80% or more, 85% or more, 90% or more, 95% or more, 97% or more, 98% or more, 99% or more, 99.5% or more, 99.8% or more, or 100%) amino acid sequence identity with the extracellular portion of an amino acid sequence set forth in any of SEQ ID NOs: 1-6, which variants retain the capability to bind to LILRB1 without stimulating LILRB1 signaling enough to inhibit phagocytosis by an LILRB1-expressing phagocytic cell. Assays for measuring whether a given peptide fulfills the above criteria are readily available to one of ordinary skill in the art and any convenient assay can be used. In some embodiments, a subject anti-MHC Class I/LILRB1 agent is a "high affinity LILRB1 peptide", which includes LILRB1-derived polypeptides and analogs thereof. High affinity LILRB1 peptides are variants of an above described LILRB1 peptide that comprise at least one amino acid change relative to the wild-type LILRB1 sequence, where the amino acid change increases the affinity of the LILRB1 peptide for binding to MHC Class I (e.g., classical MHC Class I)(e.g., by decreasing the off-rate by at least 10-fold, at least 20-fold, at least 50-fold, at least 100-fold, at least 500-fold, or more).

In some embodiments, an LILRB1 peptide (e.g., a high affinity LILRB1 peptide) is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region can aid in phagocytosis by providing an "eat me" signal, which enhances the block of the "don't eat me" signal provided by the LILRB1 peptide. In other embodiments, the second polypeptide is any suitable polypeptide that is substantially similar to Fc, e.g., providing increased size, multimerization domains, and/or additional binding or interaction with Ig molecules.

(iii) Anti-LILRB1 Antibodies.

In some embodiments, a subject anti-MHC Class I/LILRB1 agent is an antibody that specifically binds LILRB1 (i.e., an anti-LILRB1 antibody) and reduces the interaction between MHC Class I on one cell (e.g., an infected cell) and LILRB1 on another cell (e.g., a phagocytic cell). Suitable anti-LILRB1 antibodies can bind LILRB1 without activating/stimulating signaling through LILRB1 enough to inhibit phagocytosis. Thus, a suitable anti-LILRB1 antibody specifically binds LILRB1 (without activating/stimulating enough of a signaling response to inhibit phagocytosis) and blocks an interaction between LILRB1 and MHC Class I (e.g., classical MHC Class I). Suitable anti-LILRB1 antibodies include fully human, humanized or chimeric versions of such antibodies. For example, humanized antibodies are useful for in vivo applications in humans due to their low antigenicity. Similarly caninized, felinized, etc. antibodies are useful for applications in dogs, cats, and other species respectively. Antibodies of interest include humanized antibodies, or caninized, felinized, equinized, bovinized, porcinized, etc., antibodies, and variants thereof.

Examples of monoclonal anti-LILRB1 antibodies can include, but are not limited to clones: GHI/75, HP-F1, 3D3-1D12, and VMP55. In some embodiments, therefore, the disclosure provides humanized versions of the above described monoclonal antibodies (e.g., those antibodies that recognize human LILRB1). Also envisioned are single chain antibodies derived from camelids, single chain antibodies derived from shark, engineered fibronectin domain-containing proteins, knottin peptides, and DARPins; and fluorophore-conjugated versions of each of these reagents.

In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated herein are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332.

The inventors have sequenced the GHI/75 antibody and have identified the antigen binding site/domain (the light and heavy chain sequences):

```
Light chain (VJ region) of clone GHI/75
(anti-LILRB1 antibody)(underlined are the CDRs
according to IMGT):
                                    (SEQ ID NO: 7)
DIQMTQSPASQSASLGESVTITCLASQTIGTWLAWYQQKPGKSPQLLIY

AATNLADGVPSRFSGSGSGTKFSFKISSLQAEDFVSYYCQQLYSTPFTF

GSGTKLEIK

CDR-L1:
                                    (SEQ ID NO: 8)
QTIGTW

CDR-L2:
                                    (SEQ ID NO: 9)
AAT

CDR-L3:
                                   (SEQ ID NO: 10)
CQQLYSTPFT
```

-continued

Heavy chain (VDJ region) of clone GHI/75
(anti-LILRB1 antibody)(underlined are the CDRs
according to IMGT):

(SEQ ID NO: 11)
EVILVESGGALVRPGGSLKLSCAASG<u>FTFSSNA</u>MSWVRQTPEKRLEWVA

T<u>ISNGGTFT</u>YYPDSVKGRFTISRDNAKNTLYLQMNSLRSEDTAMYY<u>CAR</u>

<u>HGDGNYGDPL</u>DYWGQGTTLTVSS

CDR-H1:
(SEQ ID NO: 12)
FTFSSNA

CDR-H2:
(SEQ ID NO: 13)
ISNGGTFT

CDR-H3:
(SEQ ID NO: 14)
CARHGDGNYGDPL

For any of the described anti-LILRB1 antibodies, the antibody can be a humanized antibody, a binding fragment thereof (e.g., a Fab fragment), or any permutation having the antigen binding domain (or, e.g., the CDRs of the antigen binding domain). (See definition of "antibody" above).

A subject anti-LILRB1 antibody may include: (i) one or more (e.g., 2 or more, 3 or more, 4 or more, or 5 or more) CDR sequences (e.g., those set forth in SEQ ID NOs: 8-10 and 12-14); (ii) a complete variable region (e.g., those set forth in SEQ ID NOs: 7 and 11); and/or (iii) single-chain variable fragments (e.g., that include any or all of the sequences set forth in SEQ ID NOs: 7-14). As is known in the art, a variable region sequence may be fused to any appropriate constant region sequence.

In some embodiments a subject anti-LILRB1 antibody includes one more CDRs (e.g., 2 or more, 3 or more, 4 or more, 5 or more, or 6 CDRs) that includes an amino acid sequence set forth in SEQ ID NOs: 8-10 and 12-14. A subject anti-LILRB1 antibody can include a CDR sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 8-10 and 12-14.

In some cases, a subject anti-LILRB1 antibody includes one or more CDRs (e.g., 2 or more, 3 or more, 4 or more, 5 or more, or 6) having an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 8-10 and 12-14. In some cases, a subject anti-LILRB1 antibody includes two or more CDRs (e.g., 3 or more, 4 or more, 5 or more, 6, or 6 or more) that have an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 8-10 and 12-14.

In some embodiments, a subject anti-LILRB1 antibody includes an amino acid sequence that is 80% or more (e.g., 85% or more, 90% or more, 92% or more, 95% or more, 97% or more, 98% or more, 99% or more, 99.5% or more, or 100%) identical to a CDR amino acid sequence set forth in any of SEQ ID NOs: 8-10 and 12-14. In some cases, a subject anti-LILRB1 antibody includes a heavy chain having one or more (e.g., two or more, three or more, or 3) of the amino acid sequences set forth in SEQ ID NOs: 12-14. In some cases, a subject anti-LILRB1 antibody includes a heavy chain having all 3 of the amino acid sequences set forth in SEQ ID NOs: 12-14. In some cases, a subject anti-LILRB1 antibody includes a light chain having one or more (e.g., two or more, three or more, or 3) of the amino acid sequences set forth in SEQ ID NOs: 8-10. In some cases, a subject anti-LILRB1 antibody includes a light chain having all 3 of the amino acid sequences set forth in SEQ ID NOs: 8-10.

In some cases, a subject anti-LILRB1 antibody includes a light chain having all 3 of the amino acid sequences set forth in SEQ ID NOs: 8-10, and a heavy chain having all 3 of the amino acid sequences set forth in SEQ ID NOs: 12-14.

In some cases, a subject anti-LILRB1 antibody includes a heavy chain having three CDRs, where CDR-H1 has the amino acid sequence set forth in SEQ ID NO: 12, CDR-H2 has the amino acid sequence set forth in SEQ ID NO: 13, and CDR-H3 has the amino acid sequence set forth in SEQ ID NO: 14. In some cases, a subject anti-LILRB1 antibody includes a light chain having three CDRs, where CDR-L1 has the amino acid sequence set forth in SEQ ID NO: 8, CDR-L2 has the amino acid sequence set forth in SEQ ID NO: 9, and CDR-L3 has the amino acid sequence set forth in SEQ ID NO: 10. In some cases, a subject anti-LILRB1 antibody includes: (i) a heavy chain having three CDRs, where CDR-H1 has the amino acid sequence set forth in SEQ ID NO: 12, CDR-H2 has the amino acid sequence set forth in SEQ ID NO: 13, and CDR-H3 has the amino acid sequence set forth in SEQ ID NO: 14; and (ii) a light chain having three CDRs, where CDR-L1 has the amino acid sequence set forth in SEQ ID NO: 8, CDR-L2 has the amino acid sequence set forth in SEQ ID NO: 9, and CDR-L3 has the amino acid sequence set forth in SEQ ID NO: 10.

In some cases, a subject anti-LILRB1 antibody includes a heavy chain having an amino acid sequence as set forth in SEQ ID NO: 11. In some cases, a subject anti-LILRB1 antibody includes a light chain having amino acid sequence as set forth in SEQ ID NO: 7. In some cases, a subject anti-LILRB1 antibody includes a heavy chain having an amino acid sequence as set forth in SEQ ID NO: 11; and a light chain having an amino acid sequence as set forth in SEQ ID NO: 7.

(iv) Soluble MHC Class I Complex.

In some embodiments, a subject anti-MHC Class I/LILRB1 agent is a soluble MHC Class I complex (or any component thereof) that specifically binds LILRB1 and reduces the interaction between MHC Class I on one cell (e.g., an infected cell) and LILRB1 on another cell (e.g., a phagocytic cell). A suitable soluble MHC Class I complex can bind LILRB1 without activating or stimulating signaling through LILRB1 because activation of LILRB1 would inhibit phagocytosis. A suitable soluble MHC Class I polypeptide specifically binds LILRB1 without activating/stimulating enough of a signaling response to inhibit phagocytosis.

Efficacy of an Anti-MHC Class I/LILRB1 Agent.

The efficacy of a suitable anti-MHC Class I/LILRB1 agent can be assessed by assaying the agent. As a non-limiting example of such an assay, target cells are incubated in the presence or absence of the candidate agent, and phagocytosis of the target cells is measured (e.g., phagocytosis by macrophages). An agent for use in the subject methods (an anti-MHC Class I/LILRB1 agent) will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, at least 200%, or at least 300%) compared to phagocytosis in the absence of the candidate agent. Any convenient phagocytosis assay can be used. As a non-limiting example of a phagocytosis assay, see the Examples below.

In some cases, the assay can be conducted in the presence of a known phagocytosis inducing agent (e.g., an anti-CD47/SIRPA agent). In some cases, in the presence of a known phagocytosis inducing agent (e.g., an anti-CD47/SIRPA agent), an anti-MHC Class I/LILRB1 agent will up-regulate regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, at least 200%, or at least 300%) compared to phagocytosis in the absence of the phagocytosis inducing agent. In some cases, in the presence of a known phagocytosis inducing agent (e.g., an anti-CD47/SIRPA agent), an anti-MHC Class I/LILRB1 agent will up-regulate regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, at least 200%, or at least 300%) compared to phagocytosis in the absence of the candidate agent.

Similarly, an in vitro assay that measures tyrosine phosphorylation of LILRB1 can be used (e.g., as an alternative or in addition to a phagocytosis assay). In some cases, a suitable candidate agent will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent. In some cases, in the presence of a known phagocytosis inducing agent (e.g., an anti-CD47/SIRPA agent), a suitable candidate anti-MHC Class I/LILRB1 agent will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation in the absence of the phagocytosis inducing agent. In some cases, in the presence of a known phagocytosis inducing agent (e.g., an anti-CD47/SIRPA agent), a suitable candidate anti-MHC Class I/LILRB1 agent will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation in the absence of the candidate agent.

Anti-CD47/SIRPA Agent.

As used herein, the term "anti-CD47/SIRPA agent" refers to any agent that reduces the binding of CD47, e.g., on a target cell, to SIRPA (also known as SIRPα), e.g., on a phagocytic cell. Non-limiting examples of suitable anti-CD47/SIRPA agents include SIRPA reagents, including without limitation high affinity SIRPA polypeptides; anti-SIRPA antibodies; soluble CD47 polypeptides; and anti-CD47 antibodies or antibody fragments. In some embodiments, a suitable anti-CD47/SIRPA agent (e.g. an anti-CD47 antibody, a SIRPA reagent, etc.) specifically binds CD47 to reduce the binding of CD47 to SIRPA. In some embodiments, a suitable anti-CD47/SIRPA agent (e.g., an anti-SIRPA antibody, a soluble CD47 polypeptide, etc.) specifically binds SIRPA to reduce the binding of CD47 to SIRPA. A suitable anti-CD47/SIRPA agent that binds SIRPA does not activate SIRPA (e.g., in the SIRPA-expressing phagocytic cell). The efficacy of a suitable anti-CD47/SIRPA agent can be assessed by assaying the agent (further described below). As a non-limiting example of such an assay, target cells are incubated in the presence or absence of the candidate agent, and phagocytosis of the target cells is measured (e.g., phagocytosis by macrophages). An agent for use in the subject methods (an anti-CD47/SIRPA agent) will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, at least 200%, or at least 300%) compared to phagocytosis in the absence of the candidate agent. Any convenient phagocytosis assay can be used. As a non-limiting example of a phagocytosis assay, see the Examples below. Similarly, an in vitro assay that measures tyrosine phosphorylation of SIRPA can be used (e.g., as an alternative or in addition to a phagocytosis assay). A suitable candidate agent will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47/SIRPA agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47/SIRPA agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., Virology. 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47/SIRPA agent (e.g., anti-CD47 antibody, a SIRPA reagent, a SIRPA antibody, a soluble CD47 polypeptide, etc.) can reduce the binding of a CD47 analog (i.e., a CD47 mimic) to SIRPA. In some cases, a suitable anti-CD47/SIRPA agent (e.g., a SIRPA reagent, an anti-CD47 antibody, etc.) can bind a CD47 analog (i.e., a CD47 mimic) to reduce the binding of the CD47 analog to SIRPA. In some cases, a suitable anti-CD47/SIRPA agent (e.g., an anti-SIRPA antibody, a soluble CD47 polypeptide, etc.) can bind to SIRPA. A suitable anti-CD47/SIRPA agent that binds SIRPA does not activate SIRPA (e.g., in the SIRPA-expressing phagocytic cell). An anti-CD47/SIRPA agent can be used in any of the methods provided herein when the pathogen is a pathogen that provides a CD47 analog. In other words the term "CD47," as used herein, encompasses CD47 as well as CD47 analogs (i.e., CD47 mimics).

SIRPA Reagent.

A SIRPA reagent comprises the portion of SIRPA that is sufficient to bind CD47 at a recognizable affinity, which normally lies between the signal sequence and the transmembrane domain, or a fragment thereof that retains the binding activity. A suitable SIRPA reagent reduces (e.g., blocks, prevents, etc.) the interaction between the native proteins SIRPA and CD47. The SIRPA reagent will usually comprise at least the d1 domain of SIRPA. In some embodiments, a SIRPA reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPA reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47/SIRPA agent is a "high affinity SIRPA reagent", which includes SIRPA-derived polypeptides and analogs thereof. High affinity SIRPA reagents are described in international application PCT/US13/21937, which is hereby specifically incorporated by reference. High affinity SIRPA reagents are variants of the native SIRPA protein. In some embodiments, a high affinity SIRPA reagent is soluble, where the polypeptide lacks the SIRPA transmembrane domain and comprises at least one amino acid change relative to the wild-type SIRPA sequence, and wherein the amino acid change increases the affinity of the SIRPA polypeptide binding to CD47, for example by decreasing the off-rate by at least 10-fold, at least 20-fold, at least 50-fold, at least 100-fold, at least 500-fold, or more.

A high affinity SIRPA reagent comprises the portion of SIRPA that is sufficient to bind CD47 at a recognizable affinity, e.g., high affinity, which normally lies between the signal sequence and the transmembrane domain, or a fragment thereof that retains the binding activity. The high affinity SIRPA reagent will usually comprise at least the d1 domain of SIRPA with modified amino acid residues to increase affinity. In some embodiments, a SIRPA variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPA reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPA reagents comprise a d1 domain of human SIRPA, with at least one amino acid change relative to the wild-type sequence within the d1 domain. Such a high affinity SIRPA reagent optionally comprises additional amino acid sequences, for example antibody Fc sequences; portions of the wild-type human SIRPA protein other than the d1 domain, including without limitation residues 150 to 374 of the native protein or fragments thereof, usually fragments contiguous with the d1 domain; and the like. High affinity SIRPA reagents may be monomeric or multimeric, i.e. dimer, trimer, tetramer, etc. An example of a high-affinity SIRPA reagent is known as CV1 (an engineered protein monomer).

Anti-CD47 Antibodies.

In some embodiments, a subject anti-CD47/SIRPA agent is an antibody that specifically binds CD47 (i.e., an anti-CD47 antibody) and reduces the interaction between CD47 on one cell (e.g., an infected cell) and SIRPA on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPA Antibodies.

In some embodiments, a subject anti-CD47/SIRPA agent is an antibody that specifically binds SIRPA (i.e., an anti-SIRPA antibody) and reduces the interaction between CD47 on one cell (e.g., an infected cell) and SIRPA on another cell (e.g., a phagocytic cell). Suitable anti-SIRPA antibodies can bind SIRPA without activating or stimulating signaling through SIRPA because activation of SIRPA would inhibit phagocytosis. Instead, suitable anti-SIRPA antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPA antibody specifically binds SIRPA (without activating/stimulating enough of a signaling response to inhibit phagocytosis) and blocks an interaction between SIRPA and CD47. Suitable anti-SIRPA antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 Polypeptides.

In some embodiments, a subject anti-CD47/SIRPA agent is a soluble CD47 polypeptide that specifically binds SIRPA and reduces the interaction between CD47 on one cell (e.g., an infected cell) and SIRPA on another cell (e.g., a phagocytic cell). A suitable soluble CD47 polypeptide can bind SIRPA without activating or stimulating signaling through SIRPA because activation of SIRPA would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPA without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPA are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPA and inhibit the interaction between CD47 and SIRPA without stimulating enough SIRPA activity to inhibit phagocytosis.

In certain embodiments, soluble CD47 polypeptide comprises the extracellular domain of CD47, including the signal peptide. Soluble CD47 polypeptides also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPA without stimulating SIRPA signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPA without stimulating SIRPA signaling. The CD47 extracellular domain variant may have an amino acid sequence that is at least 65%-75%, 75%-80%, 80-85%, 85%-90%, or 95%-99% identical (which includes any percent identity between any one of the described ranges) to the extracellular domain of wild type CD47.

The above described agents can be prepared in a variety of ways. For example, an anti-MHC Class I/LILRB1 agent and/or anti-CD47/SIRPA agent can be prepared (together or separately): as a dosage unit, with a pharmaceutically acceptable excipient, with pharmaceutically acceptable salts and esters, etc. Compositions can be provided as pharmaceutical compositions.

Pharmaceutical Compositions.

Suitable anti-MHC Class I/LILRB1 agents and/or anti-CD47/SIRPA agents can be provided in pharmaceutical compositions suitable for therapeutic use, e.g. for human treatment. In some embodiments, pharmaceutical compositions of the present invention include one or more therapeutic entities of the present disclosure (e.g., an anti-MHC ClassI/LILRB1 agent and/or an anti-CD47/SIRPA agent) and include a pharmaceutically acceptable carrier, a pharmaceutically acceptable salt, a pharmaceutically acceptable excipient, and/or esters or solvates thereof. In some embodiments, the use of an anti-MHC Class I/LILRB1 agent and/or anti-CD47/SIRPA agent includes use in combination with another therapeutic agent (e.g., another anti-infection agent or another anti-cancer agent). Therapeutic formulations comprising an anti-MHC Class I/LILRB1 agent and/or an anti-CD47/SIRPA agent can be prepared by mixing the agent(s) having the desired degree of purity with a physiologically acceptable carrier, a pharmaceutically acceptable salt, an excipient, and/or a stabilizer (Remington's Pharmaceutical Sciences 16th edition, Osol, A. Ed. (1980)) (e.g., in the form of lyophilized formulations or aqueous solutions). A composition having an anti-MHC Class I/LILRB1 agent and/or an anti-CD47/SIRPA agent can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

Methods

Methods are provided for inducing phagocytosis of a target cell, treating an individual having cancer, treating an individual having an intracellular pathogen infection (e.g., a chronic infection), reducing the number of inflicted cells (e.g., cancer cells, cells infected with an intracellular pathogen, etc.) in an individual, and/or predicting whether an individual is resistant (or susceptible) to treatment with an anti-CD47/SIRPA agent. In some cases, the subject methods include the use of an anti-MHC Class I/LILRB1 agent and an agent that opsonizes a target cell (e.g., co-administration of an anti-MHC Class I/LILRB1 agent and an agent that opsonizes a target cell). In some cases, the subject methods include the use of an anti-MHC Class I/LILRB1 agent and an anti-CD47/SIRPA agent (e.g., co-administration of an anti-MHC Class I/LILRB1 agent and an anti-CD47/SIRPA agent). In some cases, the subject methods include the use of an anti-MHC Class I/LILRB1 agent, an anti-CD47/SIRPA agent, and an agent that opsonizes a target cell (e.g., co-administration of an anti-MHC Class I/LILRB1 agent, an anti-CD47/SIRPA agent, and an agent that opsonizes a target cell). In some cases an anti-CD47/SIRPA agent is an agent that opsonizes a target cell (e.g., when the anti-CD47/SIRPA agent is an anti-CD47 antibody having an Fc region).

The compositions described above can find use in the methods described herein.

In some cases, a subject method is a method of inducing phagocytosis of a target cell. The term "target cell" as used herein refers to a cell (e.g., inflicted cells such as cancer cells, infected cells, etc.) that is targeted for phagocytosis by a phagocytic cell. In some cases, a target cell is resistant to treatment with an anti-CD47/SIRPA agent. For example, some inflicted cells (e.g., cancer cells) do not express MHC Class I and such cells are susceptible to an anti-CD47/SIRPA agent. When a target cell that is susceptible to an anti-CD47/SIRPA agent is contacted with a phagocytic cell in the presence of an anti-CD47/SIRPA agent, the target cell can be engulfed (e.g., phagocytosed) by the phagocytic cell.

However, some inflicted cells (e.g., cancer cells) do express MHC Class I and such cells can be resistant to an anti-CD47/SIRPA agent. When a target cell that is resistant to an anti-CD47/SIRPA agent is contacted with a phagocytic cell (e.g., a macrophage) in the presence of an anti-CD47/SIRPA agent, the target cell is less likely to be engulfed (e.g., phagocytosed) by the phagocytic cell (see the working examples below). In some embodiments, a target cell (e.g., a target cell that is resistant to an anti-CD47/SIRPA agent) is contacted with a phagocytic cell (e.g., a macrophage) in the presence of an anti-MHC Class I/LILRB1 agent and an anti-CD47/SIRPA agent. When a target cell that is resistant to an anti-CD47/SIRPA agent (e.g., the resistant target cell expresses MHC Class I) is contacted with a phagocytic cell (e.g., a macrophage) in the presence of an anti-MHC Class I/LILRB1 agent and an anti-CD47/SIRPA agent, the phagocytic cell can engulf (e.g., phagocytose) the target cell. Contacting a target cell with a phagocytic cell (e.g., a macrophage) in the presence of an anti-MHC Class I/LILRB1 agent and an anti-CD47/SIRPA agent encompasses scenarios where the target cell is contacted with the anti-MHC Class I/LILRB1 agent and the anti-CD47/SIRPA agent at the same time (i.e, both agents are present at the same time), and scenarios where the target cell is contacted with one of the agents prior to the other agent (in either order)(e.g., one of the agents is present first, and the other agent is later added, either in the presence or absence of the first agent).

Contacting a target cell with a phagocytic cell (e.g., a macrophage) in the present of an anti-MHC Class I/LILRB1 agent and an anti-CD47/SIRPA agent can occur in vitro or in vivo. For example, in some cases, a target cell (e.g., a cancer cell from an individual, a cancer cell of an immortalized cell line, an infected cell from an individual, an infected cell of a cell line, and the like) is cultured in vitro with a phagocytic cell, an anti-MHC Class I/LILRB1 agent, and an anti-CD47/SIRPA agent.

In some cases, after the phagocytic cell engulfs the target cell, the phagocytic cell is introduced into an individual (e.g., the individual from whom the target cell was taken). In some cases, the phagocytic cell is a cell from an individual (e.g., the same individual from whom the target cell was taken) and the phagocytic cell is re-introduce into the individual after the phagocytic cell engulfs the target cell. When the target cell and/or the phagocytic cell is from an individual that is being treated, the method can be referred to as an ex vivo method. In some cases, a method of inducing phagocytosis of a target cell, where the method includes contacting the target cell with a phagocytic cell (e.g., a macrophage) in the presence of an anti-MHC Class I/LILRB1 agent and an anti-CD47/SIRPA agent, can occur in vivo. In such cases, the anti-MHC Class I/LILRB1 agent and the anti-CD47/SIRPA agent can be administered to an individual (e.g., an individual having cancer, a chronic infection, etc.) and the contact of the target cell with the phagocytic cell will happen in vivo, without further input from the one performing the method. As such, in some cases, a method of inducing phagocytosis of a target cell can encompass a method that includes administering to an individual an anti-MHC Class I/LILRB1 agent and an anti-CD47/SIRPA agent.

A target cell may be a cell that is "inflicted", where the term "inflicted" is used herein to refer to a subject with symptoms, an illness, or a disease that can be treated with an anti-MHC Class I/LILRB1 agent and an anti-CD47/SIRPA agent. An "inflicted" subject can have cancer, can harbor an infection (e.g., a chronic infection), and other hyper-proliferative conditions, for example sclerosis, fibrosis, and the like. "Inflicted cells" may be those cells that cause the symptoms, illness, or disease. As non-limiting examples, the inflicted cells of an inflicted patient can be cancer cells, infected cells, and the like. One indication that an illness or disease can be treated with an anti-CD47/SIRPA agent is that the involved cells (i.e., the inflicted cells, e.g., the cancerous cells, the infected cells, etc.) express an increased level of CD47 compared to normal cells of the same cell type. One indication that an illness or disease can be treated with an anti-MHC Class I/LILRB1 agent is that the involved cells (i.e., the inflicted cells, e.g., the cancerous cells, the infected cells, etc.) express MHC Class I (e.g., classical MHC Class I). In some cases, an indication that an illness or disease can be treated with an anti-MHC Class I/LILRB1 agent and an anti-CD47/SIRPA agent is that the involved cells (i.e., the inflicted cells, e.g., the cancerous cells, the infected cells, etc.) express an increased level of CD47 compared to normal cells of the same cell type, and express MHC Class I (e.g., classical MHC Class I).

In some cases, a subject method is a method of treating an individual having cancer and/or having an intracellular pathogen infection (e.g., a chronic infection). An effective treatment will reduce the number of inflicted cells (e.g., cancer cells, cells infected with an intracellular pathogen, etc.) in an individual (e.g., via increasing phagocytosis of the target cells). As such, in some cases, a subject method is a method of reducing the number of inflicted cells (e.g., cancer cells, cells infected with an intracellular pathogen, etc.) in an individual.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, those with an immune disorder, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

Examples of symptoms, illnesses, and/or diseases that can be treated with an anti-MHC Class I/LILRB1 agent (e.g. in combination with an anti-CD47/SIRPA agent) include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection from an intracellular pathogen (e.g., chronic infection); and immunological diseases or disorders (e.g., an inflammatory disease)(e.g., multiple sclerosis, arthritis, and the like)(e.g., for immunosuppressive therapy).

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer is a suitable cancer to be treated by the subject methods and compositions.

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratoma is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) (e.g., one that induces increased CD47 expression in at least one cell of the infected organism). For example, infectious agents include, but are not limited to bacteria, viruses, protozoans, and fungi. Intracellular pathogens are also of interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehdichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

Infectious diseases that can be treated using a subject anti-MHC Class I/LILRB1 agent and/or anti-CD47/SIRPA agent include but are not limited to: HIV, Influenza, Herpes, *Giardia, Malaria, Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, *mycobacteria, staphylococci, streptococci, pneumonococci, meningococci* and *conococci, klebsiella, proteus, serratia, pseudomonas, E. coli, legionella*, diphtheria, *salmonella, bacilli*, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptospondium* sp., *Pneumocystis carinii, Plasmodium vivax, Babesia microti, Trypanosoma brucei, Trypanosoma cruzi, Leishmania donovani, Toxoplasma gondi*, and/or *Nippostrongylus brasiliensis*.

In some embodiments the infliction is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

An infection treated with the methods of the invention generally involves a pathogen with at least a portion of its life-cycle within a host cell, i.e. an intracellular phase. The methods of the invention provide for a more effective removal of infected cells by the phagocytic cells of the host organism, relative to phagocytosis in the absence of treatment, and thus are directed to the intracellular phase of the pathogen life cycle.

The terms "co-administration", "co-administer", and "in combination with" include the administration of two or more therapeutic agents (e.g., an anti-MHC Class I/LILRB1 agent and an anti-CD47/SIRPA agent) either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject an anti-MHC Class I/LILRB1 agent and/or an anti-CD47/SIRPA agent (e.g., formulated as a pharmaceutical composition) is co-administered with a cancer therapeutic drug, therapeutic drug to treat an infection, or tumor-directed antibody. Such administration may involve concurrent (i.e. at the same time), prior, or subsequent administration of the drug/antibody with respect to the administration of an agent or agents of the disclosure. A person of ordinary skill in the art would have no difficulty determining the appropriate timing, sequence and dosages of administration for particular drugs and compositions of the present disclosure.

In some embodiments, treatment is accomplished by administering a combination (co-administration) of a subject anti-MHC Class I/LILRB1 agent (e.g., with or without an anti-CD47/SIRPA agent) with another agent (e.g., an immune stimulant, an agent to treat chronic infection, a cytotoxic agent, an anti-cancer agent, etc.). One example class of cytotoxic agents that can be used are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

An anti-MHC ClassI/LILRB1 agent and/or an anti-CD47/SIRPA agent need not be, but is optionally formulated with one or more agents that potentiate activity, or that otherwise increase the therapeutic effect. These are generally used in the same dosages and with administration routes as used herein or from 1 to 99% of the heretofore employed dosages. In some embodiments, treatment is accomplished by administering a combination (co-administration) of a subject anti-MHC Class I/LILRB1 agent and an agent that opsonizes a target cell. In some embodiments, treatment is accomplished by administering a combination (co-administration) of a subject anti-MHC Class I/LILRB1 agent, an agent that opsonizes a target cell, and an anti-CD47/SIRPA agent. In some embodiments, treatment is accomplished by administering a combination (co-administration) of a subject anti-MHC Class I/LILRB1 agent and an anti-CD47/SIRPA agent. Thus, also envisioned herein are compositions (and methods that use the compositions) that include: (a) an anti-MHC ClassI/LILRB1 agent; and (b) at least one of: (i) an agent that opsonizes the target cell, and (ii) an anti-CD47/SIRPA agent. In some cases, that agent that opsonizes the target cell is Rituximab. In some cases, that agent that opsonizes the target cell is Cetuximab.

An "agent that opsonizes a target cell" (an "opsonizing agent") is any agent that can bind to a target cell (e.g., a cancer cell, a cell harboring an intracellular pathogen, etc.) and opsonize the target cell. For example, any antibody that can bind to a target cell (as defined herein), where the antibody has an FC region, is considered to be an agent that opsonizes a target cell. In some cases, the agent that opsonizes a target cell is an antibody, other than an anti-CD47 antibody, that binds to a target cell (e.g., an anti-tumor antibody, an anti-cancer antibody, an anti-infection antibody, and the like).

For example antibodies selective for tumor cell markers, radiation, surgery, and/or hormone deprivation, see Kwon et al., Proc. Natl. Acad. Sci U.S.A., 96: 15074-9, 1999. Angiogenesis inhibitors can also be combined with the methods of the invention. A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Monoclonal antibodies useful in the methods of the invention that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. This antigen is seen on 25% to 35% of breast cancers. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

A subject anti-MHC Class I/LILRB1 agent can be combined (with or without an anti-CD47/SIRPA agent) any of the above mentioned antibodies (agents that opsonize a target cell). Thus, in some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with one or more cell-specific antibodies selective for tumor cell markers. in some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and one or more cell-specific antibodies selective for tumor cell markers.

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with one or more of: cetuximab (binds EGFR), panitumumab (binds EGFR), rituximab (binds CD20), trastuzumab (binds HER2), pertuzumab (binds HER2), alemtuzumab (binds CD52), brentuximab (binds CD30), tositumomab, ibritumomab, gemtuzumab, ibritumomab, and edrecolomab (binds 17-1A).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and one or more of: cetuximab (binds EGFR), panitumumab (binds EGFR), rituximab (binds CD20), trastuzumab (binds HER2), pertuzumab (binds HER2), alemtuzumab (binds CD52), brentuximab (binds CD30), tositumomab, ibritumomab, gemtuzumab, ibritumomab, and edrecolomab (binds 17-1A).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with one or more agents that specifically bind one or more of: CD19, CD20, CD22, CD24, CD25, CD30, CD33, CD38, CD44, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and one or more agents that specifically bind one or more of: CD19, CD20, CD22, CD24, CD25, CD30, CD33, CD38, CD44, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with any convenient immunomodulatory agent (e.g., an anti-CTLA4 antibody, an anti-PD-1 antibody, an anti-PD-L1 antibody, a CD40 agonist, a 4-1BB modulator (e.g., a 41BB-agonist), and the like).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and any convenient immunomodulatory agent (e.g., an anti-CTLA4 antibody, an anti-PD-1 antibody, an anti-PD-L1 antibody, a CD40 agonist, a 4-1BB modulator (e.g., a 41BB-agonist), and the like).

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an inhibitor of BTLA and/or CD160.

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and an inhibitor of BTLA and/or CD160.

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an inhibitor of TIM3 and/or CEACAM1.

In some cases, a subject anti-MHC Class I/LILRB1 agent, e.g., an agent that specifically binds classical MHC Class I (e.g., an anti-MHC Class I antibody, a LILRB1 peptide) and/or an agent that specifically binds LILRB1 (e.g. an anti-LILRB1 antibody, a soluble MHC class I complex), is used in a combination therapy (is co-administered) with an anti-CD47/SIRPA agent and an inhibitor of TIM3 and/or CEACAM1.

Treatment may also be combined with other active agents, such as antibiotics, cytokines, anti-viral agents, etc. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefacior, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of an anti-MHC Class I/LILRB1 agent and/or an anti-CD47/SIRPA agent is an amount that is sufficient to palliate, ameliorate, stabilize, reverse, prevent, slow or delay the progression of the disease state (e.g., cancer or chronic infection) by increasing phagocytosis of a target cell (e.g., a target cell). Thus, a therapeutically effective dose of an anti-MHC Class I/LILRB1 agent and/or an anti-CD47/SIRPA agent reduces the binding of (i) MHC on an target cell, to LILRB1 on a phagocytic cell; and/or (ii) CD47 on an target cell, to SIRPA on a phagocytic cell; at an effective dose for increasing the phagocytosis of the target cell.

In some embodiments, a therapeutically effective dose leads to sustained serum levels of an anti-MHC Class I/LILRB1 agent and/or an anti-CD47/SIRPA agent (e.g., an anti-MHC anti-body and/or an anti-CD47 antibody) of 40 µg/ml or more (e.g, 50 ug/ml or more, 60 ug/ml or more, 75 ug/ml or more, 100 ug/ml or more, 125 ug/ml or more, or 150 ug/ml or more) for each agent. In some embodiments, a therapeutically effective dose leads to sustained serum levels of an anti-MHC Class I/LILRB1 agent and/or an anti-CD47/SIRPA agent (e.g., an anti-MHC anti-body and/or an anti-CD47 antibody) that range from 40 µg/ml to 300 ug/ml (e.g, from 40 ug/ml to 250 ug/ml, from 40 ug/ml to 200 ug/ml, from 40 ug/ml to 150 ug/ml, from 40 ug/ml to 100 ug/ml, from 50 ug/ml to 300 ug/ml, from 50 ug/ml to 250 ug/ml, from 50 ug/ml to 200 ug/ml, from 50 ug/ml to 150 ug/ml, from 75 ug/ml to 300 ug/ml, from 75 ug/ml to 250 ug/ml, from 75 ug/ml to 200 ug/ml, from 75 ug/ml to 150 ug/ml, from 100 ug/ml to 300 ug/ml, from 100 ug/ml to 250 ug/ml, or from 100 ug/ml to 200 ug/ml) for each agent. In some embodiments, a therapeutically effective dose for treating solid tumors leads to sustained serum levels of an anti-MHC Class I/LILRB1 agent and/or an anti-CD47/SIRPA agent (e.g., an anti-MHC anti-body and/or an anti-CD47 antibody) of 100 µg/ml or more (e.g., sustained serum levels that range from 100 ug/ml to 200 ug/ml) for each agent. In some embodiments, a therapeutically effective dose for treating non-solid tumors (e.g., acute myeloid leukemia (AML)) leads to sustained serum levels of an anti-MHC Class I/LILRB1 agent and/or an anti-CD47/SIRPA agent (e.g., an anti-MHC anti-body and/or an anti-CD47 antibody) of 50 µg/ml or more (e.g., sustained serum levels of 75 µg/ml or more; or sustained serum levels that range from 50 ug/ml to 150 ug/ml) for each agent.

Accordingly, a single therapeutically effective dose or a series of therapeutically effective doses would be able to achieve and maintain a serum level of an anti-MHC Class I/LILRB1 agent and/or an anti-CD47/SIRPA agent. A therapeutically effective dose of an anti-MHC Class I/LILRB1 agent and/or an anti-CD47/SIRPA agent can depend on the specific agent used, but is usually 8 mg/kg body weight or more (e.g., 8 mg/kg or more, 10 mg/kg or more, 15 mg/kg or more, 20 mg/kg or more, 25 mg/kg or more, 30 mg/kg or more, 35 mg/kg or more, or 40 mg/kg or more) for each agent, or from 10 mg/kg to 40 mg/kg (e.g., from 10 mg/kg to 35 mg/kg, or from 10 mg/kg to 30 mg/kg) for each agent. The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art. For all therapeutically effective doses listed above, when both an anti-MHC Class I/LILRB1 agent and an anti-CD47/SIRPA agent are used, the dose for each agent can be independent from the other agent. As an illustrative example (to illustrate the independence of the doses), a therapeutic dose of the anti-MHC Class I/LILRB1 agent may be from 75 ug/ml to 250 ug/ml while a therapeutic dose of the anti-CD47/SIRPA agent may be from 40 ug/ml to 100 ug/ml.

Dosage and frequency may vary depending on the half-life of the anti-MHC Class I/LILRB1 agent and/or anti-CD47/SIRPA agent in the patient. It will be understood by one of skill in the art that such guidelines will be adjusted for the molecular weight of the active agent, e.g. in the use of antibody fragments, in the use of antibody conjugates, in the use of anti-MHC Class I/LILRB1 agents, in the use of anti-CD47/SIRPA agents, etc. The dosage may also be varied for localized administration, e.g. intranasal, inhalation, etc., or for systemic administration, e.g. i.m., i.p., i.v., and the like.

A sub-therapeutic dose is a dose (i.e., an amount) that is not sufficient to effect the desired clinical results when used in a particular context. For example, a sub-therapeutic dose of an anti-CD47/SIRPA agent is an amount that is not sufficient to palliate, ameliorate, stabilize, reverse, prevent, slow or delay the progression of the disease state (e.g., cancer, infection, inflammation, etc.). However, in some cases, when a sub-therapeutic dose of an anti-CD47/SIRPA agent is used in combination with (co-administered with) a subject anti-MHC Class I/LILRB1 agent, the dose can become a therapeutic dose. In other words, in some cases, a given dose of an anti-CD47/SIRPA agent can be sub-therapeutic when used in the absence of a subject anti-MHC Class I/LILRB1 agent, but therapeutic when used in the presence of an anti-MHC Class I/LILRB1 agent. Thus, in some cases, an anti-CD47/SIRPA agent can be co-administration with an anti-MHC Class I/LILRB1 agent, where the dose of the anti-CD47/SIRPA agent would otherwise be sub-therapeutic (e.g., the dose of the anti-CD47/SIRPA agent would be sub-therapeutic when used in the absence of an anti-MHC Class I/LILRB1 agent. In some cases, it is desirable to use a sub-therapeutic dose of an anti-CD47/SIRPA agent in combination with a subject anti-MHC Class I/LILRB1 agent. In some cases, a sub-therapeutic dose of an anti-CD47/SIRPA agent (sub-therapeutic when used in the absence of an anti-MHC Class I/LILRB1 agent) is a therapeutic dose when the agent is used in combination (co-administered) with an anti-MHC Class I/LILRB1 agent.

While the use of a sub-therapeutic dose of an anti-CD47/SIRPA agent in combination with an anti-MHC ClassI/LILRB1 agent achieves a desired outcome (e.g., the combination is therapeutic), the dose is not considered to be a "therapeutic dose" because the sub-therapeutic dose does not effectively increase phagocytosis of a target cell and is not sufficient to palliate, ameliorate, stabilize, reverse, prevent, slow or delay the progression of the disease state, unless used in combination with an anti-MHC ClassI/LILRB1 agent. A sub-therapeutic dose of an anti-CD47/SIRPA agent can depend on the specific agent used, but in some cases is less than 10 mg/kg.

In some cases, a sub-therapeutic dose of an anti-CD47/SIRPA agent is desirable because some anti-CD47/SIRPA agents, when used at a high enough dose, can cause a reduction of red blood cells in an individual being treated. Thus, in some cases, co-administration with an anti-MHC ClassI/LILRB1 agent allows for the anti-CD47/SIRPA agent to be used at a dose that reduces the potential loss of red blood cells, but that would otherwise be considered a sub-therapeutic dose. As such, a co-administration may be able to circumvent the reduction of blood cells.

An anti-MHC ClassI/LILRB1 agent and/or an anti-CD47/SIRPA agent can be administered by any suitable means, including topical, oral, parenteral, intrapulmonary, and intranasal. Parenteral infusions include intramuscular, intravenous (bolus or slow drip), intraarterial, intraperitoneal, intrathecal or subcutaneous administration. An anti-MHC ClassI/LILRB1 agent and/or an anti-CD47/SIRPA agent can be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the disclosure, by such means as depot injections or erodible implants. Localized delivery is particularly contemplated, by such means as delivery via a catheter to one or more arteries, such as the renal artery or a vessel supplying a localized tumor.

As noted above, an anti-MHC ClassI/LILRB1 agent and/or an anti-CD47/SIRPA agent can be formulated with an a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

An anti-MHC ClassI/LILRB1 agent and/or an anti-CD47/SIRPA agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-MHC ClassI/LILRB1 agent and/or an anti-CD47/SIRPA agent by non-covalent associations, such as non-covalent bonding or by encapsulation. The nature of the carrier can be either soluble or insoluble for purposes of the invention. Those skilled in the art will know of other suitable carriers for binding anti-MHC Class I/LILRB1 agents and/or anti-CD47/SIRPA agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-MHC ClassI/LILRB1 agent and/or an anti-CD47/SIRPA agent through an acceptable chemical linker or chelation carrier. Positron emitting moieties for use in the present invention include $^{18}F$, which can be easily conjugated by a fluorination reaction with the anti-MHC ClassI/LILRB1 agent and/or an anti-CD47/SIRPA agent.

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-MHC Class I/LILRB1 agents and/or anti-CD47/SIRPA agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

In some cases, a method of inducing phagocytosis of a target cell, treating an individual having cancer, treating an individual having an intracellular pathogen infection (e.g., a chronic infection), and/or reducing the number of inflicted cells (e.g., cancer cells, cells infected with an intracellular pathogen, etc.) in an individual, includes, as described below, predicting whether an individual is resistant or susceptible to treatment with an anti-CD47/SIRPA agent.

Methods of Predicting

As discussed above, in some cases, a target cell (even one that expressed CD47) is relatively resistant to an anti-CD47/SIRPA agent, meaning that the target cell is less susceptible to phagocytois by a phagocytic cell (e.g., a macrophage), even when the target cell is contacted by a phagocytic cell in the present of an anti-CD47/SIRPA agent. As such, in some cases, an individual (e.g, an individual having inflicted cells, e.g., cancer cells and/or infected cells) can be relatively resistant to treatment with an anti-CD47/SIRPA agent. Also as described above, and as described below in the working examples, the inventors have discovered that the level of expression of MHC Class I (e.g., classical MHC Class I) by an inflicted cell (eg., on the cell surface) can be used to predict whether a target cell (and therefore whether an individual) is resistant to treatment using an anti-CD47/SIRPA agent. In this context, resistance to treatment using an anti-CD47/SIRPA agent refers to treatment in the absence of a subject anti-MHC Class I/LILRB1 agent, because the inventors have discovered that contacting a target cell (e.g., a target cell that is resistant to treatment with an anti-CD47/SIRPA agent) with an anti-MHC Class I/LILRB1 agent can overcome the resistance.

The terms "resistance" and "resistant" (used herein when referring to resistance to an anti-CD47/SIRPA agent) is used herein to refer to target cells that exhibit a decrease in the susceptibility to phagocytosis (in the present of an anti-CD47/SIRPA agent) compared to other cells. For example, while many cancer cells are negative for (or express low levels of) MHC Class I (e.g., classical MHC Class I), some cancer cells are positive for MHC Class I (e.g., classical MHC Class I). Target cells (e.g., cancer cells) can express MHC Class I (e.g., classical MHC Class I) over a range of levels. For example, some target cells express more MHC Class I (e.g., classical MHC Class I) than others, but still express less than normal cells. Some target cells express normal levels of MHC Class I. The inventors have discovered that the level of MHC Class I expressed by a target cell correlates with its susceptibility to phagocytosis by a phagocytic cell (e.g., a macrophage). Thus, when the term "resistance" or "resistant" is used, it does not necessarily mean that the cells cannot be phagocytosed, but does mean that the cells are not phagocytosed as efficiently as other cells (e.g., a smaller proportion of cells of a population of the cells can be phagocytosed, e.g., over a given period of time, when compared to other cells).

In some embodiments, a target cell that is resistant to treatment with an anti-CD47/SIRPA agent exhibits a phagocytosis efficiency that is 95% or less (e.g., 90% or less, 85% or less, 80% or less, 75% or less, 70% or less, 65% or less, 60% or less, 55% or less, 50% or less, 45% or less, 50% or less, 45% or less, 40% or less, 35% or less, 30% or less, 25% or less, 20% or less, 15% or less, or 10% or less) of the phagocytosis efficiency exhibited by a control cell (e.g., a control population of cells). In this context, a control cell can be any target cell that expresses CD47 and is phagocytosed when contacted with: (i) a phagocytic cell (e.g., a macrophage), and (ii) an anti-CD47/SIRPA agent. For example, in some cases, a control cell in this context is a cancer cell line known to be susceptible to an anti-CD47/SIRPA agent. Assays to determine phagocytosis efficiency will be known to one of ordinary skill in the art and any convenient assay can be used. For example, see the working examples below (e.g., see FIG. 1B). As such, an individual can be predicted to be resistant to treatment with an anti-CD47/SIRPA agent when a target cell exhibits an MHC Class I expression level that is above a particular threshold (which can be determined by comparing the measured expression level to a level measured from a control cell that is susceptible to treatment with an anti-CD47/SIRPA agent.

In some embodiments, a target cell (or an individual) is predicted to be susceptible to an anti-CD47/SIRPA agent when the target cell expresses 95% or less (e.g., 90% or less, 85% or less, 80% or less, 75% or less, 70% or less, 65% or less, 60% or less, 55% or less, 50% or less, 45% or less, 50% or less, 45% or less, 40% or less, 35% or less, 30% or less, 25% or less, 20% or less, 15% or less, or 10% or less) MHC Class I as expressed by a control cell (e.g., a normal cell). In some cases, a target cell (or an individual) is predicted to be resistant to an anti-CD47/SIRPA agent when the target cell expresses 1.1-fold or more (e.g., 1.2-fold or more, 1.3-fold or more, 1.4-fold or more, 1.5-fold or more, 1.6-fold or more, 1.7-fold or more, 1.8-fold or more, 1.9-fold or more, 2-fold or more, 2.1-fold or more, 2.5-fold or more, 3-fold or more, 4-fold or more, 5-fold or more, etc.) MHC Class I compared to a control cell (e.g., an MHC Class I negative cell, a cell that expresses low levels of MHC Class I but is known to be susceptible, and the like) or compared to a background value.

Methods of predicting whether target cells are (or an individual is) resistant or susceptible to treatment with an anti-CD47/SIRPA agent include the step of measuring the expression level of Major Histocompatibility Complex (MHC) Class I in a biological sample of the individual (e.g., where the biological sample comprises an inflicted cell such as a cancer cell or a cell harboring an intracellular pathogen), to produce a measured test value. The measured test value can then be compared to a control value. In some cases, the value is measured for individual cells (e.g., using flow cytometry).

In some cases, when the measured test value is greater than or equal to the control value, a prediction of resistance is made (and when the measured test value is less than the control value, a prediction of susceptible is made). The control value can be a predetermined value or can be a value that is measured around the same time that the test value is measured. In some cases, the control value is a value of expression which is known to be associated with a phenotype of resistance to an anti-CD47/SIRPA agent. As such, when the measured test value is equal to or greater than this value, a prediction of resistance can be made. Such a control value (one that is known to be associated with a phenotype of resistance to an anti-CD47/SIRPA agent) can be a value measured from an inflicted cell known to exhibit a phenotype of resistance.

In some cases, when the measured test value is greater than the control value, a prediction of resistance is made (and when the measured test value is less than or equal to the control value, a prediction of susceptible is made). The control value can be a predetermined value or can be a value that is measured at or around the same time that the test value is measured. In some cases, the control value is a value representing the background value of the measuring step (e.g., the experiment in which the measurement was performed). For example, in some cases, for a cell to exhibit a phenotype of resistance, the cell only needs to be positive for MHC Class I (e.g., classical MHC Class I).

Thus, in some cases, a method of predicting whether a target cell (or an individual) is resistant to treatment with an anti-CD47/SIRPA agent includes measuring the expression level of Major Histocompatibility Complex (MHC) Class I (e.g., in a biological sample of the individual that contains an inflicted cell), determining that the target cell (or an inflicted cell of the individual) is positive for MHC Class I (e.g., classical MHC Class I), and predicting that the target cell (or individual) is resistant to treatment with an anti-CD47/SIRPA agent. In some cases, a method of predicting whether a target cell (or an individual) is resistant to treatment with an anti-CD47/SIRPA agent includes measuring the expression level of Major Histocompatibility Complex (MHC) Class I (e.g., in a biological sample of the individual that contains an inflicted cell), determining that the target cell (or an inflicted cell of the individual) expresses an increased level of MHC Class I (e.g., classical MHC Class I) compared to a control value, and predicting that the target cell (or individual) is resistant to treatment with an anti-CD47/SIRPA agent.

In some cases, the level of MHC Class I expression is predictive of how resistant a cell (or an individual) is to an anti-CD47/SIRPA agent. Thus, in some cases, the method is a method of predicting the level of resistance of a target cell (or an individual) to treatment with an anti-CD47/SIRPA agent, and the method can include: measuring the expression level of Major Histocompatibility Complex (MHC) Class I (e.g., in a biological sample of the individual that contains an inflicted cell), comparing the measured level of MHC Class I with a control value, and predicting that level of resistance of the target cell (or individual) to treatment with an anti-CD47/SIRPA agent.

In some cases, a method of predicting whether a target cell (or an individual) is resistant to treatment with an anti-CD47/SIRPA agent includes measuring the expression level of Major Histocompatibility Complex (MHC) Class I (e.g., in a biological sample of the individual that contains an inflicted cell), determining that the target cell (or an inflicted cell of the individual) is negative for MHC Class I (e.g., classical MHC Class I), and predicting that the target cell (or individual) is not resistant to (i.e., is susceptible to) treatment with an anti-CD47/SIRPA agent. In some cases, a method of predicting whether a target cell (or an individual) is resistant to treatment with an anti-CD47/SIRPA agent includes measuring the expression level of Major Histocompatibility Complex (MHC) Class I (e.g., in a biological sample of the individual that contains an inflicted cell), determining that the target cell (or an inflicted cell of the individual) expresses a decreased level of MHC Class I (e.g., classical MHC Class I) compared to a control value, and predicting that the target cell (or individual) is not resistant to (i.e., is susceptible to) treatment with an anti-CD47/SIRPA agent.

In some cases, when a prediction of resistance is made, the method further includes treating the individual (i.e., contacting the target cell(s)) with an anti-MHC Class I/LILRB1 agent and an anti-CD47/SIRPA agent (e.g., co-administration to the individual, contacting the target cell with a phagocytic cell in vitro in the presence of an anti-MHC Class I/LILRB1 agent and an anti-CD47/SIRPA agent, etc.).

The terms "determining", "measuring", "evaluating", "assessing," "assaying," and "analyzing" are used interchangeably herein to refer to any form of measurement, and include determining if an element is present or not. These terms include both quantitative and/or qualitative determinations. Measuring may be relative or absolute. For example, "measuring" can be determining whether the expression level is less than or "greater than or equal to" a particular threshold, (the threshold can be pre-determined or can be determined by assaying a control sample). On the other hand, "measuring to determine the expression level" can mean determining a quantitative value (using any convenient metric) that represents the level of expression (i.e., expression level, e.g., the amount of protein and/or RNA, e.g., mRNA) of a particular biomarker. The level of expression can be expressed in arbitrary units associated with a particular assay (e.g., fluorescence units, e.g., mean fluorescence intensity (MFI)), or can be expressed as an absolute value with defined units (e.g., number of mRNA transcripts, number of protein molecules, concentration of protein, etc.). Additionally, the level of expression of a biomarker can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple biological samples from the same individual (e.g., biological samples taken at different points in time from the same individual). This is because the units cancel when calculating a fold-change in the expression level from one biological sample to then next (e.g., biological samples taken at different points in time from the same individual).

The term "measuring" is used herein to include the physical steps of manipulating a biological sample to generate data related to the sample. As will be readily understood by one of ordinary skill in the art, a biological sample must be "obtained" prior to assaying the sample. Thus, the term "measuring" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample. In some cases, the measured expression level of MHC Class I is normalized (e.g., to an internal experimental control).

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

In subject methods, the expression level of a gene product (e.g., a biomarker) in a biological sample is measured (i.e., "determined"). By "expression level" it is meant the level of gene product (e.g. the absolute and/or normalized value determined for the protein expression level, and/or the RNA expression level of a biomarker). The term "gene product" or "expression product" are used herein to refer to the protein products or RNA transcription products (RNA transcripts, e.g. mRNA, an unspliced RNA, a splice variant mRNA, and/or a fragmented RNA) of a gene, including mRNA, and the polypeptide translation products of such RNA transcripts. A gene product can be, for example, a protein, a post-translationally modified polypeptide, a splice variant polypeptide, an unspliced RNA, an mRNA, a splice variant mRNA, a microRNA, a fragmented RNA, etc.

The biomarker used herein is MHC Class I (e.g., classical MHC Class I). Thus, "measuring the expression level" generally entails measuring the expression level of MHC Class I (e.g., classical MHC Class I) on or in a cell. In some cases, the methods include measuring the expression level of MHC Class I (e.g., classical MHC Class I) on the surface of a cell (e.g., via flow cytometry). In some cases, the methods include measuring the expression level of MHC Class I (e.g., classical MHC Class I) in a cell (e.g., via Western Blot, ELISA assay, mass spectrometry, etc).

For measuring protein levels, the amount or level of a polypeptide in the biological sample is determined, e.g., the protein/polypeptide encoded by the biomarker gene. In some cases, the surface protein level is measured. In some cases, the cells are removed from the biological sample (e.g., via centrifugation, via adhering cells to a dish or to plastic, etc.) prior to measuring the expression level. In some cases, the intracellular protein level is measured (e.g., by lysing the cells of the biological sample to measure the level of protein in the cellular contents). In some cases, cells of the biological sample are identified as target cells (e.g., inflicted cells) (e.g., via cell sorting, via microscopic evaluation, via marker analysis, etc.) prior to measuring the expression level of MHC Class I. In some cases, cells of the biological sample are identified as target cells simultaneous with measuring the expression level of MHC Class I (e.g., via flow cytometry). In some cases, surface levels of MHC Class I can be measured by extracting or otherwise enriching for or purifying surface proteins, prior to the measuring.

In some instances, the expression level of one or more additional proteins may also be measured, and the level of biomarker expression compared to the level of the one or more additional proteins to provide a normalized value for the biomarker expression level. Any convenient protocol for evaluating protein levels may be employed wherein the level of one or more proteins in the assayed sample is determined.

While a variety of different manners of assaying for protein levels are known to one of ordinary skill in the art and any convenient method may be used, representative methods include but are not limited to antibody-based methods (e.g., flow cytometry, ELISA, Western blotting, proteomic arrays, xMAP™ microsphere technology (e.g., Luminex technology), immunohistochemistry, flow cytometry, and the like); as well as non antibody-based methods (e.g., mass spectrometry).

When a prediction is made in the subject methods, the methods include a step of providing the prediction. The term "providing a prediction" is not simply a mental step, but instead includes the active step of reporting the prediction either by generating or report, or by orally providing the prediction. In some cases the prediction is provided as a report. Thus, in some instances, the subject methods may further include a step of generating or outputting a report providing the results of the evaluation of the sample, which report can be provided in the form of a non-transient electronic medium (e.g., an electronic display on a computer monitor, stored in memory, etc.), or in the form of a tangible medium (e.g., a report printed on paper or other tangible medium). Any form of report may be provided, e.g. as known in the art or as described in greater detail below.

In some embodiments, a report is generated. A "report," as described herein, is an electronic or tangible document which includes report elements that provide information of interest relating to the assessment of a subject and its results. In some embodiments, a subject report includes the measured test value that represents the measured expression level of MHC Class I (e.g., the normalized measured expression level). In some embodiments, a subject report includes an artisan's assessment, e.g. a prediction of resistance or susceptibility, a treatment recommendation, a prescription, etc. A subject report can be completely or partially electronically generated. A subject report can further include one or more of: 1) information regarding the testing facility; 2) service provider information; 3) patient data; 4) sample data; 5) an assessment report, which can include various information including: a) reference values employed, and b) test data, where test data can include, e.g., a protein level determination; 6) other features.

In some embodiments, a prediction is provided by generating a written report. Thus, the subject methods may include a step of generating or outputting a report, which report can be provided in the form of an electronic medium (e.g., an electronic display on a computer monitor), or in the form of a tangible medium (e.g., a report printed on paper or other tangible medium). Any form of report may be provided.

The report may include a sample data section, which may provide information about the biological sample analyzed in the monitoring assessment, such as the source of biological sample obtained from the patient (e.g. Tumor, blood, saliva, or type of tissue, etc.), how the sample was handled (e.g. storage temperature, preparatory protocols) and the date and time collected. Report fields with this information can generally be populated using data entered by the user, some of which may be provided as pre-scripted selections (e.g., using a drop-down menu). The report may include a results section. For example, the report may include a section reporting the results of a marker expression level determination assay, or a prediction of resistance or susceptibility.

Kits

Also provided are kits for use in the methods. The subject kits can include an anti-MHC ClassI/LILRB1 agent and/or an anti-CD47/SIRPA agent. In some embodiments, a kit comprises two or more anti-MHC ClassI/LILRB1 agents and/or two or more anti-CD47/SIRPA agents. In some embodiments, an anti-MHC ClassI/LILRB1 agent and/or an anti-CD47/SIRPA agent is provided in a dosage form (e.g., a therapeutically effective dosage form, a sub-therapeutic dosage form, e.g., in the case of an anti-CD47/SIRPA agent). In the context of a kit, an anti-MHC ClassI/LILRB1 agent and/or an anti-CD47/SIRPA agent can be provided in liquid or sold form in any convenient packaging (e.g., stick pack, dose pack, etc.). The agents of a kit can be present in the same or separate containers. For example, a kit may have an anti-MHC ClassI/LILRB1 agent in one container and an anti-CD47/SIRPA agent in another container. The agents may also be present in the same container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1

The experiments here show that MHC class I, which is among the most intensely studied regulatory complexes in immunology due to its function in signaling to T and NK cells, plays a previously unappreciated role in protecting cells from attack by macrophages. The results demonstrate that MHC class I expression inhibits macrophage-mediated phagocytosis of cells, both in vitro and in vivo. Macrophage recognition of MHC class I is shown to be specifically mediated by the surface receptor LILRB1. Biologic anti-LILRB1 agents, aimed either at MHC class I or at LILRB1, are sufficient to disrupt this protection, thus defining the MHC/LILRB1 signaling axis as an important mediator of innate immune regulation and a target for therapy (e.g., anti-cancer immunotherapy).

Materials and Methods

Cell Culture

DLD-1, NCI-H69, NCI-H82, NCI-H1688, NCI-H196, NCI-H524, Bon, and KWNO1 cells were grown in RPMI+GlutaMax (Life Technologies) supplemented with 10% fetal bovine serum (Hyclone), and 100 U/mL penicillin and streptomycin (Life Technologies). NCI-H128 was grown in RPMI+GlutaMax (Life Technologies) supplemented with 20% fetal bovine serum (Hyclone), and 100 U/mL penicillin and streptomycin (Life Technologies). HT-29, SkBr3, and SkMel3 were grown in McCoy's 5A+GlutaMax (Life Technologies) supplemented with 10% fetal bovine serum (Hyclone), and 100 U/mL penicillin and streptomycin (Life Technologies). LS-174T, MCF7, and SkMel28 were grown in Eagle's Minimum Essential Media (ATCC) supplemented with GlutaMax (Life Technologies) 10% fetal bovine serum (Hyclone), and 100 U/mL penicillin and streptomycin (Life Technologies). When necessary, cells were detached from plates and disaggregated using TrypLE Express (Life Technologies) according to the manufacturer's indications. All cell lines were obtained from ATCC with the exception of KWNO1, which was a generous gift from Geoff Krampitz at Stanford University. Unless otherwise indicated, cell lines were propagated and subcultured according to ATCC guidelines.

Generation of Lentiviral Particles

HIV-based replication incompetent lentiviral particles were generated in 293 Lenti-X cells (Clontech) by co-transfection of pMDG.2 vector (Addgene), psPAX2 (Addgene), and a third vector specific to the lentiviral application, using the Xtremegene HD transfection reagent (Roche) according to the manufacturer's protocol. Vectors were transfected at a mass ratio of 4:2:1, lenti-specific vector: psPAX2: pMDG.2. After transfection, cell culture media supernatant was collected at 36 hours and 60 hours. Lentiviral particles were concentrated either by ultracentrifugation for 2.5 hours at 50,000 g, or with PEG-it (Systems Biosciences) according to the manufacturer's indications. Proper biosafety and disposal techniques were followed whenever using lentiviral reagents, according to Stanford University guidelines.

GFP-Luciferase Transduction

In order to facilitate both the FACS-based phagocytosis assay and in vivo imaging, sublines of DLD1, HT-29, LS-174T, SkBr3, Bon, KWNO1, SkMel28, and SkMel3 were generated that were engineered to stably express a GFP-luciferase fusion protein (Systems Biosciences, catalog number BLIV100PA/VA-1). U2OS and SAOS2 were engineered to stably express an RFP-luciferase fusion protein (Systems Biosciences, catalog number BLIV101PA/VA-1). Parental, unmodified cells were harvested in single-cell suspension and mixed with pre-warmed growth media, concentrated lentivirus, and 10 ug/ml polybrene (Sigma). Cells were then centrifuged at 800 rpm, room temperature for 1 hour. Uniform GFP+ or RFP+ populations were then generated by sequential rounds of cell sorting on a FACSAria II cell sorter (BD Biosciences).

Macrophage Generation

Leukocyte reduction system (LRS) chambers from anonymous donors were obtained from the Stanford Blood Center. Monocytes were purified from these samples on an autoMACS Pro Separator (Miltenyi) using anti-CD14 microbeads optimized for whole blood separation (Miltenyi) according to the manufacturer's suggested protocol. Monocytes were then differentiated to macrophages by 7-10 days of culture in IMDM+GlutaMax (Life Technologies) supplemented with 10% AB Human Serum (Life Technologies) and 100 U/ml penicillin and streptomycin (Life Technologies). NSG macrophages were generated as previously described. Briefly, bone marrow cells were harvested from the lower limbs of 6-8 week old NSG mice, and cultured for 7 days in IMDM+GlutaMax[13] (Life Technologies) supplemented with 10% fetal bovine serum (Hyclone), 100 U/mL penicillin and streptomycin, and 10 ng/mL murine M-CSF (Peprotech).

FACS-Based Phagocytosis Assay

Each phagocytosis reaction reported in this work was performed by co-culture of 100,000 target cells and 50,000 macrophages for two hours in ultra-low attachment 96 well U-bottom plates (Corning) in IMDM+GlutaMax (Life Technologies) without antibiotics or serum added. Macrophages were generated as described above, and harvested from plates using TrypLE Express (Life Technologies). Target cells were either engineered to stably express GFP or RFP fluorescent protein, as described above, or stained with Calcein AM (Life Technologies) according to the manufacturer's indications prior to co-culture. Treatment antibodies, including anti-CD47 clone Hu5F9-G4, cetuximab (Bristoll-Myers Squibb), anti-LILRB1 clone GHI/75 (BioLegend), and anti-LILRB2 clone 27D2 (Biolegend) were added to reactions at a concentration of 10 ug/ml. After co-culture, reactions were stained were stained with APC-labeled anti-CD45 clone H130 (BioLegend) to identify human macrophages, and with PE-Cy7-labeled anti-F4/80 clone BM8 (BioLegend) to identify NSG mouse macrophages. DAPI staining was used to exclude dead cells from the analysis (Sigma). Reactions were run on an LSRFortessa Analyzer outfitted with a high-throughput auto-sampler (BD Biosciences). Phagocytosis was evaluated as the percentage of GFP+ macrophages using FlowJo v.9.4.10 (Tree Star) and was normalized as indicated in the figure legends.

Antibody Array

The LegendScreen antibody array system (BioLegend) was used to assess the surface phenotype of the NCI-H69, NCI-H82, NCI-H524, and NCI-H196 cell lines. The cells were harvested and disaggregated with TrypLE (Life Technologies), and NCI-H82 and NCI-H69 were stained using Calcein AM (Life Technologies) according to the manufacturer's protocol. NCI-H82 (calcein-stained) and NCI-H524 (unstained) cells were run together in a multiplexed fashion, as were NCI-H69 (calcein-stained) and NCI-H196 (unstained). Cells were distributed amongst antibody-containing wells, stained, and washed according to the manufacturer's indications. Samples were subsequently run on an LSRFortessa Analyzer outfitted with a high-throughput auto-sampler (BD Biosciences). Fluorescence levels were evaluated using FlowJo v.9.4.10 (Tree Star). Calcein staining signal was used to deconvolute multiplexed samples.

Antibody Staining

FACS analysis was performed either on a FACSAria II cell sorter (BD Biosciences) or on an LSRFortessa Analyzer (BD Biosciences). Surface CD47 levels were assessed by antibody staining with clone B6H12 (BioLegend) at a dilution of 1:100. HLA-A/B/C was assessed by antibody staining with clone W6/32 (BioLegend) at a dilution of 1:50. LILRB1 was assessed by antibody staining with clone GHI/75 (BioLegend) at a dilution of 1:25. LILRB2 was assessed by antibody staining with clone 27D2 (BioLegend) at a dilution of 1:25. All stains were performed on ice for 30 minutes, then washed and resuspended according to standard practice.

DLD1 Genetic Modifications

Unmodified DLD1 cells (ATCC) were transduced with lentivirus to induce stable expression of GFP-luciferase fusion protein (Systems Biosciences, catalog number BLIV100PA/VA-1), as described above and sorted for purity using a FACSAria II cell sorter (BD Biosciences). Sequential genetic changes were introduced into this GFP-luciferase+ parental line. Wild-type human B2M (NC_000015.10), wild-type mouse B2m (NC_000068.7), or chimeric human-mouse B2M (hmcB2M; see below for sequence) were cloned into the NheI and NotI sites of the pCDH-CMV-MCS-EF1-Puro vector (Systems Biosciences), and these vectors were used to produce lentivirus, as described above. DLD1 cells were transduced with these viral particles to produce DLD1-Tg(B2M), DLD1-Tg(mB2m), and DLD1-Tg(hmcB2M), respectively. DLD1-Δ (CD47) was generated by transient co-transfection of CD47-targeting TALEN vectors, described below, using Xtremegene HD (Roche) according to the manufacturer's indicated protocol, stained for CD47 expression using antibody clone B6H12 (BioLegend), and sorted for purity using a FACSAria II cell sorter (BD Biosciences). DLD1-Tg (B2M)-Δ(CD47) was generated by transduction of human B2M-encoding lentivirus into the DLD1-Δ(CD47) sub-line.

TALEN Design and Construction

TALENs were designed and assembled as described[29]. The genomic locus of human CD47 (NC_000003.12) was scanned for putative TALEN binding pairs. Exon 2 was ultimately selected for targeting and the TALEN pairs TGTCGTCATTCCATGCTTTG (SEQ ID NO: 15) and TATACTTCAGTAGTGTTTTG (SEQ ID NO: 16) were respectively cloned into the pTALEN backbone.

Human-Mouse Chimeric B2M

Chimeric B2M was designed to incorporate C-terminal amino acid differences from mouse B2m into a primarily human B2M sequence. The sequence was chemically synthesized as follows (IDT), and cloned into the NheI and NotI sites of pCDH-CMV-MCS-EF1-Puro. Sequence of mouse origin is in lower case.

```
>hmcB2M_geneblock
                                     (SEQ IS NO: 17)
TTTAAGCTAGCATGTCTCGCTCCGTGGCCTTAGCTGTGCTCGCGCTACT

CTCTCTTTCTGGCCTGGAGGCTATCCAGCGTACTCCAAAGATTCAGGTT

TACTCACGTCATCCAGCAGAGAATGGAAAGTCAAATTTCCTGAATTGCT

ATGTGTCTGGGTTTCATCCATCCGACATTGAAGTTGACTTACTGAAGAA

TGGAGAGAGAATTGAAAAAGTGGAGCATTCAGACTTGTCTTTCAGCAAG

GACTGGTCTTTCTATCTCTTGTACTACACTGAATTCACCCCCACTGAAA

AAGATGAGTATGCCtgcagagttaagcatgccagtatggccgagcccaa gaccgtctactgggatcgagacatgtgaGCGGCCGCAATTT
```

Generation of W6/32 Fab Fragments

W6/32 antibody (BioXcell) was desalted into a solution of 20 mM sodium citrate pH 6.0, 25 mM cysteine, 5 mM EDTA, and diluted to a concentration of 4 mg/mL. Protease digestion was achieved by mixing with 250 ul immobilized ficin resin (Thermo Scientific) per mL of antibody. The mixture was incubated with rotation at 37° C. for 5 hours. After incubation, the resulting digestion reaction was passed over a monoQ column, and the flow-through was collected and filtered through a Superdex-200 column. Fab fragments were quantified by Nanodrop, and checked for purity by coomassie stain.

Crystal Structure Images

Crystal structure images were generated with MacPyMol v. 1.7.0.3 from the published structure IP7Q.

Mice

Nod.Cg-Prkdc$^{scid}$ IL2rg$^{tm1 Wjl}$/SzJ (NSG) mice were used for all in vivo experiments. Mice were engrafted with tumors at approximately 6-10 weeks of age, and experiments were performed with an age and sex-matched cohort of 15 mice. Mice were maintained in a barrier facility under the care of the Stanford Veterinary Services Center and handled according to protocols approved by the Stanford University Administrative Panel on Laboratory Animal Care.

In Vivo Competition of DLD1 Sublines

DLD1 cells and DLD1-Tg(hmcB2M) cells were generated as detailed above. Cells were harvested from culture, counted, mixed in equal quantities, and FACS analyzed on a FACSAria II cell sorter (BD Biosciences) to confirm approximately equal representation. Cells were then mixed with a solution of 25% low-protein matrigel (BD Biosciences) and 75% unsupplemented RPMI (Life Technologies) to a concentration of $1\times10^6$ cells/mL. Mice were injected subcutaneously in their right flank with 100 μL of cell suspension (100,000 cells), and randomly assigned to an analysis time-point using the list randomization tools at www.random.org. At 7 days, 14 days, and 28 days, 5 mice per time point were sacrificed according to Stanford Administrative Panel on Laboratory Care guidelines. Tumors were dissected from surrounding mouse tissue with the aid of a Leica M165 fluorescent dissection microscope (Leica), and dissociated as previously described. Single cell suspensions were washed, stained with W6/32 antibody as described above, and analyzed using either a FACSAria II cell sorter or an LSRFortessa Analyzer (BD Biosciences).

Results

When donor-derived human macrophages are co-cultured with cancer cells, treatment with the humanized anti-CD47 antibody (Hu5F9-G4) induced a significant increase in macrophage phagocytosis for a majority (12 of 18) of cell lines spanning a wide variety of tumor types. However, some lines did not significantly respond to anti-CD47 therapy (6 of 18), and furthermore, amongst those with significant responses the magnitude of induced phagocytosis differed widely. These differences did not correlate with differences in surface CD47 levels, which were high in all cell lines tested.

Based on this observation, the resistant cell lines were hypothesized to express one or more dominant "don't eat me" signals in addition to CD47. In order to identify these signals, an antibody array system was used to characterize the surface immunophenotype of four small cell lung cancer lines (NCI-H69, NCI-H524, NCI-H82, and NCI-H196) that span a broad spectrum of response to Hu5F9-G4 treatment, from highly sensitive to almost completely resistant. The most resistant cell line of this panel, NCI-H196, expressed high levels of the surface molecules HLA-A/B/C and B2M.

HLA alpha chains and B2M protein assemble to form the classical MHC class I complex, which has critical roles in T cell and NK cell regulation. Analysis of HLA-A/B/C expression in an extended panel of 18 cell lines revealed a striking and highly significant inverse correlation between surface levels of MHC class I and sensitivity to macrophage-mediated phagocytosis upon Hu5F9-G4 treatment ($R^2=0.411$, $p=0.002$).

In order to investigate whether MHC class I expression directly confers a functional resistance to macrophage-mediated phagocytosis, a series of genetic experiments were designed and executed that utilize the colon cancer line DLD1. This cell line expresses CD47 but is fully negative for surface MHC class I expression due to biallelic genetic inactivation of the B2M locus. Surface MHC class I expression can be experimentally restored by lentiviral expression of wild-type B2M, whereas CD47 expression can be eliminated through TALEN-induced mutation of the CD47 locus. Thus, by sequential genetic modifications, sub-lines of DLD1 were generated with all four possible permutations of positive or negative MHC class I and CD47 expression.

A comparison of parental DLD1 and B2M reconstituted DLD1-Tg(B2M) cells revealed that restoration of surface MHC class I was sufficient to significantly protect cells from Hu5F9-G4-induced macrophage phagocytosis ($p<2\times10^{-5}$). Analysis of the full allelic series of DLD1 demonstrated that double-negative cells lacking both CD47 and MHC expression were the most vulnerable to phagocytosis upon treatment with the anti-EGFR antibody cetuximab, while expression of MHC class I was significantly protective ($p<0.001$). CD47 expression inhibited macrophage attack to an even greater degree ($p<0.001$). These results demonstrate that MHC class I is an important inhibitor of macrophage phagocytosis, particularly under conditions of compromised CD47 signaling.

These data suggested that in cell lines expressing high levels of MHC, disruption of this signaling axis might potentiate phagocytosis. To this end, a fragment of antigen binding (Fab) from the pan-HLA-A/B/C monoclonal antibody W6/32[19] was generated. Unlike the intact antibody, the W6/32 Fab binds MHC class I without introducing opsonization in the form of Fc, allowing the examination of the consequences of its blocking function in isolation. The anti-HLA-A/B/C Fab did not significantly increase phagocytosis on its own for any cell lines tested, nor did it increase the Hu5F9-G4-induced phagocytosis of the MHC-negative cell line DLD1. Nonetheless, in a panel of cell lines expressing high levels of MHC co-treatment with the HLA-binding W6/32 fab significantly increased the effectiveness of anti-CD47 antibody for the majority of lines. These results demonstrate that MHC-blocking agents can potentiate macrophage-mediated attack of otherwise resistant cancers.

In order to further understand the mechanism by which macrophages might detect the MHC expression status of target cells, the identity of the receptor or receptors involved in this process were sought. Monocyte lineages have been reported to express a number of MHC- binding proteins, notably members of the LILRA and LILRB family. Structural studies suggest that amongst this family, only two genes, LILRB1 and LILRB2, possess both MHC binding capacity and the ITIM motifs involved in intracellular transduction of repressive signaling that would be necessary to account for our experimental results.

FACS analysis of freshly isolated CD14+ human peripheral blood monocytes from four independent donors revealed that these cells express both LILRB1 and LILRB2 to some extent. However, after 7 days of ex vivo differentiation into mature macrophages, these same cell populations significantly increased their expression of LILRB1 but lost expression of LILRB2 ($p<0.001$). This observation implicates LILRB1—but not LILRB2—as a candidate mediator of repressive MHC signaling in macrophages.

It was therefore tested whether a LILRB1 blocking antibody could induce macrophages to phagocytose MHC-expressing cells. Indeed, while reconstitution of DLD1 with wild-type B2M significantly protected these cells from Hu5F9-G4-directed macrophage attack, disrupting either LILRB1 (using blocking antibody GHI/75) or HLA-A/B/C (using blocking W6/32 fab) was sufficient to facilitate phagocytosis and completely eliminate the protective effect of MHC expression. Conversely, treatment with a LILRB2 blocking antibody, 27D2, had no significant effect on Hu5F9-G4-directed phagocytosis.

All phagocytosis assays reported in this study utilized macrophages derived from multiple independent biological donors, with no prior analysis or selection based on HLA haplotype; despite this, no evidence of a polymorphism-based variable response to MHC- mediated protection was uncovered. This suggests that macrophages employ a different paradigm of MHC detection than that utilized by T cells and NK cells. Consistent with this observation, analysis of the crystal structure of LILRB1 bound to the human MHC class I complex revealed that the majority of amino acid contacts between LILRB1 and MHC are within the invariant B2M subunit, rather than the highly polymorphic HLA alpha chain.

By contrast to HLA alpha chains, human B2M is minimally polymorphic between individuals, but alignment of the human and mouse B2M protein sequences reveals ~30% mismatch, including a number of residues in the predicted interface between B2M and LILRB1. Given this difference, it was tested whether mouse B2M expression could endow protection against human macrophage attack. Mouse B2M overexpression in human DLD1 cells failed to deter phagocytosis by human macrophages, but this result was confounded by the low efficiency with which mouse B2M returned stable MHC complexes to the cell surface. To circumvent this technical limitation, a human-mouse chimeric B2M (hmcB2M) was generated that is primarily human but is mutated to include eight C-terminal amino acids of mouse sequence in the region predicted to interact with LILRB1. Expression of hmcB2M induces robust surface expression of HLA-A/B/C comparable to fully human B2M, but unlike human B2M it has no protective effect against attack by human macrophages. This result genetically demonstrates that the B2M/LILRB1 interface is critical for macrophage detection of MHC. In contrast, when DLD1 sublines were co-cultured with mouse macrophages, hmcB2M was the only tested version of B2M that significantly protected from phagocytosis.

To test the in vivo consequences of MHC signaling on macrophage phagocytosis, and in particular, to determine whether MHC expression by cancer cells could confer a competitive advantage over MHC negative cancer cells in vivo, NSG (NOD-SCID II2r$\gamma^{-/-}$) mice, which produce functional macrophages but lack functional T, B and NK cells, were utilized. NSG mice were subcutaneously injected with a mixed population of cells comprising 50% parental (MHC-) DLD1 and 50% hmcB2M-reconstituted (MHC+) DLD1. Although engrafted tumors initially contained approximately equal percentages of MHC+ and MHC- cells (pre-injection and day 7), after several weeks of growth, the tumors were almost uniformly MHC positive (day 28). This implies that MHC-expressing cells are subject to a significantly reduced degree of macrophage immunosurveillance in vivo. This is unlikely to be a cell-autonomous advantage, as the hmcB2M-reconstituted DLD1 sub-line does not show any significant difference in growth kinetics in vitro when compared to parental DLD1 cells. Moreover, administration of Hu5F9-G4 (anti-CD47 antibody) slowed the growth of DLD1 cells in vivo (which are MHC- due to lack of B2M expression), but had no significant effect on DLD1-Tg (hmcB2M) cells, which express B2M and are MHC+.

Example 2

The results presented here demonstrate that MHC class I expression by cancer cells directly inhibits macrophage-mediated phagocytosis, and further show that macrophage detection of MHC class I is mediated by the inhibitory surface receptor LILRB1. Biologic agents aimed either at MHC class I or at LILRB1 were sufficient to disrupt this protection and potentiate macrophage attack in vitro and in vivo, thus defining the MHC:LILRB1 signaling axis as not only an important regulator of macrophage effector function, but also a biomarker for therapeutic response to anti-CD47 agents, and a target for anti-cancer immunotherapy. Some of the results presented in example 2 are also presented in Example 1 above.

Results

Expression of MHC Class I Correlates with Resistance to Macrophage Phagocytosis

Figure 1A:
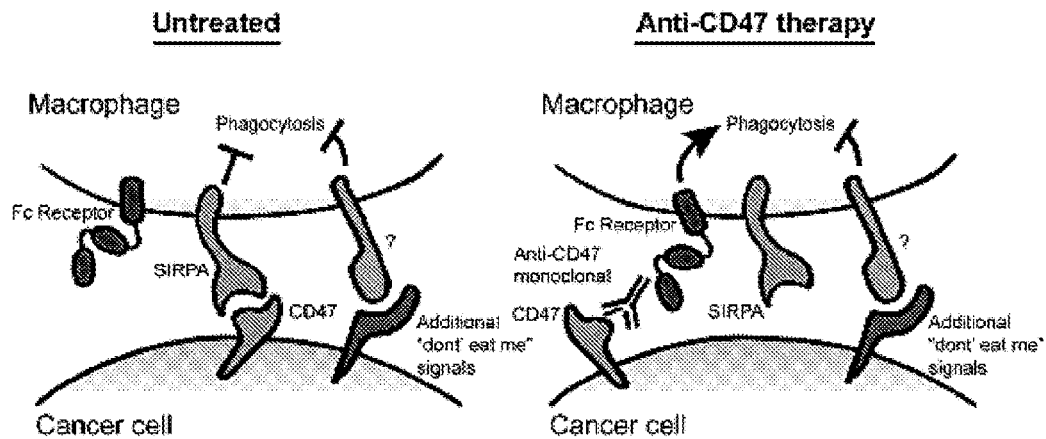
Figure 1B:
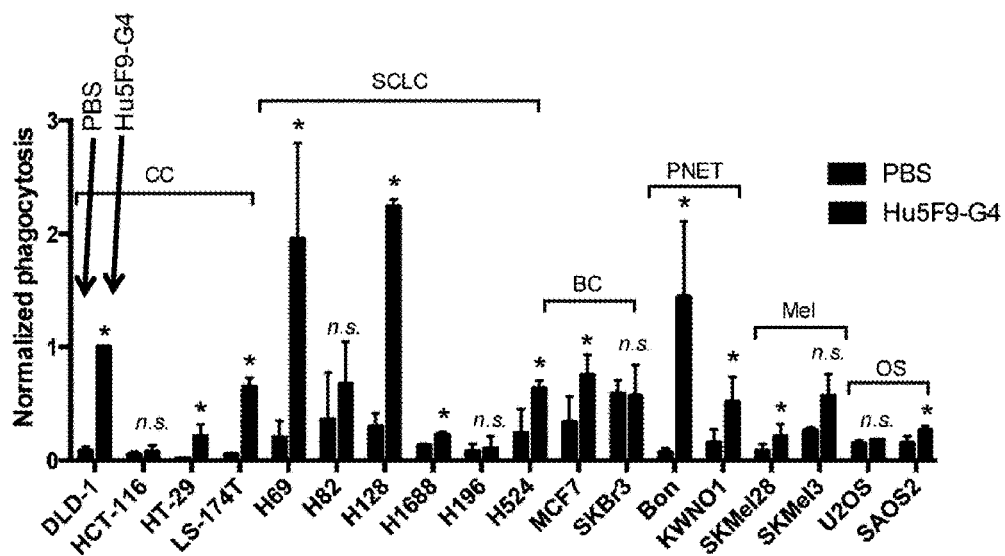

Drugs against the CD47:SIRPA pathway have broad efficacy to induce phagocytosis of cancer cells, largely irrespective of disease subtype or tissue of origin. Accordingly, when donor-derived human macrophages were co-cultured with a variety of solid tumor-derived cell lines, the humanized anti-CD47 antibody Hu5F9-G4 induces a significant increase in macrophage phagocytosis for the majority of cells (FIG. 1B, 12 of 18 lines, p<0.05), as assessed by a thoroughly validated flow cytometry-based phagocytosis assay (FIG. 6) (see Liu et al, PLoS One. 2015 Sep. 21; 10(9):e0137345, which is hereby incorporated by reference in its entirety, e.g., for its teachings related to anti-CD47 antibodies). However, some lines do not significantly respond to anti-CD47 therapy (6 of 18), and amongst responders, the magnitude of induced phagocytosis varies widely (FIG. 1B). These differences did not correlate with cancer subtype, nor did they correlate with surface CD47 levels, which were high in all cell lines tested (FIG. 7). Because Hu5F9-G4 simultaneously blocks CD47:SIRPA signaling and opsonizes cells, we speculated that Hu5F9-G4-resistant lines must express one or more "don't eat me" signals in addition to CD47.

In order to identify these signals, an antibody array system was used to characterize the surface immunophenotype of five cell lines: the colon cancer lines DLD1 and HCT116; the small cell lung cancer lines NCI-H82 and NCI-H196; and the pancreatic neuroendocrine tumor line KWNO1. These lines span a broad spectrum of tumor types, as well as a wide range of sensitivity to phagocytosis upon Hu5F9-G4 treatment (FIG. 1B). In analyzing the data from these arrays, an intriguing relationship between expression of MHC class I proteins and resistance to Hu5F9-G4-induced macrophage phagocytosis was noted (FIG. 8).

HLA alpha chains and the B2M protein assemble to form the MHC class I complex, which has essential roles in T cell and NK cell regulation, but no classically described function in the regulation of macrophages. Nonetheless, analysis of HLA expression across the panel of 18 cell lines revealed a highly significant correlation between surface levels of MHC class I and resistance to macrophage-mediated phagocytosis upon Hu5F9-G4 treatment (FIG. 1C, $R^2$=0.411, p=0.002).

MHC Class I Directly Protects Cells from Macrophage Attack

Figure 2A:
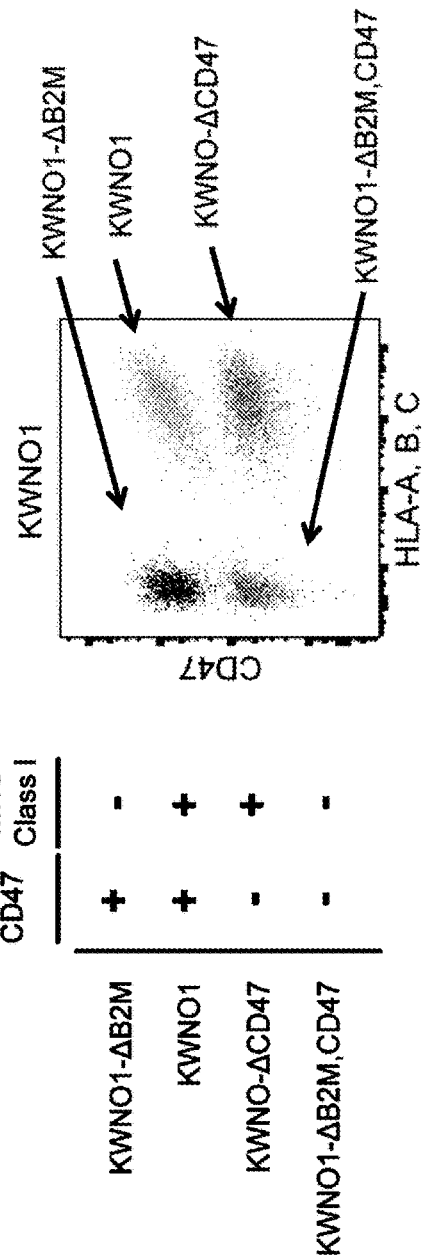
FIG. 2A-2G. MHC class I directly protects cells from macrophage attack.
Figure 2B:
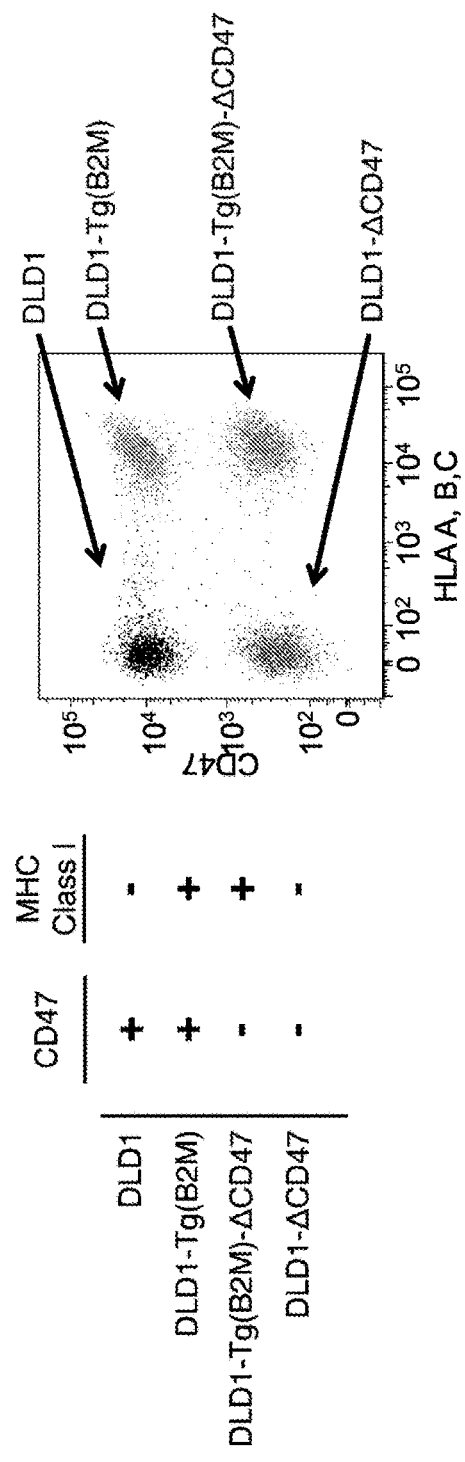

In order to investigate this correlation, a series of genetic experiments were performed utilizing the KWNO1 and DLD1 lines. Both lines were positive for expression of CD47 (FIG. 2A, FIG. 2B), but while KWNO1 expressed high levels of MHC class I, DLD1 was negative for surface MHC due to biallelic inactivation of the B2M locus. Through irreversible genetic modification and sequential rounds of fluorescence-activated cell sorting (FACS), polyclonal sub-lines of KWNO1 and DLD1 were generated with all four permutations of positive or negative expression of MHC and CD47 (FIG. 2A and FIG. 2B).

Figure 2C:
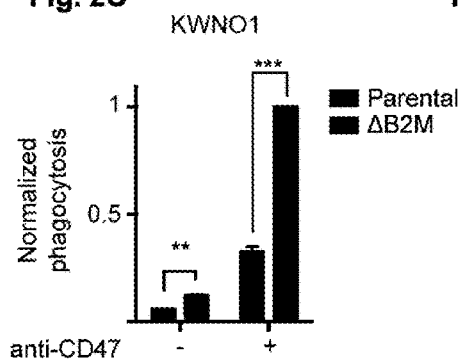
Figure 2E:
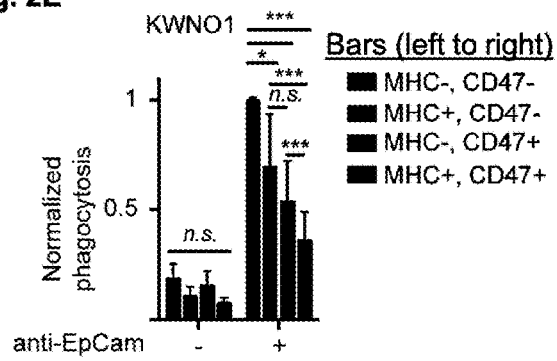

Co-culture of these lines with donor-derived human macrophages revealed that deletion of surface MHC was sufficient to modestly but significantly increase spontaneous phagocytosis in some cases (FIG. 2C, p<0.01). Furthermore, in a critical confirmation of the hypothesis, MHC− cells were significantly more sensitive to anti-CD47-induced phagocytosis than their MHC+ counterparts (FIG. 2C, d p<0.001). Analysis of the extended allelic panels of these lines confirmed that upon treatment with opsonizing antibody, cells lacking both CD47 and MHC expression were significantly more sensitive to phagocytosis than cells expressing MHC class I alone (FIG. 2E and FIG. 2F, blue versus green; p<0.05 and p<0.001, respectively) or cells expressing CD47 alone (FIG. 2E and FIG. 2F, blue versus black, p<0.001), and in the KWNO1 cell line, simultaneous expression of both MHC and CD47 was significantly more protective than either signal alone (FIG. 2E, red, p<0.001). Thus, MHC class I and CD47 are independent anti-phagocytic signals that can work cooperatively to protect cells from macrophage attack.

Figure 2D:
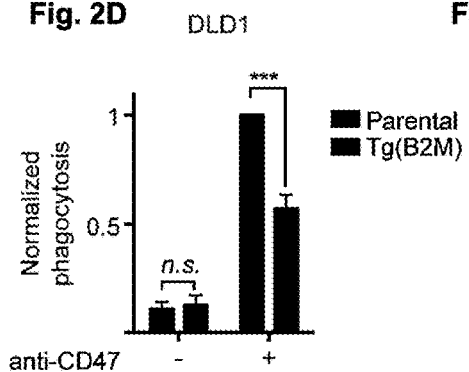
Figure 2F:
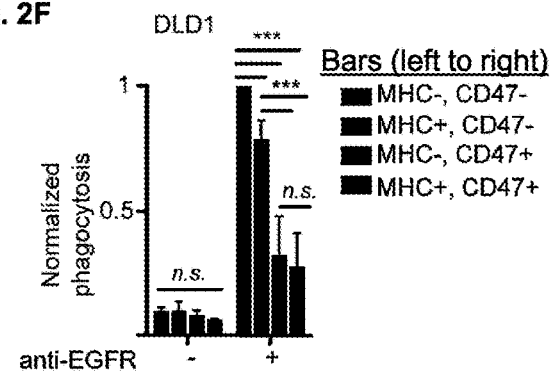
Figure 2G:
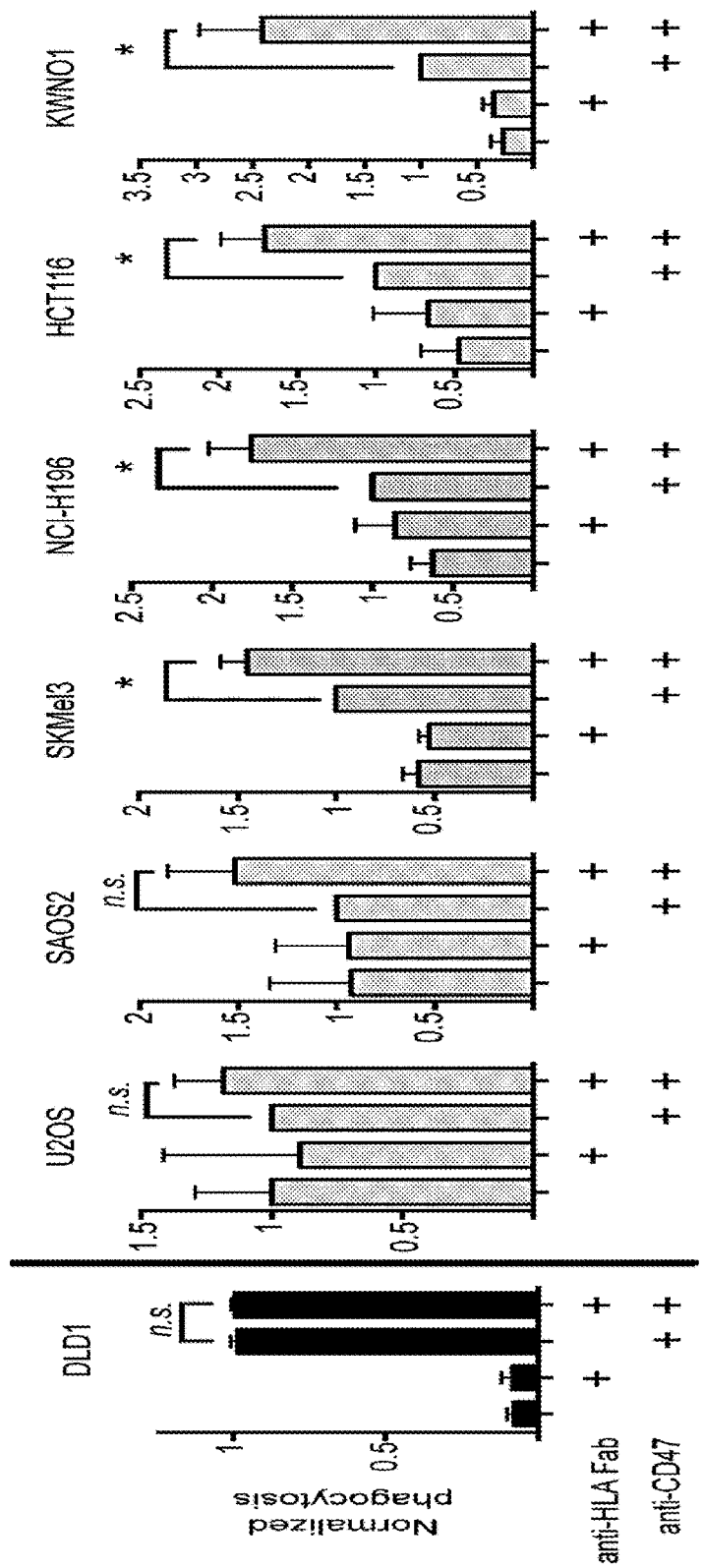

Based on this result, it was speculated that blockade of MHC signaling could be a general tool to sensitize cells to phagocytosis. A Fab fragment derived from the pan-HLA-A, B, C monoclonal antibody, W6/32, was therefore generated, allowing the examination of the MHC blocking effects of this antibody in isolation from any Fc-mediated effects. HLA-binding Fab did not influence the phagocytosis of a MHC-negative cell line, DLD1 (FIG. 2G, left panel). However, when applied to a panel of MHC high cells (FIG. 9), the HLA-binding Fab significantly increased anti-CD47-induced phagocytosis for 4 out of 6 lines tested (FIG. 2G), including KWNO1, thus independently confirming the results of the genetic experiments (FIG. 2C and FIG. 2D).

LILRB1 is the Primary Receptor for Inhibitory MHC Signaling to Macrophages

Figure 3A:
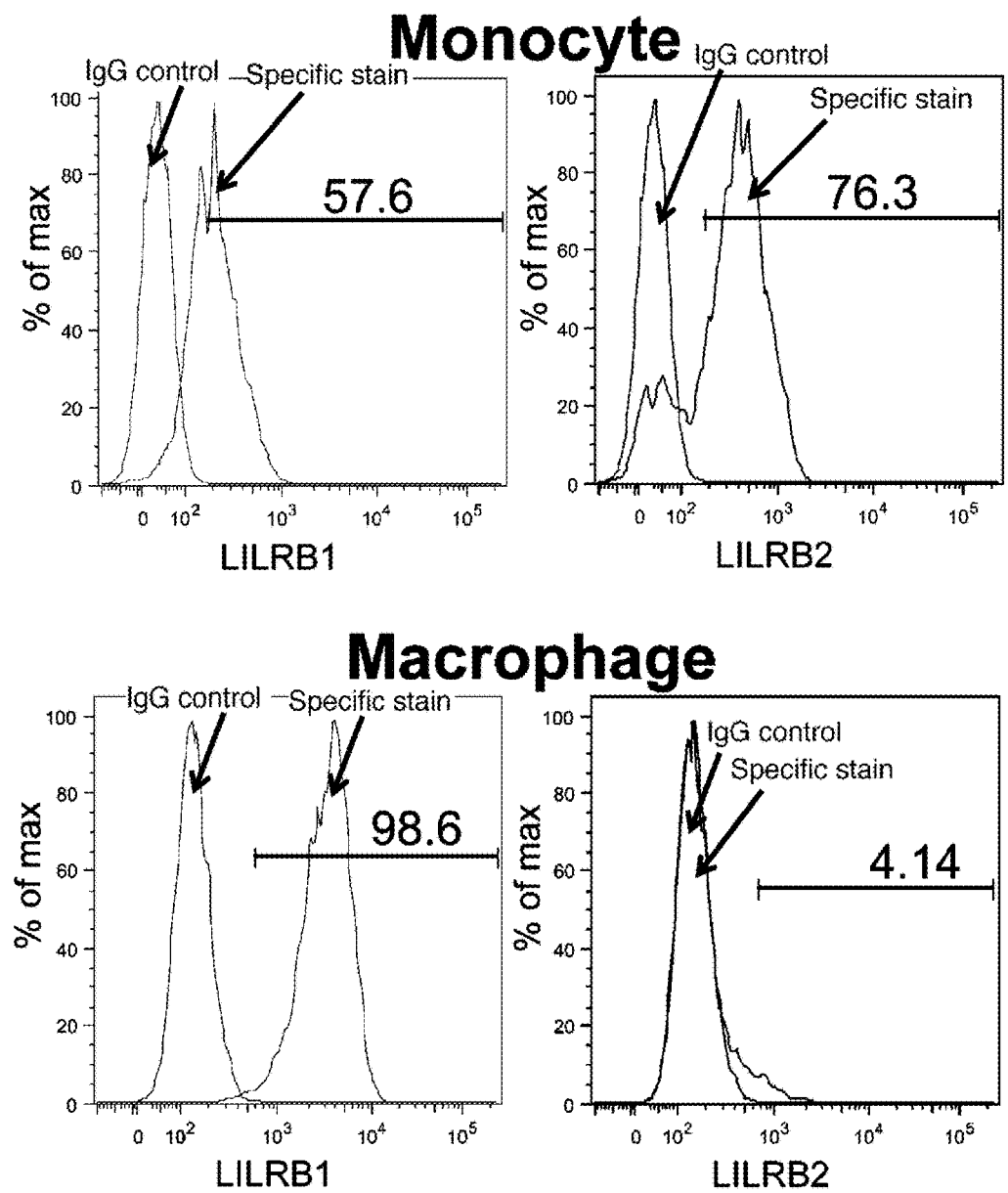
FIG. 3A-3C. The receptor LILRB1 mediates macrophage detection of MHC class I.
Figure 3B:
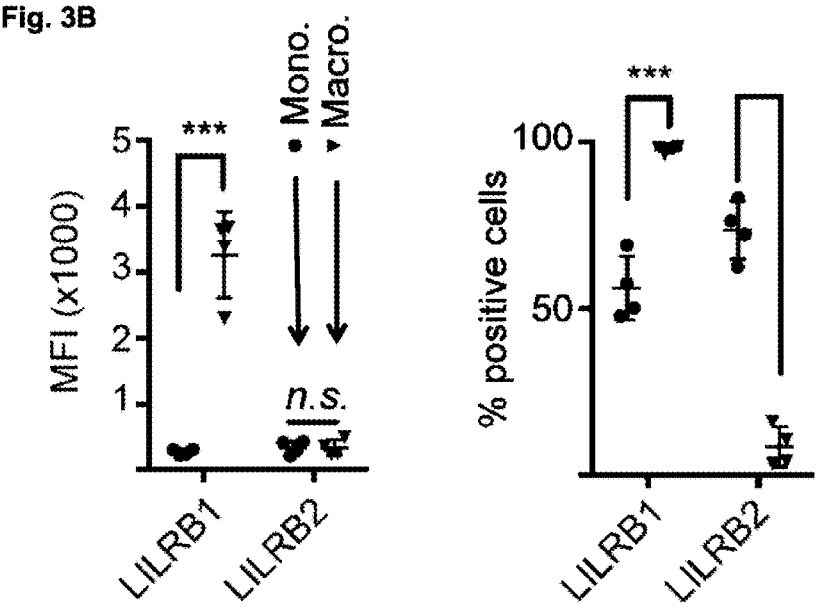

In order to further investigate the phenomenon of MHC-to-macrophage signaling, the next goal was to identify the receptor or receptors involved in its detection. FACS analysis of freshly isolated CD14+ human peripheral blood monocytes from four independent donors revealed that the majority of these cells express both LILRB1 and LILRB2 (FIG. 3A, FIG. 3B). However, after 7 days of ex vivo differentiation into mature macrophages, LILRB1 expression significantly increased (FIG. 3A, b p<0.001), while the percentage of cells expressing LILRB2 significantly diminished (FIG. 3A, b, p<0.001). This observation strongly implicated LILRB1—but largely excluded LILRB2—as a mediator of repressive MHC signaling in mature human macrophages.

Figure 3C:
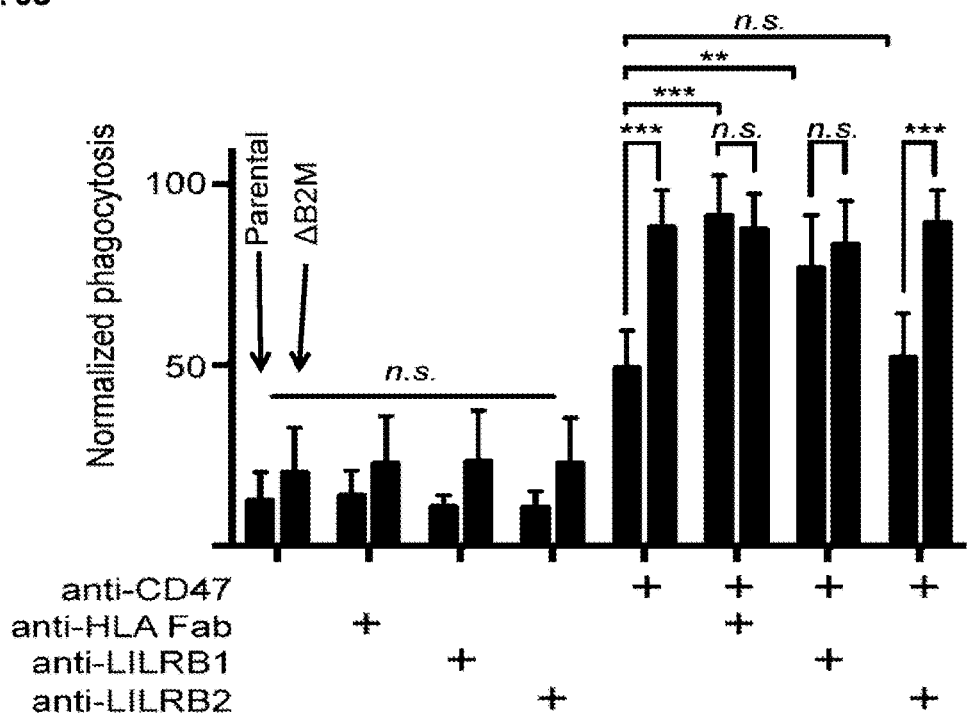

In order to functionally confirm this hypothesis, it was next tested whether blocking LILRB1 could increase phagocytosis of MHC+ cells. Indeed, GHI/75, a blocking monoclonal antibody against LILRB1, significantly increased the Hu5F9-G4-induced phagocytosis specifically of MHC+ cells (FIG. 3C, p<0.01), eliminating the differential between MHC+ and MHC− sub-lines for both KWNO1 (FIG. 3C) and DLD1 (FIG. 10). Conversely, treatment with a LILRB2 blocking antibody had no significant effect on phagocytosis for any cell population (FIG. 3B and FIG. 10). Taken together, these results strongly support LILRB1 as the primary effector of MHC detection during regulation of phagocytosis B2M Protein Confers Species-Specific MHC Detection by Macrophages All assays reported in this study utilized macrophages derived from multiple independent biological donors, with no prior analysis or selection based on HLA haplotype; despite this, a highly consistent protection by MHC expression was observed, suggesting a different paradigm of detection than the allele-specific mechanisms employed by T cells and NK cells. Consistent with this result, analysis of the previously solved crystal structure of LILRB1 bound to the human MHC class I complex revealed that the majority of contact residues between LILRB1 and MHC are within the invariant B2M subunit rather than the highly polymorphic HLA alpha chain (FIG. 4A).

There are substantial differences in LILRB-family genes between humans and mice, but previous work suggests that the mouse receptor PirB may subsume most of the functions described for both human LILRB1 and LILRB2, including repressive signaling upon MHC binding. Accordingly, PirB was found to be highly expressed on the surface of in vitro-differentiated mouse macrophages (FIG. 11). However, in contrast to human macrophages, mouse macrophages did not strongly discriminate between human MHC+ and MHC− cells.

Figure 4A:
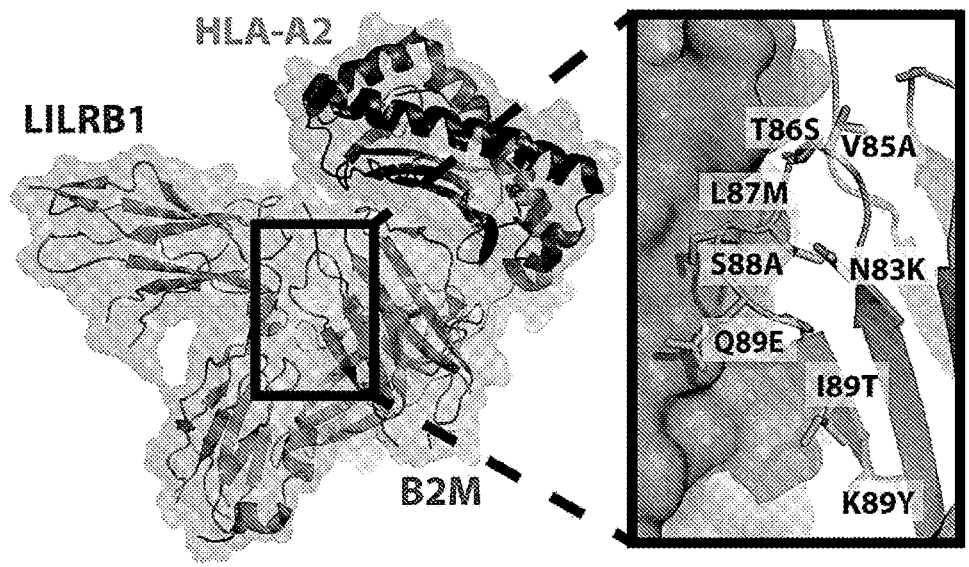
FIG. 4A-4C. B2M confers species-specific protection against macrophage phagocytosis.

Alignment of the human and mouse B2M protein sequences revealed an identity mismatch of approximately 30%, including several amino acids in the region of predicted contact between human B2M and LILRB1 (FIG. 4A). Differences in these residues might account for the lack of signaling from human MHC to mouse macrophages, and it was next sought to determine whether mouse B2m and human B2M could endow cells with a species-specific protection against phagocytosis.

Figure 4B:
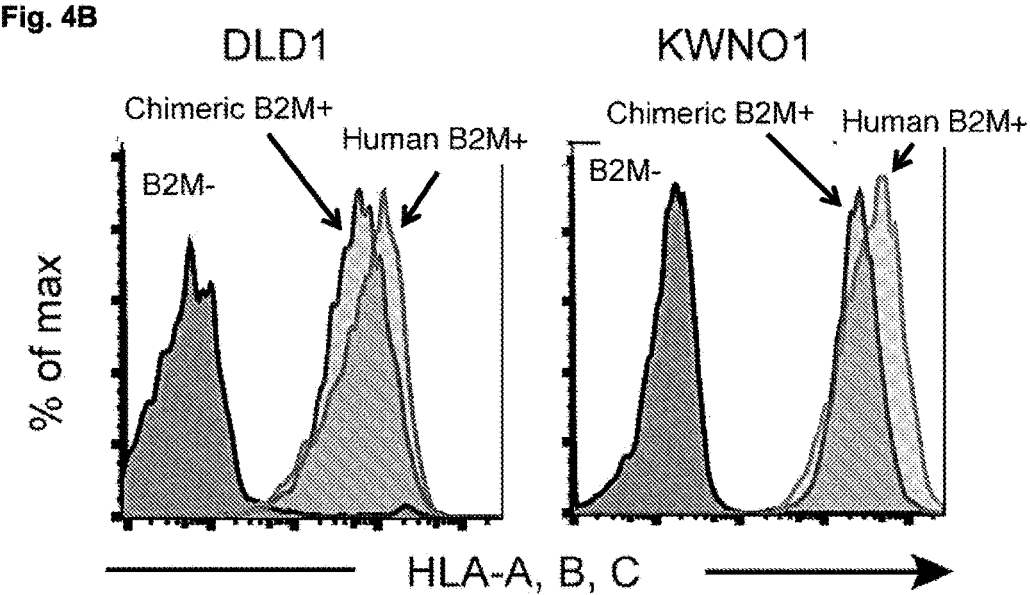

An attempt to express mouse B2m in human cells revealed that this foreign protein was unable to form stable surface MHC complexes with human HLA alpha chains (FIG. 12). To circumvent this technical limitation, a human-mouse chimeric B2M (hmcB2M) was generated in which the human protein was mutated to include amino acids of mouse sequence within the predicted region of interaction with LILRB1 (FIG. 4A, inset region). Expression of hmcB2M in either B2M-negative parental DLD1 cells, or in B2M-deleted KWNO1, enabled robust surface expression of HLA comparable to that achieved with fully human B2M protein (FIG. 4B, purple versus red).

Figure 4C:
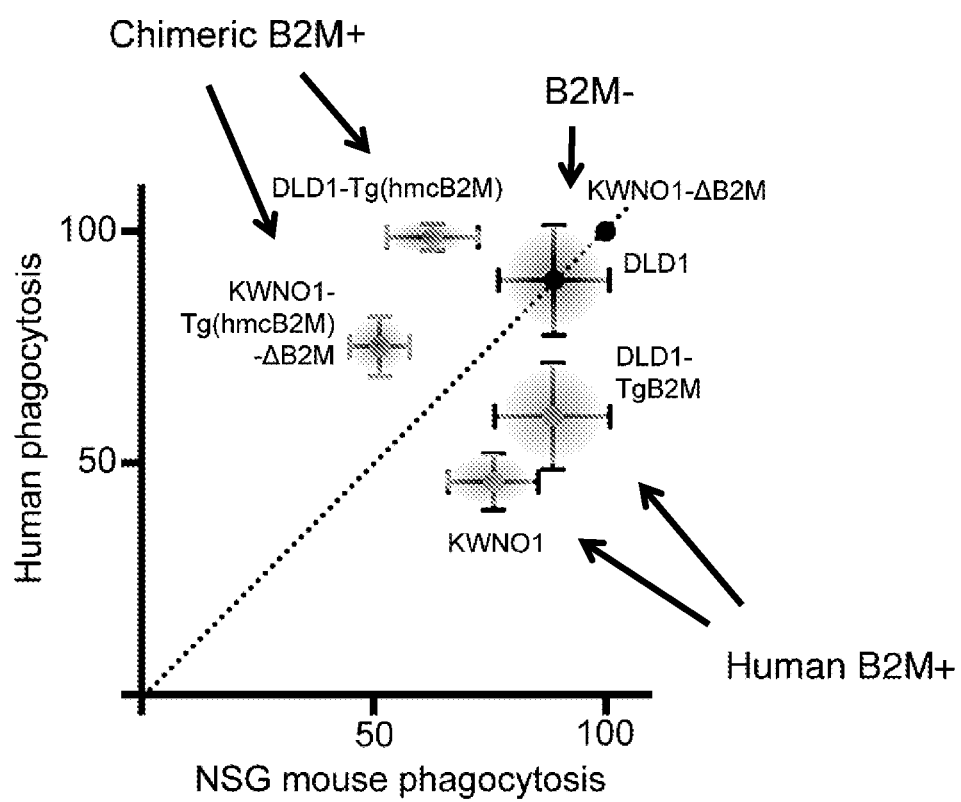
Figure 5A:
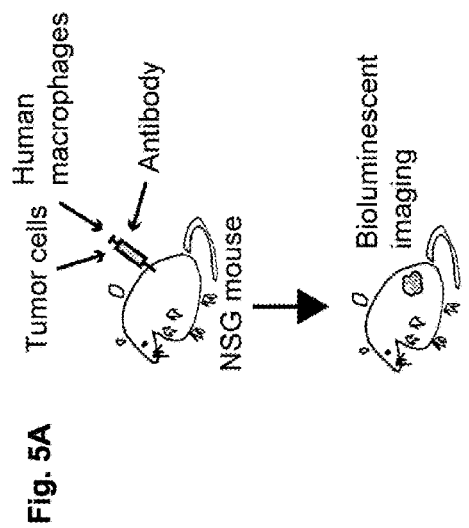
FIG. 5A-5E. MHC class I expression protects tumor cells from macrophages in vivo.

Using these lines, it was confirmed that although human B2M strongly protected target cells against human macrophages (FIG. 4C, y axis, black versus red), it was inefficient in protecting against murine macrophages (FIG. 4C, x axis, black versus red); in contrast, expression of hmcB2M conferred precisely the inverse protection (FIG. 4C, black versus purple). This result genetically demonstrates that the amino acid residues in the LILRB-interacting region of B2M are critical for species-specific detection of MHC by both human and mouse macrophages MHC Protects Cancer Cells from Macrophage Attack In Vivo The next goal was to study the in vivo consequences of MHC-to-macrophage signaling, and in particular to determine whether MHC expression by cancer cells protects them from macrophage immune surveillance in vivo. Based on the species-specific nature of this interaction (FIG. 4C), it was a goal first to establish a xenograft system by which we could assess the interaction of human macrophages with human cancer cells in vivo. NSG (NOD-SCID Il2r$\gamma^{-/-}$) mice produce functional cells of the myeloid lineage, but lack T, B and NK cells, and therefore can accept cross-species transplants. These mice were used as hosts into which ex vivo human macrophages were co-engrafted alongside KWNO1 human cancer cells (schematic in FIG. 5A).

Figure 5B:
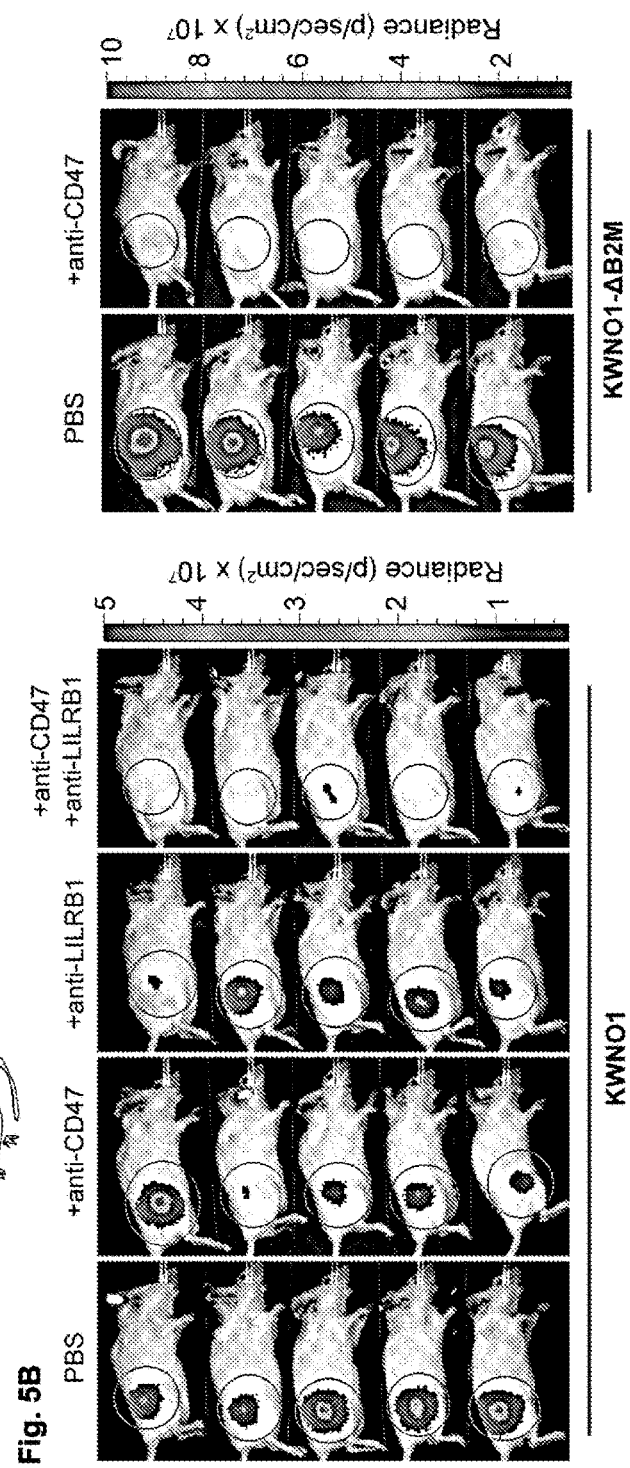

MHC+ KWNO1 cells readily engrafted into NSG hosts, despite the presence of human macrophages (FIG. 5B, left panel), and consistent with the in vitro assays, were only modestly affected by treatment with the blocking anti-CD47 antibody Hu5F9-G4 (FIG. 5B, left panel). In contrast, treatment of the MHC− KWNO1 sub-line with Hu5F9-G4 resulted in complete clearance of tumor cells, with no bioluminescence detectable at 14 days post-injection (FIG. 5B, right panel), a striking demonstration of the potency of MHC-mediated macrophage regulation. In a symmetric demonstration of this principle, combination treatment with anti-CD47 and anti-LILRB1 blocking antibody was sufficient to dramatically reduce tumor formation by MHC+ KWNO1 cells (FIG. 5B, left panel), leading to >80-fold reduction in overall tumor burden by day 7 as compared to PBS treated mice, and a ~50-fold reduction as compared to tumors treated with Hu5F9-G4 alone (FIG. 5B and FIG. 13).

Figure 5C:
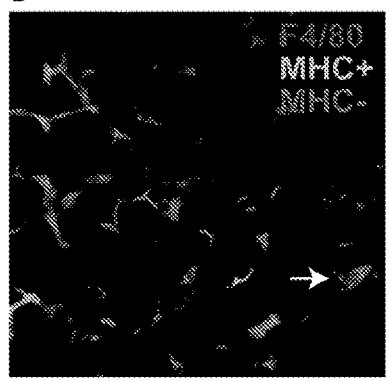

Phagocytosis in this xenograft system had tapered by day 7, consistent with the dispersal of the co-engrafted human macrophages or of the human-specific antibody treatments after initial injection (FIG. 13). Therefore, in order to study the long-term effects of tumor-to-macrophage MHC signaling in vivo, sub-lines of KWNO1 expressing the human-mouse chimeric B2M were used (FIG. 4). An initial histological analysis of tumors derived from a mixed population of MHC− cells and chimeric MHC+ cells revealed substantial infiltration by mouse macrophages (FIG. 5C, blue), as well as clear instances of tumor cell phagocytosis (FIG. 5C, white arrowhead), thereby demonstrating that NSG macrophages are indeed present in the tumor and capable of mounting an anti-tumor response against these cells in vivo.

Figure 5D:
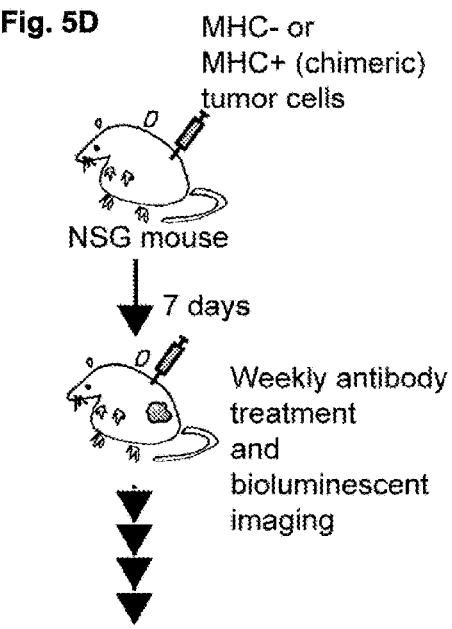
Figure 5E:
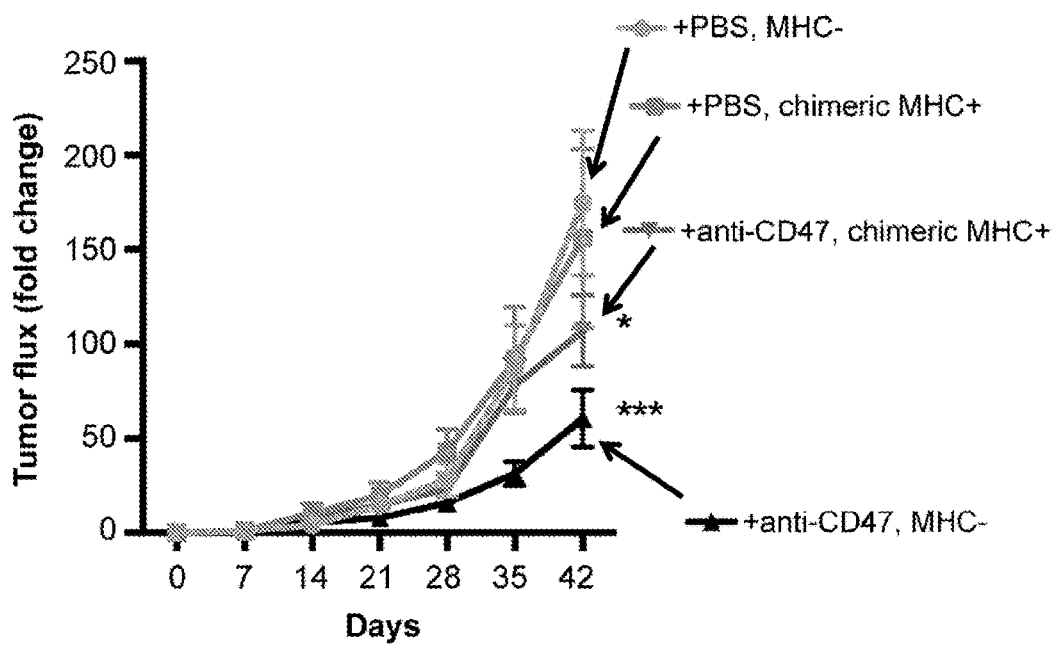

In order to quantitatively compare the in vivo sensitivity of MHC− versus chimeric MHC+ cells to anti-CD47 agents, MHC− KWNO1 cells or chimeric MHC+ KWNO1 cells were grafted into the flanks of NSG mice, and bioluminescent imaging was used to follow tumor growth under conditions of PBS treatment or once-weekly Hu5F9-G4 administration (schematic in FIG. 5D). At early time points, there was no significant difference in luminescence between the tumors of any treatment group, or between chimeric MHC+ and MHC− tumors (FIG. 5E). By day 42, once-weekly anti-CD47 treatment had significantly slowed the growth of both MHC− and chimeric MHC+ tumors (FIG. 5E, p<1e-4 and p<0.05, respectively). However, there was significantly less therapeutic benefit to anti-CD47 for MHC+ KWNO1 tumors, which grew at a significantly faster rate than MHC− tumors (FIG. 5E, p<0.05; see FIG. 16 for a comprehensive statistical comparison between all time points and groups). Given that these cancer sub-lines differ only in their B2M expression status, which had no measurable effect on their in vitro growth rate (FIG. 14 and FIG. 15), these results demonstrate a MHC-mediated effect on macrophage immune surveillance of tumor cells in vivo Discussion The data presented here demonstrate that MHC class I is a key regulatory signal for the effector functions of macrophages, thus expanding our understanding of one of immunology's best-studied and most important signaling complexes, and highlighting the central role of MHC in coordinating the activity of both the adaptive and innate branches of the immune system. MHC:LILRB1 signaling has been previously studied in a subset of NK cells, and in the myeloid lineage for its role in monocyte activation. However, as described here, while freshly isolated monocytes have detectable expression of LILRB1, surface levels of this gene increase approximately 10-fold during differentiation into mature macrophages (FIG. 3B). This increase, when taken together with the functional data described here, suggests that regulation of macrophage phagocytosis is a key role of LILRB1 signaling.

The results herein have important implications for several aspects of macrophage biology. Viruses can avoid presentation of foreign peptides to T cells by down-regulation of surface MHC class I, which can consequently activate NK cell attack due to lack of MHC binding by killer cell immunoglobulin-like receptors (KIRs). It is likely that the MHC:LILRB1 signaling axis serves an analogous role for macrophage-mediated immune surveillance of infected cells. Furthermore, the human cytomegalovirus (CMV) family has evolved to encode a protein, UL-18, which mimics HLA but prevents binding by T cells. It binds LILRB1 with >1000-fold higher affinity as compared to native MHC complexes, and according to previous reports, inhibits the subset of NK cells that express LILRB1. Given the high LILRB1 expression in mature macrophages, UL-18 is likely to modulate macrophage-mediated phagocytosis of CMV-infected cells, and this may therefore influence the pathology of CMV infection.

MHC:LILRB1 signaling is also important in the dynamics of programmed cell removal. As erythrocytes age, their effective CD47 signaling gradually decreases, eventually dropping below a critical threshold and thus enabling phagocytosis by macrophages. While the majority of normal human tissues express MHC class I, including erythrocyte precursors, mature erythrocytes lack surface MHC. In light of the results herein, this lack of expression may be a factor in priming erythrocytes for eventual phagocytosis, and may serve to in part explain the anemia induced by anti-CD47 antibodies or CD47-binding Fc-fusion proteins when deployed as cancer therapies.

As demonstrated by the results herein, both in vitro and in vivo, lack of MHC expression endows cancer cells with sensitivity to phagocytosis. Many cancers present clinically with compromised or negative expression of surface MHC. Due to impaired presentation of mutated cancer neo-antigens, these patients are very poor candidates for T cell focused therapies, but the results presented here suggest that they are ideal candidates for macrophage-mediated immunotherapies. Thus, MHC expression status may be used as predictive biomarker not only for the efficacy of T cell therapies such as anti-PD-1 or PD-L1 agents, but also for the efficacy of anti-CD47 or anti-SIRPA drugs in a variety of disease indications.

Beyond its use a biomarker, the work here suggests that in patients with tumors expressing normal or high levels of MHC, therapeutic agents that disrupt the MHC:LILRB1 interaction may independently increase the efficacy of tumor-binding monoclonal antibodies, and will cooperate with agents against CD47:SIRPA.

Agents against the MHC:LILRB1 signaling axis can be an important component of any therapeutic regimen that aims to engage macrophages in the fight against cancer Experimental Procedures Cell Culture DLD-1, NCI-H69, NCI-H82, NCI-H1688, NCI-H196, NCI-H524, Bon, and KWNO1 cells were grown in RPMI+GlutaMax (Life Technologies) supplemented with 10% fetal bovine serum (Hyclone), and 100 U/mL penicillin and streptomycin (Life Technologies). NCI-H128 was grown in RPMI+GlutaMax (Life Technologies) supplemented with 20% fetal bovine serum (Hyclone), and 100 U/mL penicillin and streptomycin (Life Technologies). HT-29, SkBr3, and SkMel3 were grown in McCoy's 5A+GlutaMax (Life Technologies) supplemented with 10% fetal bovine serum (Hyclone), and 100 U/mL penicillin and streptomycin (Life Technologies). LS-174T, MCF7, and SkMel28 were grown in Eagle's Minimum Essential Media (ATCC) supplemented with GlutaMax (Life Technologies), 10% fetal bovine serum (Hyclone), and 100 U/mL penicillin and streptomycin (Life Technologies). When necessary, cells were detached from plates and disaggregated using TrypLE Express (Life Technologies) according to the manufacturer's indications. All cell lines were obtained from ATCC with the exception of KWNO1, which was a generous gift from Geoff Krampitz at Stanford University. Unless otherwise indicated, cell lines were propagated and subcultured according to ATCC guidelines.

Generation of Lentiviral Particles

HIV-based replication incompetent lentiviral particles were generated in 293 Lenti-X cells (Clontech) by co-transfection of pMDG.2 vector (Addgene), psPAX2 (Addgene), and a third vector specific to the lentiviral application, using the Xtremegene HD transfection reagent (Roche) according to the manufacturer's protocol. Vectors were transfected at a mass ratio of 4:2:1, lenti-specific vector: psPAX2: pMDG.2. After transfection, cell culture media supernatant was collected at 36 hours and 60 hours. Lentiviral particles were concentrated either by ultracentrifugation for 2.5 hours at 50,000 g, or with PEG-it (Systems Biosciences) according to the manufacturer's indications. Proper biosafety and disposal techniques were followed whenever using lentiviral reagents, according to Stanford University guidelines.

Generation of DLD1 and KWNO1 Sub-Lines

In order to generate sub-lines of DLD1 and KWNO1, parental, unmodified cells were harvested in single-cell suspension and mixed with pre-warmed growth media, concentrated lentivirus, and 10 µg/mL polybrene (Sigma). Cells were then centrifuged at 1800 rpm, room temperature for 45 minutes. Lentiviral pools included at least three distinct viral species: one encoding for the Cas9 nuclease, and two others encoding for different CRISPR small guide RNAs (sgRNAs) targeting the first exon of either CD47 or B2M, as appropriate. CRISPR sgRNAs were designed using the tools at genome-engineering.org, and were of the following sequences: sgCD47-1: GCTACTGAAGTATACG-TAAAG (SEQ ID NO: 18), sgCD47-2: GCTTGTTTA-GAGCTCCATCAA (SEQ ID NO: 19), sgB2M-1: GAGTAGCGCGAGCACAGCTA (SEQ ID NO: 20), sgB2M-2: GGCCGAGATGTCTCGCTCCG (SEQ ID NO: 21). 7 days post infection, cells were assessed for expression status by flow cytometry. CD47 was assessed by staining with APC-conjugated B6H12 (Biolegend) and HLA-A, B, C was assessed by staining with PE-Cy7-conjugated W6/32 (Biolegend). Cells were sorted on a FACSAria II cell sorter (BD Biosciences). Typically, each cell line was sorted three times, separated by several days of recovery and expansion between rounds. Wild-type human B2M (NC_000015.10), wild-type mouse B2m (NC_000068.7), or chimeric human-mouse B2M (hmcB2M; see below for sequence) were cloned into the NheI and NotI sites of the pCDH-CMV-MCS-EF1-Puro vector (Systems Biosciences), and these vectors were used to produce lentivirus and introduce transgenes, as appropriate. DLD1-Δ(CD47) was generated by transient co-transfection of CD47-targeting TALEN vectors, described below, using Xtremegene HD (Roche) according to the manufacturer's indicated protocol. All other genetic modifications were induced using lentiviral delivery of transgenes, or lentiviral delivery of Cas9 and corresponding sgRNAs, as described above.

TALEN Design and Construction

TALENs were designed and assembled as described. The genomic locus of human CD47 (NC_000003.12) was scanned for putative TALEN binding pairs. Exon 2 was ultimately selected for targeting and the TALEN pairs TGTCGTCATTCCATGCTTTG (SEQ ID NO: 22) and TATACTTCAGTAGTGTTTTG (SEQ ID NO: 23) were respectively cloned into the pTALEN backbone.

GFP-Luciferase Transduction

In order to facilitate both the FACS-based phagocytosis assay and in vivo imaging, we generated sublines of DLD1, HT-29, LS-174T, SkBr3, Bon, KWNO1, SkMel28, and SkMel3 engineered to stably express a GFP-luciferase fusion protein (Systems Biosciences, catalog number BLIV100PA/VA-1). U2OS and SAOS2 were engineered to stably express an RFP-luciferase fusion protein (Systems Biosciences, catalog number BLIV101PA/VA-1). Parental, unmodified cells were harvested in single-cell suspension and mixed with pre-warmed growth media, concentrated lentivirus, and 10 µg/mL polybrene (Sigma). Cells were then centrifuged at 1800 rpm, room temperature for 45 minutes. Uniform GFP+ or RFP+ populations were then generated by sequential rounds of cell sorting on a FACSAria II cell sorter (BD Biosciences).

Macrophage Generation

Leukocyte reduction system (LRS) chambers from anonymous donors were obtained from the Stanford Blood Center. Monocytes were purified from these samples on an autoMACS Pro Separator (Miltenyi) using anti-CD14 microbeads optimized for whole blood separation (Miltenyi) according to the manufacturer's suggested protocol. Monocytes were then differentiated to macrophages by 7-10 days of culture in IMDM+GlutaMax (Life Technologies) supplemented with 10% AB Human Serum (Life Technologies) and 100 U/mL penicillin and streptomycin (Life Technologies). NSG macrophages were generated as previously described. Briefly, bone marrow cells were harvested from the lower limbs of 6-8 week old NSG mice, and cultured for 7 days in IMDM+GlutaMax[13] (Life Technologies) supplemented with 10% fetal bovine serum (Hyclone), 100 U/mL penicillin and streptomycin, and 10 ng/mL murine M-CSF (Peprotech).

FACS-Based Phagocytosis Assay

Each phagocytosis reaction reported in this work was performed by co-culture of 100,000 target cells and 50,000 macrophages for two hours in ultra-low attachment 96 well U-bottom plates (Corning) in IMDM+GlutaMax (Life Technologies) without antibiotics or serum added. Macrophages were generated as described above, and harvested from plates using TrypLE Express (Life Technologies). Target cells were either engineered to stably express GFP or RFP fluorescent protein, as described above, or stained with Calcein AM (Life Technologies) according to the manufacturer's indications prior to co-culture. Treatment antibodies, including anti-CD47 clone Hu5F9-G4, cetuximab (Bristoll-Myers Squibb), anti-LILRB1 clone GHI/75 (BioLegend), and anti-LILRB2 clone 27D2 (Biolegend) were added to reactions at a concentration of 10 µg/mL. After co-culture, reactions were stained were stained with APC-labeled anti-CD45 clone H130 (BioLegend) to identify human macrophages, and with PE-Cy7-labeled anti-F4/80 clone BM8 (BioLegend) to identify NSG mouse macrophages. DAPI staining was used to exclude dead cells from the analysis (Sigma). Reactions were run on an LSRFortessa Analyzer outfitted with a high-throughput auto-sampler (BD Biosciences). Phagocytosis was evaluated as a sum of the GFP+ macrophages (both "Mid" and "High" gates were included in this number, as described in FIG. 6), expressed as a percentage of the total macrophages, as analyzed using FlowJo v.9.4.10 (Tree Star) and was normalized as indicated in the figure legends. Unless otherwise stated, each replicate represents a true biological replicate (i.e. an independent human macrophage donor), and unless otherwise indicated, replicates were split between a minimum of two independent experimental instances (e.g. four independent donors evaluated on day 1, with an additional four independent donors evaluated on day 2). Sample size was chosen to ensure a greater than 95% probability of identifying, by two-tailed t-test, an effect of >20%, assuming a technical variation of 15%.

Antibody Array

We used the LegendScreen antibody array system (BioLegend) to assess the surface phenotype of the NCI-H69, NCI-H82, NCI-H524, and NCI-H196 cell lines. The cells were harvested and disaggregated with TrypLE (Life Technologies), and NCI-H82 and NCI-H69 were stained using Calcein AM (Life Technologies) according to the manufacturer's protocol. NCI-H82 (calcein-stained) and NCI-H524 (unstained) cells were run together in a multiplexed fashion, as were NCI-H69 (calcein-stained) and NCI-H196 (unstained). Cells were distributed amongst antibody-containing wells, stained, and washed according to the manufacturer's indications. Samples were subsequently run on an LSRFortessa Analyzer outfitted with a high-throughput auto-sampler (BD Biosciences). Fluorescence levels were evaluated using FlowJo v.9.4.10 (Tree Star). Calcein staining signal was used to deconvolute multiplexed samples.

Antibody Staining

FACS analysis was performed either on a FACSAria II cell sorter (BD Biosciences) or on an LSRFortessa Analyzer (BD Biosciences). Surface CD47 levels were assessed by antibody staining with clone B6H12 (BioLegend) at a dilution of 1:100. HLA-A/B/C was assessed by antibody staining with clone W6/32 (BioLegend) at a dilution of 1:50. LILRB1 was assessed by antibody staining with clone GHI/75 (BioLegend) at a dilution of 1:25. LILRB2 was assessed by antibody staining with clone 27D2 (BioLegend) at a dilution of 1:25. All stains were performed on ice for 30 minutes, then washed and resuspended according to standard practice.

Human-Mouse Chimeric B2M

Chimeric B2M was designed to incorporate C-terminal amino acid differences from mouse B2m into a primarily human B2M sequence. The sequence (indicated below) was chemically synthesized (IDT), and cloned into the NheI and NotI sites of pCDH-CMV-MCS-EF1-Puro. Sequence of mouse origin is in lower case.

```
>hmcB2M_geneblock
                                        (SEQ ID NO: 24)
TTTAAGCTAGCATGTCTCGCTCCGTGGCCTTAGCTGTGCTCGCGCTACT

CTCTCTTTCTGGCCTGGAGGCTATCCAGCGTACTCCAAAGATTCAGGTT

TACTCACGTCATCCAGCAGAGAATGGAAAGTCAAATTTCCTGAATTGCT

ATGTGTCTGGGTTTCATCCATCCGACATTGAAGTTGACTTACTGAAGAA

TGGAGAGAGAATTGAAAAAGTGGAGCATTCAGACTTGTCTTTCAGCAAG

GACTGGTCTTTCTATCTCTTGTACTACACTGAATTCACCCCCACTGAAA

AAGATGAGTATGCCtgcagagttaagcatgccagtatggccgagcccaa gaccgtctactgggatcgagacatgtgaGCGGCCGCAATTT.
```

Generation of W6/32 Fab Fragments

W6/32 antibody (BioXcell) was desalted into a solution of 20 mM sodium citrate pH 6.0, 25 mM cysteine, 5 mM EDTA, and diluted to a concentration of 4 mg/mL. Protease digestion was achieved by mixing with 250 µL immobilized ficin resin (Thermo Scientific) per mL of antibody. The mixture was incubated with rotation at 37° C. for 5 hours. After incubation, Fab fragments were purified from undigested antibody and Fc fragments by ion-exchange chromatography with a monoQ column, followed by size exclusion chromatography with a Superdex-200 column. Fab fragments were quantified by Nanodrop, and checked for purity by coomassie stain.

Crystal Structure Images

Crystal structure images were generated with MacPyMol v. 1.7.0.3 from the published structure IP7Q.

Mice

Nod.Cg-Prkdc$^{scid}$ IL2rg$^{tm1\,Wjl}$/SzJ (NSG) mice were used for all in vivo experiments. Mice were engrafted with tumors at approximately 6-10 weeks of age, and experiments were performed with age and sex-matched cohorts. Mice were maintained in a barrier facility under the care of the Stanford Veterinary Services Center and handled according to protocols approved by the Stanford University Administrative Panel on Laboratory Animal Care.

Humanized NSG Mouse Model

Ex vivo cultured human macrophages and GFP-luciferase labeled KWNO1 or KWNO1-Δ(B2M) cells and were generated and harvested as described above. 200,000 human macrophages, 100,000 target cells, and 1 μL of PBS, 1 μL of Hu5F9-G4 1 mg/mL stock, or 1 μL GHI/75 1 mg/ml stock was resuspended in 50 μL of RPMI and injected subcutaneously into the right flank of an NSG mouse. 5 mice were used for each treatment group. Tumor bioluminescence was assessed using an IVIS Spectrum imager (Perkin Elmer) at 12 hours post-injection, 4 days post-injection, 7 days post-injection and 14 days post-injection, as indicated. Experiments were performed in a non-blinded fashion.

In Vivo Growth Experiments

NSG mice were injected subcutaneously in the right flank with either 100,000 GFP-luciferase-labeled KWNO1-Δ(B2M) (30 mice) or KWNO1-Tg(hmcB2M)-Δ(B2M) cells (30 mice) and randomized into treatment cohorts using the list randomization tools at random.org. Sample size was chosen to ensure a greater than 95% probability of identifying, by two-tailed t-test, an effect of >50%, assuming a technical variation of 50%. Starting on day 14, mice were treated once per week by intraperitoneal injection of either 100 μL of PBS or 250 μg Hu5F9-G4 at a concentration of 2.5 mg/mL. Tumor luminescence was measured once per week using an IVIS Spectrum imager (Perkin Elmer). Measurements were discontinued when tumors in a measurement group began to exceed $5 \times 10^{10}$ total flux, which is, in our experience, a threshold above which bioluminescent signals are less accurate. Across additional experiments, including pilot experiments, additional mice were engrafted subcutaneously with these cell lines and treated with PBS, but were not included as part of this data set. One additional cage of 4 mice was engrafted with each KWNO1-Δ(B2M) and KWNO1-Tg(hmcB2M)-Δ(B2M) and received once-weekly Hu5F9-G4 treatment, but were ultimately not included in the final analysis of the experiment. Mouse experiments were performed in a non-blinded fashion.

Histology

KWNO1 tumors were fixed in 2% paraformaldehyde overnight at four degrees. Tissue was embedded and frozen in optimal cutting temperature compound O.C.T (Sakura) or embedded in paraffin. Frozen sections were cut at 4-7 μm and saved for immunofluorescence.

Immunofluorescence

Immunofluorescence studies were performed on frozen sections. Frozen sections were thawed at room temperature for ten minutes and washed in PBS twice. Slides were blocked in 5% serum for 30 minutes at room temperature. Sections were subsequently stained with primary antibodies against F4:80 (1:100, rat monoclonal, Abcam) overnight at 4 C, and washed three times in PBS. Slides were stained were incubated with secondary antibodies conjugated to AlexaFluor 647 for one to two hours at room temperature. Stains were washed once with PBST and three times with PBS before nuclear staining with Hoechst 33342 (Life Technologies), for two minutes and mounted with Fluoromount G (Southern Biotech). Basic photo processing, including fluorescence channel false-coloring, channel merge, and brightness and contrast adjustment, were performed using Adobe Photoshop (Adobe).

Example 3

FIG. 17. Results from experiments that measure phagocytosis of two different human breast cancer cell lines (MDA-MB-468 and MDA-MB-231) by human macrophages with and without anti-LILRB1 antibody (and in the presence or absence of other antibodies, e.g., Hu5F9-G4 which is an anti-CD47 antibody). Bars from left to right are: IgG4, Hu5F9-G4, Cetuximab, Trastuzumab, Panitumumab, Cetuximab+Hu5F9-G4, Trastuzumab+Hu5F9-G4, and Panitumumab+Hu5F9-G4.

FIG. 18 presents data showing that CD47 and MHC class I signaling axes are independent anti-phagocytic signals. FACS-based measurement of phagocytosis by human macrophages co-cultured with parental KWNO1 cells (gray) and B2M-deleted KWNO1 cells (pink), upon treatment with PBS, the anti-CD47 antibody Hu5F9-G4 (which blocks the CD47/SIRPA interaction), or the anti-CD47 antibody 2D3 (which binds CD47 but does not block its interaction with SIRPA, and thus represents any antibody that binds to a target cell and opsonizes that cell). Values are normalized to the max phagocytosis observed for a given set of replications. Deletion of B2M and consequent elimination of surface expression of MHC class I significantly increases the phagocytosis of KWNO1 cells relative to parental KWNO1 cells upon opsonization with the non-blocking anti-CD47 antibody 2D3 ($p<1\times10^{-4}$, ANOVA), thus demonstrating that disruption of MHC classI/LILRB1 increases phagocytosis even under conditions of intact CD47/SIRPA signaling. Co-disruption of MHC class I/LILRB1 signaling and CD47/SIRPA signaling by treatment of B2M-deleted KWNO1 cells with Hu5F9-G4, which blocks CD47/SIRPA and opsonizes target cells, leads to a significant and synergistic increase in phagocytosis relative to disruption of either signaling pathway alone (*$p<1\times10^{-4}$, ANOVA).

The data presented here demonstrate that MHC class I is a critical regulatory signal for the effector functions of macrophages. These findings identify the MHC/LILRB1 signaling axis as a target for treatment (e.g., cancer immunotherapy). By disrupting this pathway, e.g., in conjunction with tumor-specific monoclonal antibodies and agents (e.g., against the CD47/LILRB1 axis), therapeutic agents against MHC/LILRB1 may enable stimulation of potent macrophage-mediated anti-cancer (and/or anti-chronic infection) responses.

What is claimed is:

1. A composition for increasing phagocytosis of a target cell, the composition comprising:
   (a) an antibody that specifically binds to leukocyte immunoglobulin-like receptor subfamily B member 1 (LILRB1) and does not activate signaling through LILRB1 upon binding; and (b) an agent an antibody that binds to the target cell and thereby opsonizes the target cell.

2. The composition of claim 1, wherein the composition further comprises an anti-CD47/signal regulatory protein alpha (SIRPA) agent.

3. The composition according to claim 1, wherein the antibody that binds to the target cell binds to CD20.

4. The composition according to claim 3, wherein the antibody is rituximab.

5. The composition according to claim 1, wherein the antibody that binds to the target cell binds to EGFR.

6. The composition according to claim 5, wherein the antibody is cetuximab.

7. A method of inducing phagocytosis of a target cell, the method comprising:
   contacting a target cell with a macrophage in the presence of an antibody that specifically binds to leukocyte immunoglobulin-like receptor subfamily B member 1 (LILRB1) and does not activate signaling through LILRB1 upon binding and an antibody that binds to the target cell and thereby opsonizes the target cell, for a period of time sufficient to induce phagocytosis of the target cell by the macrophage.

8. The method according to claim 7, wherein the target cell is a cancer cell.

9. The method according to claim 7, wherein the target cell is a cell infected with an intracellular pathogen.

10. The method according to claim 7, wherein the target cell is a cancer cell of an individual having cancer, or an infected cell of an individual having a chronic intracellular pathogen infection.

11. The method according to claim 7, wherein the contacting is in vitro or ex vivo.

12. The method according to claim 7, wherein the contacting is in vivo.

13. The method according to claim 7, wherein said contacting is in the presence of an antibody that specifically binds to CD47 and blocks interaction of CD47 and SIRPα.

14. The method according to claim 7, wherein the antibody that binds to the target cell binds to CD20.

15. The method according to claim 14, wherein the antibody is rituximab.

16. The method according to claim 7, wherein the antibody that binds to the target cell binds to EGFR.

17. The method according to claim 16, wherein the antibody is cetuximab.

* * * * *

SEQUENCE LISTING

<160> NUMBER OF SEQ ID NOS: 24

<210> SEQ ID NO 1
<211> LENGTH: 650
<212> TYPE: PRT

<213> ORGANISM: Homo sapiens

<400> SEQUENCE: 1

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400
```

Gln Ser Ser Lys Pro Tyr Leu Leu Thr His Pro Ser Asp Pro Leu Glu
            405                 410                 415

Leu Val Val Ser Gly Pro Ser Gly Gly Pro Ser Ser Pro Thr Thr Gly
        420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
            485                 490                 495

Arg Lys Ala Asp Phe Gln His Pro Ala Gly Ala Val Gly Pro Glu Pro
        500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
            565                 570                 575

Pro Pro Ser Pro Leu Ser Gly Glu Phe Leu Asp Thr Lys Asp Arg Gln
        580                 585                 590

Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
            645                 650

<210> SEQ ID NO 2
<211> LENGTH: 652
<212> TYPE: PRT
<213> ORGANISM: Homo sapiens

<400> SEQUENCE: 2

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
            85                  90                  95

Arg Cys Tyr Tyr Gly Ser Asp Thr Ala Gly Arg Ser Glu Ser Ser Asp
        100                 105                 110

Pro Leu Glu Leu Val Val Thr Gly Ala Tyr Ile Lys Pro Thr Leu Ser
    115                 120                 125

```
Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
            420                 425                 430

Pro Thr Ser Thr Ser Ala Gly Pro Glu Asp Gln Pro Leu Thr Pro Thr
        435                 440                 445

Gly Ser Asp Pro Gln Ser Gly Leu Gly Arg His Leu Gly Val Val Ile
    450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
            500                 505                 510

Pro Thr Asp Arg Gly Leu Gln Trp Arg Ser Ser Pro Ala Ala Asp Ala
        515                 520                 525

Gln Glu Glu Asn Leu Tyr Ala Ala Val Lys His Thr Gln Pro Glu Asp
    530                 535                 540
```

Gly Val Glu Met Asp Thr Arg Gln Ser Pro His Asp Glu Asp Pro Gln
545                 550                 555                 560

Ala Val Thr Tyr Ala Glu Val Lys His Ser Arg Pro Arg Arg Glu Met
            565                 570                 575

Ala Ser Pro Pro Ser Pro Leu Ser Gly Glu Phe Leu Asp Thr Lys Asp
            580                 585                 590

Arg Gln Ala Glu Glu Asp Arg Gln Met Asp Thr Glu Ala Ala Ala Ser
        595                 600                 605

Glu Ala Pro Gln Asp Val Thr Tyr Ala Gln Leu His Ser Leu Thr Leu
    610                 615                 620

Arg Arg Glu Ala Thr Glu Pro Pro Pro Ser Gln Glu Gly Pro Ser Pro
625                 630                 635                 640

Ala Val Pro Ser Ile Tyr Ala Thr Leu Ala Ile His
            645                 650

<210> SEQ ID NO 3
<211> LENGTH: 651
<212> TYPE: PRT
<213> ORGANISM: Homo sapiens

<400> SEQUENCE: 3

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

```
Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Ala Gly Pro Glu Asp Gln Pro Leu Thr Pro Thr
        435                 440                 445

Gly Ser Asp Pro Gln Ser Gly Leu Gly Arg His Leu Gly Val Val Ile
    450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
            500                 505                 510

Pro Thr Asp Arg Gly Leu Gln Trp Arg Ser Ser Pro Ala Ala Asp Ala
        515                 520                 525

Gln Glu Glu Asn Leu Tyr Ala Ala Val Lys His Thr Gln Pro Glu Asp
    530                 535                 540

Gly Val Glu Met Asp Thr Arg Ser Pro His Asp Glu Asp Pro Gln Ala
545                 550                 555                 560

Val Thr Tyr Ala Glu Val Lys His Ser Arg Pro Arg Arg Glu Met Ala
                565                 570                 575

Ser Pro Pro Ser Pro Leu Ser Gly Glu Phe Leu Asp Thr Lys Asp Arg
            580                 585                 590

Gln Ala Glu Glu Asp Arg Gln Met Asp Thr Glu Ala Ala Ala Ser Glu
        595                 600                 605

Ala Pro Gln Asp Val Thr Tyr Ala Gln Leu His Ser Leu Thr Leu Arg
    610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 4
<211> LENGTH: 651
<212> TYPE: PRT
<213> ORGANISM: Homo sapiens
```

<400> SEQUENCE: 4

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415
```

```
Leu Val Val Ser Gly Pro Ser Gly Pro Ser Ser Pro Thr Thr Gly
            420                 425                 430

Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys His Thr Gln Pro Glu Asp Gly
            530                 535                 540

Val Glu Met Asp Thr Arg Gln Ser Pro His Asp Glu Asp Pro Gln Ala
545                 550                 555                 560

Val Thr Tyr Ala Glu Val Lys His Ser Arg Pro Arg Arg Glu Met Ala
                565                 570                 575

Ser Pro Pro Ser Pro Leu Ser Gly Glu Phe Leu Asp Thr Lys Asp Arg
                580                 585                 590

Gln Ala Glu Glu Asp Arg Gln Met Asp Thr Glu Ala Ala Ala Ser Glu
            595                 600                 605

Ala Pro Gln Asp Val Thr Tyr Ala Gln Leu His Ser Leu Thr Leu Arg
            610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 5
<211> LENGTH: 634
<212> TYPE: PRT
<213> ORGANISM: Homo sapiens

<400> SEQUENCE: 5

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
                85                  90                  95

Arg Cys Tyr Tyr Gly Ser Asp Thr Ala Gly Arg Ser Glu Ser Ser Asp
                100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Thr Leu Gln
```

-continued

```
            130                 135                 140
Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
                195                 200                 205

Ser Leu Pro Ser Asp Leu Leu Glu Leu Leu Val Leu Gly Val Ser Lys
            210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
            290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Ala Gly Pro Glu Asp Gln Pro Leu Thr Pro Thr Gly
            420                 425                 430

Ser Asp Pro Gln Ser Gly Leu Gly Arg His Leu Gly Val Val Ile Gly
            435                 440                 445

Ile Leu Val Ala Val Ile Leu Leu Leu Leu Leu Leu Leu Leu Leu Phe
450                 455                 460

Leu Ile Leu Arg His Arg Arg Gln Gly Lys His Trp Thr Ser Thr Gln
465                 470                 475                 480

Arg Lys Ala Asp Phe Gln His Pro Ala Gly Ala Val Gly Pro Glu Pro
                485                 490                 495

Thr Asp Arg Gly Leu Gln Trp Arg Ser Ser Pro Ala Ala Asp Ala Gln
                500                 505                 510

Glu Glu Asn Leu Tyr Ala Ala Val Lys His Thr Gln Pro Glu Asp Gly
            515                 520                 525

Val Glu Met Asp Thr Arg Ser Pro His Asp Glu Asp Pro Gln Ala Val
            530                 535                 540

Thr Tyr Ala Glu Val Lys His Ser Arg Pro Arg Arg Glu Met Ala Ser
545                 550                 555                 560
```

```
Pro Pro Ser Pro Leu Ser Gly Glu Phe Leu Asp Thr Lys Asp Arg Gln
            565                 570                 575

Ala Glu Glu Asp Arg Gln Met Asp Thr Glu Ala Ala Ala Ser Glu Ala
        580                 585                 590

Pro Gln Asp Val Thr Tyr Ala Gln Leu His Ser Leu Thr Leu Arg Arg
    595                 600                 605

Glu Ala Thr Glu Pro Pro Ser Gln Glu Gly Pro Ser Pro Ala Val
610                 615                 620

Pro Ser Ile Tyr Ala Thr Leu Ala Ile His
625                 630

<210> SEQ ID NO 6
<211> LENGTH: 456
<212> TYPE: PRT
<213> ORGANISM: Homo sapiens

<400> SEQUENCE: 6

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Thr Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
```

```
                290                 295                 300
Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
            420                 425                 430

Pro Thr Ser Thr Ser Ala Gly Pro Glu Asp Gln Pro Leu Thr Pro Thr
        435                 440                 445

Gly Ser Asp Pro Gln Ser Gly Glu
    450                 455

<210> SEQ ID NO 7
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 7

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Phe
                85                  90                  95

Thr Phe Gly Ser Gly Thr Lys Leu Glu Ile Lys
            100                 105

<210> SEQ ID NO 8
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 8

Gln Thr Ile Gly Thr Trp
1               5

<210> SEQ ID NO 9
<211> LENGTH: 3
```

```
<212> TYPE: PRT
<213> ORGANISM: Artificial sequence
<220> FEATURE:
<223> OTHER INFORMATION: Synthetic amino acid sequence

<400> SEQUENCE: 9

Ala Ala Thr
1

<210> SEQ ID NO 10
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 10

Cys Gln Gln Leu Tyr Ser Thr Pro Phe Thr
1               5                   10

<210> SEQ ID NO 11
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 11

Glu Val Ile Leu Val Glu Ser Gly Gly Ala Leu Val Arg Pro Gly Gly
1               5                   10                  15

Ser Leu Lys Leu Ser Cys Ala Ala Ser Gly Phe Thr Phe Ser Ser Asn
            20                  25                  30

Ala Met Ser Trp Val Arg Gln Thr Pro Glu Lys Arg Leu Glu Trp Val
        35                  40                  45

Ala Thr Ile Ser Asn Gly Gly Thr Phe Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Arg His Gly Asp Gly Asn Tyr Gly Asp Pro Leu Asp Tyr Trp Gly
            100                 105                 110

Gln Gly Thr Thr Leu Thr Val Ser Ser
        115                 120

<210> SEQ ID NO 12
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 12

Phe Thr Phe Ser Ser Asn Ala
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 13
```

```
Ile Ser Asn Gly Gly Thr Phe Thr
1               5

<210> SEQ ID NO 14
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 14

Cys Ala Arg His Gly Asp Gly Asn Tyr Gly Asp Pro Leu
1               5                   10

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 15
tgtcgtcatt ccatgctttg                                           20

<210> SEQ ID NO 16
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 16
tatacttcag tagtgttttg                                           20

<210> SEQ ID NO 17
<211> LENGTH: 384
<212> TYPE: DNA
<213> ORGANISM: Artificial sequence
<220> FEATURE:
<223> OTHER INFORMATION: Synthetic nucleic acid sequence

<400> SEQUENCE: 17
tttaagctag catgtctcgc tccgtggcct tagctgtgct cgcgctactc tctctttctg    60
gcctggaggc tatccagcgt actccaaaga ttcaggttta ctcacgtcat ccagcagaga   120
atggaaagtc aaatttcctg aattgctatg tgtctgggtt tcatccatcc gacattgaag   180
ttgacttact gaagaatgga gagagaattg aaaaagtgga gcattcagac ttgtctttca   240
gcaaggactg gtctttctat ctcttgtact acactgaatt caccccccact gaaaaagatg   300 agtatgcctg cagagttaag catgccagta tggccgagcc caagaccgtc tactgggatc   360
gagacatgtg agcggccgca attt                                        384

<210> SEQ ID NO 18
<211> LENGTH: 21
<212> TYPE: DNA
<213> ORGANISM: Artificial sequence
<220> FEATURE:
<223> OTHER INFORMATION: Synthetic sequence

<400> SEQUENCE: 18
gctactgaag tatacgtaaa g                                           21

<210> SEQ ID NO 19
```

```
<211> LENGTH: 21
<212> TYPE: DNA
<213> ORGANISM: Artificial sequence
<220> FEATURE:
<223> OTHER INFORMATION: Synthetic sequence

<400> SEQUENCE: 19
gcttgtttag agctccatca a                                              21

<210> SEQ ID NO 20
<211> LENGTH: 20
<212> TYPE: DNA
<213> ORGANISM: Artificial sequence
<220> FEATURE:
<223> OTHER INFORMATION: Synthetic sequence

<400> SEQUENCE: 20
gagtagcgcg agcacagcta                                                20

<210> SEQ ID NO 21
<211> LENGTH: 20
<212> TYPE: DNA
<213> ORGANISM: Artificial sequence
<220> FEATURE:
<223> OTHER INFORMATION: Synthetic sequence

<400> SEQUENCE: 21
ggccgagatg tctcgctccg                                                20

<210> SEQ ID NO 22
<211> LENGTH: 20
<212> TYPE: DNA
<213> ORGANISM: Artificial sequence
<220> FEATURE:
<223> OTHER INFORMATION: Synthetic sequence

<400> SEQUENCE: 22
tgtcgtcatt ccatgctttg                                                20

<210> SEQ ID NO 23
<211> LENGTH: 20
<212> TYPE: DNA
<213> ORGANISM: Artificial sequence
<220> FEATURE:
<223> OTHER INFORMATION: Synthetic sequence

<400> SEQUENCE: 23
tatacttcag tagtgttttg                                                20

<210> SEQ ID NO 24
<211> LENGTH: 384
<212> TYPE: DNA
<213> ORGANISM: Artificial sequence
<220> FEATURE:
<223> OTHER INFORMATION: Synthetic sequence

<400> SEQUENCE: 24
tttaagctag catgtctcgc tccgtggcct tagctgtgct cgcgctactc tctctttctg     60
gcctggaggc tatccagcgt actccaaaga ttcaggttta ctcacgtcat ccagcagaga    120
atggaaagtc aaatttcctg aattgctatg tgtctgggtt tcatccatcc gacattgaag    180
ttgacttact gaagaatgga gagagaattg aaaaagtgga gcattcagac ttgtctttca    240
gcaaggactg gtcttttctat ctcttgtact acactgaatt cacccccact gaaaaagatg    300
agtatgcctg cagagttaag catgccagta tggccgagcc caagaccgtc tactgggatc    360
gagacatgtg agcggccgca attt                                          384
```